(12) United States Patent
Rush et al.

(10) Patent No.: US 10,600,204 B1
(45) Date of Patent: Mar. 24, 2020

(54) MEDICAL ENVIRONMENT BEDSORE DETECTION AND PREVENTION SYSTEM

(71) Applicant: Ocuvera, Lincoln, NE (US)

(72) Inventors: Benjamin D. Rush, Lincoln, NE (US); Joshua M. Brown-Kramer, Lincoln, NE (US); Lucas A. Sabalka, Lincoln, NE (US); Brian S. Gansemer, Lincoln, NE (US); Clay T. Upton, Lincoln, NE (US); Paul B. Bauer, Lincoln, NE (US); Andrew R. Unterseher, Lincoln, NE (US); Benjamin J. Origas, Lincoln, NE (US); Douglas W. Durham, Lincoln, NE (US)

(73) Assignee: Ocuvera, Lincoln, NE (US)

( * ) Notice: Subject to any disclaimer, the term of this patent is extended or adjusted under 35 U.S.C. 154(b) by 103 days.

(21) Appl. No.: 15/856,753

(22) Filed: Dec. 28, 2017

Related U.S. Application Data

(60) Provisional application No. 62/439,556, filed on Dec. 28, 2016.

(51) Int. Cl.
*G06T 7/73* (2017.01)
*A61B 5/11* (2006.01)
*A61B 5/00* (2006.01)

(52) U.S. Cl.
CPC .............. *G06T 7/74* (2017.01); *A61B 5/1113* (2013.01); *A61B 5/447* (2013.01); *A61B 5/746* (2013.01);
(Continued)

(58) Field of Classification Search
CPC ....... A61B 5/1113; A61B 5/447; A61B 5/746; G06T 2207/10016; G06T 2207/10028; G06T 2207/30196; G06T 7/74
See application file for complete search history.

(56) References Cited

U.S. PATENT DOCUMENTS

| 7,110,569 | B2 | 9/2006 | Brodsky et al. |
| 7,541,934 | B2 | 6/2009 | Fredriksson et al. |

(Continued)

FOREIGN PATENT DOCUMENTS

| EP | 2100798 B1 | 5/2011 |
| EP | 2272479 B1 | 8/2013 |

(Continued)

OTHER PUBLICATIONS

Banerjee et al., "Monitoring patients in hospital beds using unobtrusive depth sensors," Conf Proc IEEE Eng Med Biol Soc. 2014;2014:5904-7.

(Continued)

*Primary Examiner* — Leon Flores
(74) *Attorney, Agent, or Firm* — Bejin Bieneman PLC

(57) ABSTRACT

A system and a method are described for preventing pressure ulcers in a medical care environment by monitoring adherence to a pressure ulcer prevention protocol. The method also includes identifying a first subset of pixels from the plurality of potential locations as representing a bed and/or a seating platform. The method also includes identifying a second subset of pixels within the field of view of the camera as representing an object (e.g., a subject, such as a patient, medical personnel; bed; chair; patient tray; medical equipment; etc.) proximal to the bed and/or seating platform. The method also includes determining an orientation of the object with respect to the bed and/or seating platform, and determining changes in the orientation and/or position of the object over a period of time. In implementations, the method further includes issuing an electronic communication alert based upon the determined orientation and/or position of the object over the period of time.

17 Claims, 24 Drawing Sheets

(52) U.S. Cl.
CPC .............. *G06T 2207/10016* (2013.01); *G06T 2207/10028* (2013.01); *G06T 2207/30196* (2013.01)

(56) References Cited

U.S. PATENT DOCUMENTS

| | | | |
|---|---|---|---|
| 7,612,666 B2 | 11/2009 | Badawy | |
| 8,344,860 B2 | 1/2013 | Collins, Jr. et al. | |
| 8,360,308 B2 | 1/2013 | Herbst et al. | |
| 8,368,545 B2 | 2/2013 | Zerhusen et al. | |
| 8,413,273 B2 | 4/2013 | Hornbach et al. | |
| 8,421,606 B2 | 4/2013 | Collins, Jr. et al. | |
| 8,457,989 B2 | 6/2013 | Gedeon et al. | |
| 8,487,774 B2 | 7/2013 | Reeder et al. | |
| 8,525,680 B2 | 9/2013 | Riley et al. | |
| 8,537,008 B2 | 9/2013 | Tallent et al. | |
| 8,593,284 B2 | 11/2013 | Tallent et al. | |
| 8,620,625 B2 | 12/2013 | Sing et al. | |
| 8,620,682 B2 | 12/2013 | Bechtel et al. | |
| 8,675,059 B2 | 3/2014 | Johnson et al. | |
| 8,675,920 B2 | 3/2014 | Hanson et al. | |
| 8,688,467 B2 | 4/2014 | Harrison et al. | |
| 8,727,981 B2 | 5/2014 | Bechtel et al. | |
| 8,752,220 B2 | 6/2014 | Soderberg et al. | |
| 8,766,804 B2 | 7/2014 | Reeder et al. | |
| 8,799,011 B2 | 8/2014 | Wilson et al. | |
| 8,844,078 B2 | 9/2014 | Hornbach et al. | |
| 8,847,756 B2 | 9/2014 | Tallent et al. | |
| 8,882,684 B2 | 11/2014 | Halperin et al. | |
| 8,907,287 B2 | 12/2014 | Vanderpohl | |
| 8,998,830 B2 | 4/2015 | Halperin et al. | |
| 9,016,563 B2 | 4/2015 | Zerhusen et al. | |
| 9,041,810 B2 | 5/2015 | Ecker et al. | |
| 9,084,585 B1 | 7/2015 | McNair | |
| 9,117,183 B2 | 8/2015 | Buchan et al. | |
| 9,129,506 B1 | 9/2015 | Kusens | |
| 9,159,215 B1 | 10/2015 | Kusens | |
| 9,165,449 B2 | 10/2015 | Ribble et al. | |
| 9,204,823 B2 | 12/2015 | Derenne et al. | |
| 9,230,421 B2 | 1/2016 | Reeder et al. | |
| 9,277,878 B2 | 3/2016 | McClure et al. | |
| 9,295,390 B2 | 3/2016 | Receveur et al. | |
| 9,301,689 B2 | 4/2016 | Vanderpohl | |
| 9,311,540 B2 | 4/2016 | Ecker et al. | |
| 9,336,672 B2 | 5/2016 | Collins, Jr. et al. | |
| 9,349,267 B2 | 5/2016 | Wildman et al. | |
| 9,351,641 B2 | 5/2016 | Neff | |
| 9,358,168 B2 | 6/2016 | Williamson et al. | |
| 9,375,374 B2 | 6/2016 | Herman et al. | |
| 9,383,250 B2 | 7/2016 | Receveur et al. | |
| 9,383,251 B2 | 7/2016 | Dixon et al. | |
| 9,393,366 B2 | 7/2016 | Gannon et al. | |
| 9,396,638 B2 | 7/2016 | Wildman et al. | |
| 9,411,934 B2 | 8/2016 | Robinson et al. | |
| 9,427,365 B2 | 8/2016 | Richards et al. | |
| 9,433,300 B2 | 9/2016 | Gibson et al. | |
| 9,439,604 B2 | 9/2016 | Heil et al. | |
| 9,445,789 B2 | 9/2016 | Whited et al. | |
| 9,449,493 B2 | 9/2016 | Shinar et al. | |
| 9,456,780 B2 | 10/2016 | Ribble et al. | |
| 9,462,893 B2 | 10/2016 | Romano et al. | |
| 9,463,124 B2 | 10/2016 | Lachenbruch et al. | |
| 9,463,126 B2 | 10/2016 | Zerhusen et al. | |
| 9,465,915 B2 | 10/2016 | McNeely et al. | |
| 9,465,916 B2 | 10/2016 | Girardeau et al. | |
| 9,466,877 B2 | 10/2016 | Dixon et al. | |
| 9,479,511 B2 | 10/2016 | Dittrich et al. | |
| D770,824 S | 11/2016 | O'Neal et al. | |
| D770,827 S | 11/2016 | Newkirk et al. | |
| D770,828 S | 11/2016 | Newkirk et al. | |
| D770,829 S | 11/2016 | Newkirk et al. | |
| D771,259 S | 11/2016 | Newkirk et al. | |
| 9,483,614 B2 | 11/2016 | Ash et al. | |
| 9,486,374 B2 | 11/2016 | Heimbrock et al. | |
| 9,488,552 B2 | 11/2016 | Whited et al. | |
| 9,489,818 B2 | 11/2016 | Vanderpohl, III | |
| 9,489,820 B1 | 11/2016 | Kusens | |
| 9,492,340 B2 | 11/2016 | Hornbach et al. | |
| 9,492,341 B2 | 11/2016 | Huster et al. | |
| 9,495,514 B2 | 11/2016 | McNair | |
| 9,501,619 B2 | 11/2016 | Portnoy et al. | |
| 9,510,687 B2 | 12/2016 | Lachenbruch | |
| 9,513,899 B2 | 12/2016 | Collins, Jr. et al. | |
| 9,517,034 B2 | 12/2016 | Collins, Jr. et al. | |
| 9,517,035 B2 | 12/2016 | Schuman et al. | |
| 9,519,969 B1 | 12/2016 | Kusens | |
| 9,524,443 B1 | 12/2016 | Kusens | |
| 9,526,348 B2 | 12/2016 | Richards et al. | |
| 9,538,158 B1 | 1/2017 | Rush et al. | |
| 9,539,156 B2 | 1/2017 | Lemire et al. | |
| 9,552,714 B2 | 1/2017 | Ribble et al. | |
| 9,558,641 B2 | 1/2017 | Brasch et al. | |
| 2012/0026308 A1* | 2/2012 | Johnson | G06K 9/00369 348/77 |
| 2012/0075464 A1 | 3/2012 | Derenne et al. | |
| 2013/0096575 A1 | 4/2013 | Olson | |
| 2013/0219622 A1 | 8/2013 | Hornbach et al. | |
| 2013/0245502 A1 | 9/2013 | Lange et al. | |
| 2013/0267791 A1 | 10/2013 | Halperin et al. | |
| 2013/0268297 A1 | 10/2013 | Gedeon et al. | |
| 2013/0300558 A1 | 11/2013 | Reeder et al. | |
| 2014/0015677 A1 | 1/2014 | Tallent et al. | |
| 2014/0022081 A1 | 1/2014 | Ribble et al. | |
| 2014/0035925 A1 | 2/2014 | Muranjan et al. | |
| 2014/0092247 A1 | 4/2014 | Clark et al. | |
| 2014/0168397 A1 | 6/2014 | Greco et al. | |
| 2014/0191038 A1 | 7/2014 | Zerhusen et al. | |
| 2014/0204207 A1 | 7/2014 | Clark et al. | |
| 2014/0213845 A1 | 7/2014 | Bechtel et al. | |
| 2014/0222446 A1 | 8/2014 | Ash et al. | |
| 2014/0247334 A1 | 9/2014 | Johnson et al. | |
| 2014/0259410 A1 | 9/2014 | Zerhusen et al. | |
| 2014/0267625 A1* | 9/2014 | Clark | A61B 5/002 348/46 |
| 2014/0313340 A1 | 10/2014 | Ecker et al. | |
| 2014/0320290 A1 | 10/2014 | Reeder et al. | |
| 2014/0323816 A1 | 10/2014 | Soderberg et al. | |
| 2014/0350351 A1 | 11/2014 | Halperin et al. | |
| 2015/0081335 A1 | 3/2015 | Dixon et al. | |
| 2015/0141838 A1 | 5/2015 | Vanderpohl | |
| 2015/0164438 A1 | 6/2015 | Halperin et al. | |
| 2015/0193583 A1 | 7/2015 | McNair et al. | |
| 2015/0221198 A1 | 8/2015 | Collins, Jr. et al. | |
| 2015/0227716 A1 | 8/2015 | Ryan et al. | |
| 2015/0244993 A1 | 8/2015 | Greco et al. | |
| 2015/0281659 A1 | 10/2015 | Hood et al. | |
| 2015/0297121 A1 | 10/2015 | Eadelman et al. | |
| 2015/0351983 A1 | 12/2015 | McNeely et al. | |
| 2016/0008197 A1 | 1/2016 | Zerhusen et al. | |
| 2016/0117450 A1 | 4/2016 | Zerhusen et al. | |
| 2016/0125150 A1 | 5/2016 | Foster et al. | |
| 2016/0125716 A1 | 5/2016 | Ribble et al. | |
| 2016/0136356 A1 | 5/2016 | Ribble et al. | |
| 2016/0143449 A1 | 5/2016 | Lachenbruch | |
| 2016/0148489 A1 | 5/2016 | Reeder et al. | |
| 2016/0154656 A1 | 6/2016 | Illindala et al. | |
| 2016/0166214 A1 | 6/2016 | Schuman et al. | |
| 2016/0166215 A1 | 6/2016 | Mazin et al. | |
| 2016/0174909 A1 | 6/2016 | Collins, Jr. et al. | |
| 2016/0180039 A1 | 6/2016 | Hayes | |
| 2016/0180040 A1 | 6/2016 | Ryan et al. | |
| 2016/0180668 A1 | 6/2016 | Kusens et al. | |
| 2016/0183864 A1 | 6/2016 | Kusens et al. | |
| 2016/0188804 A1 | 6/2016 | Lowery et al. | |
| 2016/0188811 A1 | 6/2016 | Wager et al. | |
| 2016/0188822 A1 | 6/2016 | Ryan et al. | |
| 2016/0188832 A1 | 6/2016 | Kramer | |
| 2016/0188833 A1 | 6/2016 | Kramer | |
| 2016/0188834 A1 | 6/2016 | Erdmann et al. | |
| 2016/0188843 A1 | 6/2016 | Staples, II et al. | |
| 2016/0188844 A1 | 6/2016 | Wager et al. | |
| 2016/0188965 A1 | 6/2016 | McClure et al. | |
| 2016/0193483 A1 | 7/2016 | Mazin et al. | |
| 2016/0204937 A1 | 7/2016 | Edwards et al. | |

(56) References Cited

U.S. PATENT DOCUMENTS

| | | |
|---|---|---|
| 2016/0213255 A1 | 7/2016 | Ribble |
| 2016/0213539 A1 | 7/2016 | Gibson et al. |
| 2016/0220661 A1 | 8/2016 | Ault-Riche et al. |
| 2016/0223560 A1 | 8/2016 | Ault-Riche et al. |
| 2016/0224734 A1 | 8/2016 | Ryan et al. |
| 2016/0235210 A1 | 8/2016 | Lachenbruch et al. |
| 2016/0238490 A1 | 8/2016 | Whited et al. |
| 2016/0239617 A1 | 8/2016 | Farooq et al. |
| 2016/0246941 A1 | 8/2016 | Miller et al. |
| 2016/0246946 A1 | 8/2016 | Haley |
| 2016/0250088 A1 | 9/2016 | Williamson et al. |
| 2016/0253897 A1 | 9/2016 | Wildman et al. |
| 2016/0259906 A1 | 9/2016 | Lucha et al. |
| 2016/0259907 A1 | 9/2016 | Nedblake et al. |
| 2016/0299121 A1 | 10/2016 | Fu et al. |
| 2016/0299122 A1 | 10/2016 | Fu et al. |
| 2016/0300472 A1 | 10/2016 | Eadelman et al. |
| 2016/0307429 A1 | 10/2016 | Hood et al. |
| 2016/0310045 A1 | 10/2016 | Hoffman et al. |
| 2016/0314258 A1 | 10/2016 | Kusens |
| 2016/0314672 A1 | 10/2016 | Wiggermann et al. |
| 2016/0317742 A1 | 11/2016 | Gannon et al. |
| 2016/0321805 A1 | 11/2016 | Neff |
| 2016/0324460 A1 | 11/2016 | Kusens |
| 2016/0324707 A1 | 11/2016 | Lachenbruch et al. |
| 2016/0327426 A1 | 11/2016 | Nachtigal et al. |
| 2016/0331616 A1 | 11/2016 | Fisk et al. |
| 2016/0338591 A1 | 11/2016 | Lachenbruch et al. |
| 2016/0338891 A1 | 11/2016 | Agdeppa et al. |
| 2016/0350489 A1 | 12/2016 | Ribble et al. |
| 2016/0353900 A1 | 12/2016 | Williams et al. |
| 2016/0354043 A1 | 12/2016 | Heil et al. |
| 2016/0354264 A1 | 12/2016 | Richards et al. |
| 2016/0354588 A1 | 12/2016 | Ribble et al. |
| 2016/0356676 A1 | 12/2016 | Sauser et al. |
| 2016/0358452 A1 | 12/2016 | Dixon et al. |
| 2016/0361215 A1 | 12/2016 | Gibson et al. |
| 2016/0361566 A1 | 12/2016 | Larkin et al. |
| 2016/0364530 A1 | 12/2016 | Herbst et al. |
| 2016/0364535 A1 | 12/2016 | Kusens |
| 2016/0367040 A1 | 12/2016 | Borgman et al. |
| 2016/0367419 A1 | 12/2016 | Bhai et al. |
| 2016/0367420 A1 | 12/2016 | Zerhusen et al. |
| 2016/0371786 A1 | 12/2016 | Kusens et al. |
| 2016/0374626 A1 | 12/2016 | Heil et al. |
| 2016/0374847 A1 | 12/2016 | Lachenbruch et al. |
| 2016/0374882 A1 | 12/2016 | Kaikenger et al. |
| 2016/0375219 A1 | 12/2016 | Kaikenger |
| 2017/0014648 A1 | 1/2017 | Mostafavi |
| 2017/0032648 A1 | 2/2017 | McClain et al. |
| 2017/0032650 A1 | 2/2017 | Wiggermann et al. |
| 2017/0055882 A1 | 3/2017 | Al-Ali et al. |
| 2017/0061763 A1 | 3/2017 | Hanson et al. |
| 2017/0084158 A1 | 3/2017 | Kusens |
| 2017/0091562 A1 | 3/2017 | Kusens |
| 2017/0098360 A1 | 4/2017 | Ribble et al. |
| 2017/0115171 A1 | 4/2017 | Huang et al. |

FOREIGN PATENT DOCUMENTS

| | | |
|---|---|---|
| EP | 2664314 A1 | 11/2013 |
| EP | 2669754 A2 | 12/2013 |
| EP | 2165691 B1 | 5/2014 |
| EP | 2973475 A2 | 1/2016 |
| EP | 2777670 B1 | 2/2016 |
| EP | 3015098 A2 | 5/2016 |
| EP | 3023897 A1 | 5/2016 |
| EP | 3032029 A1 | 6/2016 |
| EP | 3033661 A1 | 6/2016 |
| EP | 3037080 A1 | 6/2016 |
| EP | 1754462 B1 | 7/2016 |
| EP | 2268369 B1 | 7/2016 |
| EP | 2695592 B1 | 7/2016 |
| EP | 2851051 B1 | 7/2016 |
| EP | 3045158 A1 | 7/2016 |
| EP | 2973460 A4 | 8/2016 |
| EP | 3056178 A1 | 8/2016 |
| EP | 3056179 A1 | 8/2016 |
| EP | 3058923 A1 | 8/2016 |
| EP | 3061436 A1 | 8/2016 |
| EP | 2302541 B1 | 9/2016 |
| EP | 2444114 B1 | 9/2016 |
| EP | 2762122 B1 | 9/2016 |
| EP | 2901994 B1 | 9/2016 |
| EP | 3065073 A2 | 9/2016 |
| EP | 1906793 B1 | 10/2016 |
| EP | 2332597 B1 | 10/2016 |
| EP | 3078323 A1 | 10/2016 |
| EP | 3081154 A1 | 10/2016 |
| EP | 3081203 A1 | 10/2016 |
| EP | 1983957 B1 | 11/2016 |
| EP | 2100578 B1 | 11/2016 |
| EP | 2319474 B1 | 11/2016 |
| EP | 2777672 B1 | 11/2016 |
| EP | 3087963 A1 | 11/2016 |
| EP | 3087964 A1 | 11/2016 |
| EP | 3090718 A1 | 11/2016 |
| EP | 3094295 A1 | 11/2016 |
| EP | 3094296 A1 | 11/2016 |
| EP | 3098739 A1 | 11/2016 |
| EP | 3103384 A1 | 12/2016 |
| EP | 3103385 A1 | 12/2016 |
| EP | 3103428 A1 | 12/2016 |
| EP | 3108862 A1 | 12/2016 |
| EP | 3108866 A1 | 12/2016 |
| EP | 3108921 A1 | 12/2016 |
| EP | 2590610 B1 | 5/2017 |
| WO | WO-2013028961 A1 | 2/2013 |
| WO | WO-2012006545 A9 | 4/2013 |
| WO | WO-2013150523 A1 | 10/2013 |
| WO | WO-2014165041 A2 | 10/2014 |
| WO | WO-2015137999 A1 | 9/2015 |
| WO | WO-2015160657 A1 | 10/2015 |
| WO | WO-2016013348 A1 | 1/2016 |
| WO | WO-2016035073 A1 | 3/2016 |
| WO | WO-2016115174 A1 | 7/2016 |
| WO | WO-2016159889 A1 | 10/2016 |
| WO | WO-2016196403 A1 | 12/2016 |
| WO | WO-2016197221 A1 | 12/2016 |
| WO | WO-2017026611 A1 | 2/2017 |
| WO | WO-2017034534 A1 | 3/2017 |
| WO | WO-2017056476 A1 | 4/2017 |

OTHER PUBLICATIONS

Rantz et al., "Automated fall detection with quality improvement "rewind" to reduce falls in hospital rooms," J Gerontol Nurs. Jan. 2014;40(1):13-7.

Ni et al. "RGBD-Camera Based Get-Up Event Detection for Hospital Fall Prevention." Acoustics, Speech and Signal Processing (ICASSP). 2012 IEEEInternational Conf. Mar. 2012: pp. 1405-1408.

Ross Girshick, et al. "Efficient Regression of General-Activity Human Poses from Depth Images"—Publication, Oct. 2011—8 pages.

Jamie Shotton, et al. "Real-Time Human Pose Recognition in Parts from a Single Depth Image"—Publication, Jun. 2011—8 pp.

Rose Johnson, et al. "Exploring the Potential for Touchless Interaction in Image Guided Interventional Radiology"—Publication, May 2011—10 pp.

Jamie Shotton, et al. "TextonBoost for Image Understanding: Multi-Class Object Recognition and Segmentation by Jointly Modeling Texture, Layout and Context"—Pub. Jan. 2009.

Toby Sharp "Implementing Decision Trees and Forests on a GPU"—Publication, 2008—14 pages.

Jamie Shotton, et al. "Semantic Texton Forests for Image Categorization and Segmentation"—Publication, 2008—8 pages.

U.S. Appl. No. 15/452,855; Rush et al., filed Dec. 28, 2017.

\* cited by examiner

MEDICAL ENVIRONMENT BEDSORE DETECTION AND PREVENTION SYSTEM

CROSS-REFERENCE TO RELATED APPLICATIONS

This application claims the benefit of U.S. Provisional Application No. 62/439,556, filed on Dec. 28, 2016. The entire disclosure of the application referenced above is incorporated herein by reference.

BACKGROUND

Pressure ulcers (e.g., bedsores, pressure sores, decubitus ulcers, etc.) are localized lesions to the skin and/or tissue that can develop over a bony prominence as the result of pressure, or pressure in combination with shear and/or friction. The most common sites for pressure ulcers are the skin overlying the sacrum, coccyx, heels or the hips, but other sites such as the elbows, knees, ankles or the back of the cranium can be affected.

SUMMARY

A system and a method are described for detecting and preventing pressure ulcers in a medical care environment. For example, a system and a method are described for monitoring a patient proximal to a bed, chair, or other seating platform to detect the patient orientation and patient activity levels. In one or more implementations, the method includes identifying a plurality of potential locations within a field of view of a camera as representing a bed and/or a seating platform. The method also includes identifying a first subset of pixels within the plurality of potential locations as representing a bed and/or a seating platform. The system or method also includes identifying a second subset of pixels within the field of view of the camera as representing an object (e.g., a subject, such as a patient, medical personnel; bed; chair; wheelchair; patient tray; medical equipment; etc.) proximal to the bed and/or seating platform. The method also includes determining an orientation of the object with respect to the bed and/or seating platform, and determining changes in the orientation or position of the object over a defined period of time. In implementations, the method further includes issuing an electronic communication alert based upon the determined orientation and/or position of the object over the time period. The method can further include determining whether to issue future alerts based upon feedback to the alert.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. The use of the same reference numbers in different instances in the description and the figures may indicate similar or identical items.

DETAILED DESCRIPTION

Overview

Figure 1A:
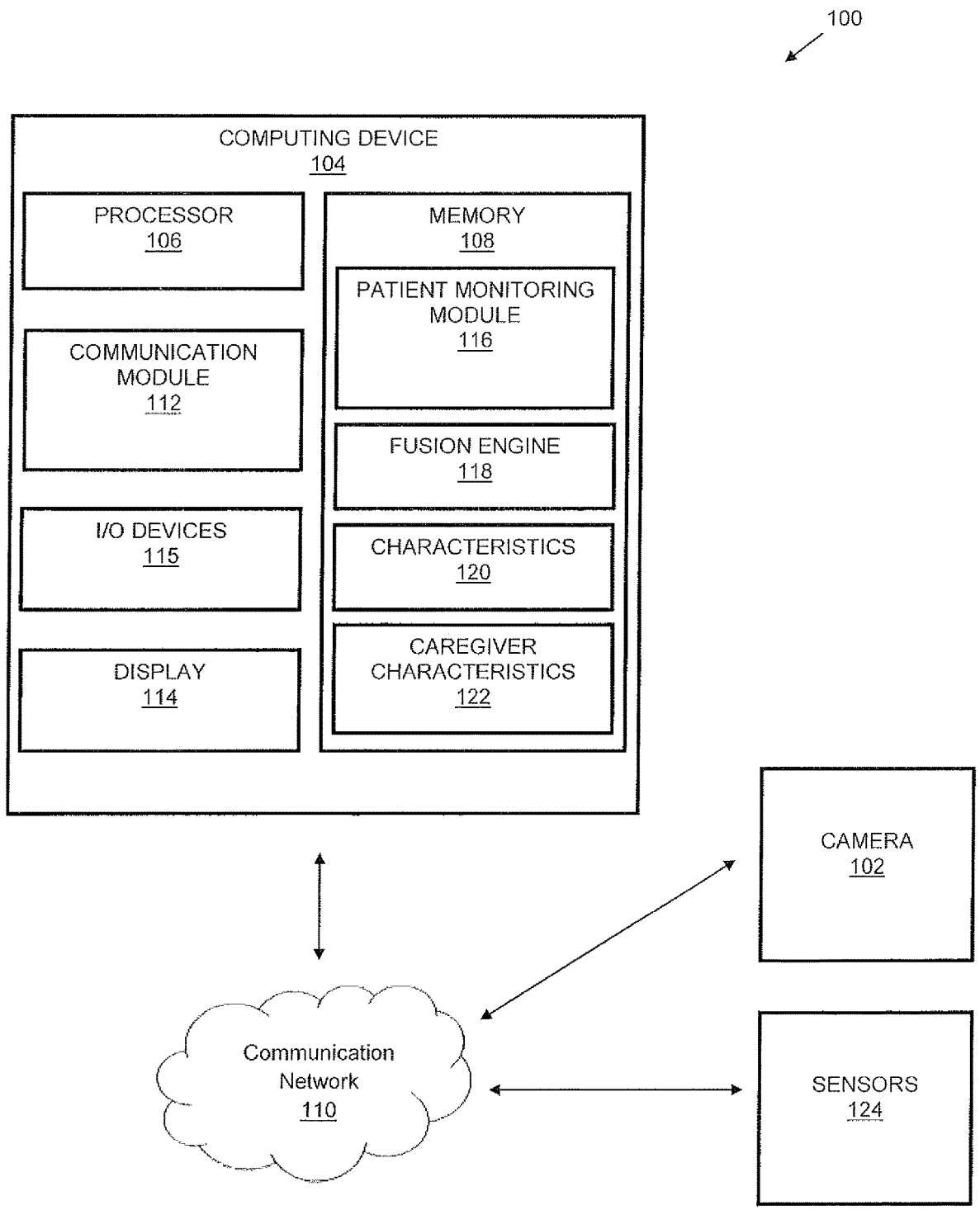
FIGS. 1A and 1B are block diagrams of an image capture system in accordance with example implementations of the present disclosure.

Pressure ulcers are localized injuries (e.g., lesions) to the skin and underlying tissue resulting from pressure or force applied to the skin. Pressure ulcers can be caused by a variety of types of tissue forces, such as pressure (e.g., compression of tissues), shear force (e.g., where the patient's skin remains stationary while the deep fascia and skeletal muscle move), friction (e.g., a force resisting the shearing of the skin), and so forth. The frequency, severity, and duration of pressure ulcers can be aggravated by factors such as moisture around the skin, humidity, temperature, age, continence, nutrition, and medication. While pressure ulcers may occur on any part of the body, they are most commonly develop on the skin covering bony areas such as the heels, ankles, hips, elbows, sacrum, tailbone, and back of the head. Pressure ulcers tend to affect people with limited mobility, particularly those confined to a bed or sitting (e.g., in a wheelchair) for prolonged periods of time.

The National Pressure Ulcer Advisory Panel (NPUAP) has categorized pressure ulcers into multiple stages: (Suspected) Deep Tissue Injury is a pre-ulcerous stage indicated by a purple or maroon localized area of discolored intact skin or blood-filled blister due to damage of underlying soft tissue from pressure or shear. Stage I is the most superficial ulcer stage, indicated by intact skin with signs of impending ulceration and initially presenting as blanchable erythema indicating reactive hyperemia. Stage II presents as partial-thickness loss of skin (e.g., damage to such as a blister or abrasion) involving epidermis and dermis. Stage III is a full-thickness loss of skin with extension into subcutaneous tissue but not through the underlying fascia. Stage IV is a pressure ulcer with full-thickness tissue loss that may extend into muscle, bone, tendon, or joint capsule. Unstageable pressure ulcers involve full-thickness tissue loss in which the base of the ulcer is covered by slough or eschar to such an extent that the full depth of the wound cannot be appreciated. Higher stage ulcers are associated with longer healing times.

Pressure ulcers occur frequently in the medical environment. Pressure ulcers are one of the most common conditions encountered in acutely hospitalized patients and patients in long-term institutional care facilities. Approximately 2.5 million pressure ulcers are treated each year in acute care facilities alone. According to the Centers for Disease Control and Prevention (CDC), about 11% of nursing home residents have pressure ulcers. Further, pressure ulceration in elderly patients is associated with a fivefold increase in mortality. Approximately 60,000 patients die each year as a direct result of pressure ulcers.

Pressure ulcers can be prevented and treated by removing the source of pressure. The most common preventative therapy is "turning," or changing the patient's position to prevent buildup of pressure on the skin and/or loss of circulation. Turning has been universally accepted as a key factor in pressure ulcer prevention and healthcare facilities implement this practice in regimented pressure ulcer prevention protocol. These protocols define a schedule for turning a patient at risk of developing pressure ulcers (e.g., every 2 hours).

Despite the simplicity of the concept of turning or repositioning a patient, many healthcare facilities fail to implement turning procedures and protocols properly. Properly implementing turning techniques can be labor-intensive and time consuming. Ideally, each patient should have a turning protocol developed by a medical professional (e.g., physician), and turning should be completed at intervals set forth by that medical professional. Additionally, each healthcare facility should implement minimum turning guidelines, which require the patient to be repositioned every two hours for bed-bound patients and every 15 minutes for chair-bound patients. Patients should be turned an adequate degree at the prescribed time, as less-than-adequate turns fail to decrease the risk of developing pressure ulcers. Many patients (e.g., those with limited mobility) cannot accomplish the task of turning without assistance from healthcare facility staff. Further, patients who spend a significant amount of time seated (e.g., in a wheelchair) must be periodically removed from the seat and repositioned at intervals set forth by a physician.

Documentation procedures for a pressure ulcer treatment and prevention protocol are also manually intensive. This results in undocumented treatments, protocols not being correctly adhered to, and an inability to prove the protocol was correctly adhered to. For example, if documentation is incomplete, a patient may be turned before the normally scheduled time because staff is unaware of a recent, previous turn. This may reduce the effectiveness of a pressure ulcer prevention protocol and increase the risk of pressure ulcers for a patient.

Example Pressure Ulcer Detection and Prevention Implementation

Figure 1B:
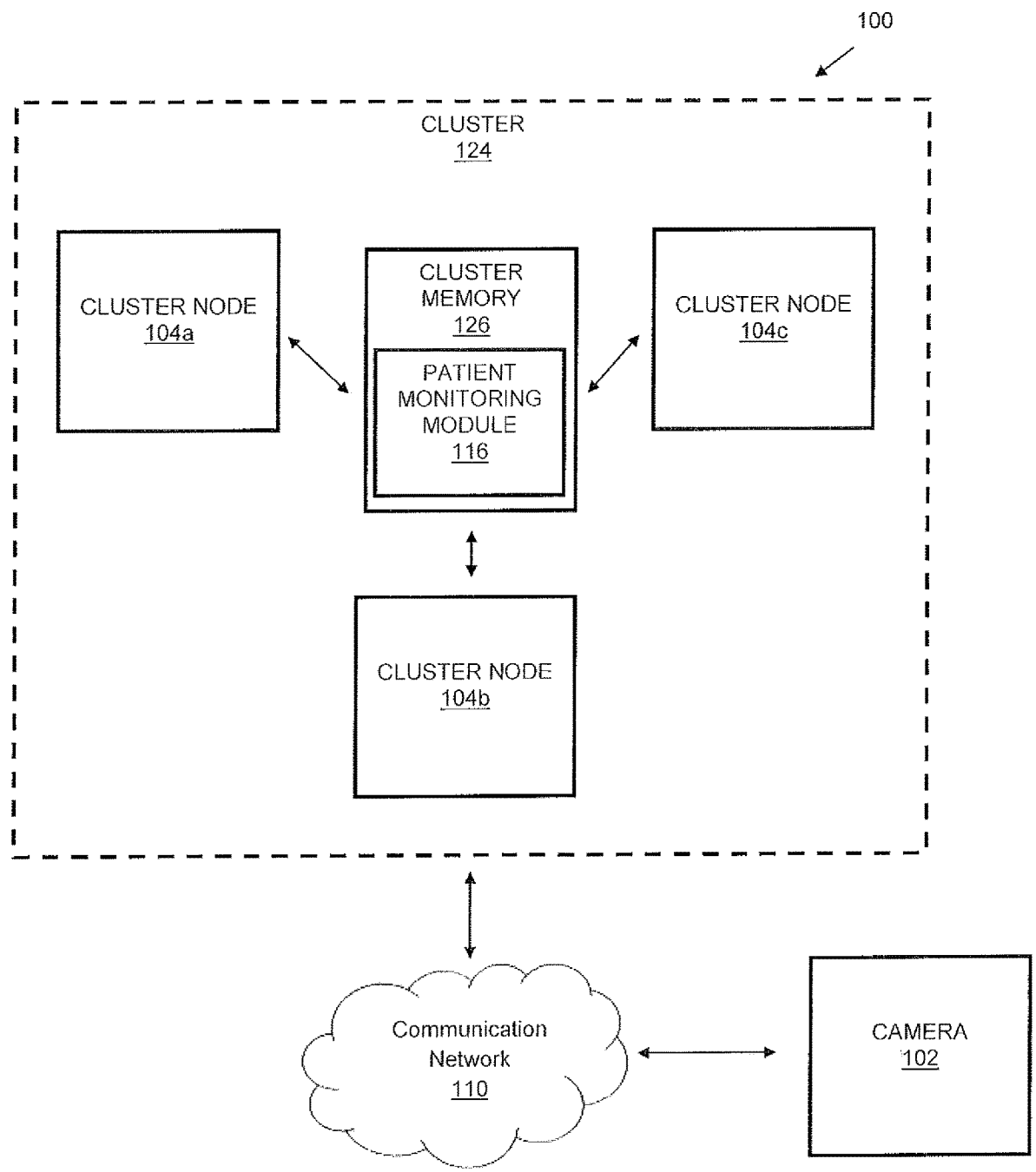

FIGS. 1A through 1B illustrate an image capture system 100 in accordance with an example implementation of the present disclosure. As shown, the image capture system 100 includes one or more image capture devices (e.g., one or more cameras 102) and a computing device 104 communicatively coupled to the image capture devices. The cameras 102 are configured to capture images and per-pixel depth information in a field-of-view (FOV) of the cameras 102. As described below, the one or more cameras 102 may be integral with the computing device 104 in some implementations or the one or more cameras 102 may be external to the computing device 104 in other implementations. In an implementation, the cameras 102 may be depth cameras, such as Red-Green-Blue depth (RGB-D) cameras operable to capture depth frame image data representing one or more depth frame images and to capture color frame image data representing one or more color (RGB) frame images. In an embodiment, the cameras 102 may include, but are not limited to: a near infrared light configured to generate a near infrared light pattern onto the objects within the FOV, a depth frame image complementary-metal-oxide-semiconductor (CMOS) sensor device configured to measure the depth of each object within the FOV, and a color frame image CMOS camera device. For example, RGB-D cameras can identify various objects within the FOV of the cameras 102 and estimate the depth of the identified objects through various depth approximation techniques. For instance, the RGB-D cameras may transmit a structured light pattern in the near-infrared spectrum and utilize suitable parallax techniques to estimate the depth of the objects within the camera's 102 FOV in order to generate depth image data representing one or more depth frame images. Thus, a camera 102 captures data to allow for generation of a depth frame image representing at least partially objects within the camera's 102 FOV. The camera 102 may also be configured to capture color frame image data representing a color frame image at least partially representing objects within the camera's 102 FOV. For example, the depth image may include a two-dimensional (2-D) pixel area of the captured scene where each pixel in the 2-D pixel area may represent a depth value such as a length or distance (e.g., centimeters, millimeters, or the like of an object in the captured scene from the camera 102)

In an implementation, the camera 102 provides the ability to capture and map three-dimensional video imagery in addition to two-dimensional video imagery. For example, the camera 102 can capture two-dimensional data for a plurality of pixels that comprise the video image. These data values represent color values for the pixels (e.g., red, green, and blue [RGB] values for each pixel that represents the environment). Thus, objects captured by the cameras 102 can appear as two-dimensional objects via a monitor. As mentioned above, the cameras 102 can also capture depth data within the cameras' 102 FOV. Thus, the cameras 102 are configured to capture the x and y components (e.g., x and y values) of the environment within the FOV using RGB values (captured image data) for each pixel in the scene. However, the cameras 102 are configured to also capture the z-components of the environment, which represent the depth values (e.g., depth estimate data corresponding to the z-axis) within the environment.

The camera 102 furnishes the image data (captured image data, depth estimate data, etc.) to the computing device 104. In a specific implementation, the camera 102 may be configured to capture images representing environmental views within the FOV of the camera 102. For example, the camera 102 may capture image data (e.g., three-dimensional data) representing a bed and one or more objects within the FOV of the camera 102 with respect to an image plane of the camera 102.

The computing device 104 may be configured in a variety of ways. For example, the computing device 104 may be a server computing device, a desktop computing device, a laptop computing device, an embedded computing device, or the like. In some implementations, the camera 102 is external to the computing device 104. In other implementations, the camera 102 is integral with the computing device 104. As shown in FIG. 1A, the computing device 104 includes a processor 106 and a memory 108.

In some embodiments, the system 100 may include a plurality of computing devices 104 operating as a computer cluster 124, as illustrated in FIG. 1B. For example, each computing device 104 can comprise a cluster node 104*a-c*. Each cluster node 104*a-c* can include a respective processor 106 and memory 108. The computer cluster 124 can also include a shared memory (e.g., cluster memory 126) that is accessible by all cluster nodes 104*a-c* via the communication network 110.

The processor 106 provides processing functionality for the computing device 104 and may include any number of processors, micro-controllers, or other processing systems and resident or external memory for storing data and other information accessed or generated by the computing device 104. The processor 106 may execute one or more software programs (e.g., modules) that implement techniques described herein. For example, the processor 106, in conjunction with one or more modules as described herein, is configured to generate a depth mask (image) of the environment based upon the depth estimate data (e.g., z-component data) captured by the cameras 102. For example, one or more modules are configured to cause the processor 106 to continually monitor the depth value of at least substantially all of the pixels that represent the captured environment and stores the greatest (deepest) depth value associated with each pixel. For instance, the modules cause the processor 106 to continually monitor for a predetermined amount of time (e.g., a plurality of frames) the depth value of the pixels and store the deepest depth value measured during the time interval. Thus, the depth mask comprises an accumulation of depth values and each value represents the deepest depth value of a pixel measured over the time interval. The processor 106 can then be instructed to generate a point cloud based upon the depth mask that includes a set of point values that represent the captured environment.

The memory 108 is an example of tangible computer-readable media that provides storage functionality to store various data associated with the operation of the computing device 104, such as the software program and code segments mentioned above, or other data to instruct the processor 106 and other elements of the computing device 104 to perform the steps described herein. Although a single memory 108 is shown, a wide variety of types and combinations of memory may be employed. The memory 108 may be integral with the processor 106, stand-alone memory, or a combination of both. The memory may include, for example, removable and non-removable memory elements such as RAM, ROM, Flash (e.g., SD Card, mini-SD card, micro-SD Card), magnetic, optical, USB memory devices, and so forth. In some implementations, one or more of the types of memory 108 can comprise a cluster memory 126 that can be accessed by multiple computing devices 104 (i.e., a computer cluster 124) via the communication network 110, as illustrated in FIG. 1B.

The computing device 104 is communicatively coupled to the cameras 102 over a communication network 110 through a communication module 112 included in the computing device 104. The communication module 112 may be representative of a variety of communication components and functionality, including, but not limited to: one or more antennas; a browser; a transmitter and/or receiver; a wireless radio; data ports; software interfaces and drivers; networking interfaces; data processing components; and so forth.

The communication network 110 may comprise a variety of different types of networks and connections that are contemplated, including, but not limited to: the Internet; an intranet; a satellite network; a cellular network; a mobile data network; wired and/or wireless connections; and so forth.

Examples of wireless networks include, but are not limited to: networks configured for communications according to: one or more standard of the Institute of Electrical and Electronics Engineers (IEEE), such as 802.11 or 802.16 (Wi-Max) standards; Wi-Fi standards promulgated by the Wi-Fi Alliance; Bluetooth standards promulgated by the Bluetooth Special Interest Group; and so on. Wired communications are also contemplated such as through universal serial bus (USB), Ethernet, serial connections, and so forth.

The system 100 may include a display 114 to display information to a user of the computing device 104. In embodiments, the display 114 may comprise an LCD (Liquid Crystal Diode) display, a TFT (Thin Film Transistor) LCD display, an LEP (Light Emitting Polymer) or PLED (Polymer Light Emitting Diode) display, and so forth, configured to display text and/or graphical information such as a graphical user interface. The processor 106 is configured to request depth image data and color frame image data from the camera 102 (e.g., image capture device) and create an association between the depth image data and the color frame image data. In an implementation, the processor 106 may be configured to provide the associated data to the display 114 for display purposes.

As shown in FIG. 1A, the system 100 may include one or more input/output (I/O) devices 115 (e.g., a keypad, buttons, a wireless input device, a thumbwheel input device, a trackstick input device, a touchscreen, and so on). The I/O devices 115 may include one or more audio I/O devices, such as a microphone, speakers, and so on.

As shown in FIGS. 1A and 1B, the computing device 104 includes a patient monitoring module 116 which is storable in the memory 108 and/or cluster memory 126. The patient monitoring module 116 is executable by the processor 106. The patient monitoring module 116 is representative of functionality to monitor a medical care environment. For example, the module 116 is representative of functionality to monitor one or more objects (e.g., subjects) within a medical environment. For instance, the objects may be patients, medical personnel, medical equipment, and so forth. In a specific implementation, the module 116 represents functionality to monitor a patient when the patient is positioned proximal or within a bed (or chair). While the present disclosure illustrates a patient in or proximal to a bed, it is understood that the system 100 may utilize the techniques disclosed within to monitor a patient in or proximal to a chair. The module 116 is configured to determine whether the patient is still in the bed (or the chair) and the approximate orientation (e.g., positioning) of the patient within the bed (or the chair). The system 100 may be utilized to monitor a patient within a medical care environment, such as a hospital environment, a home environment, or the like. The module 116 also represents functionality to monitor medical personnel within the medical environment (e.g., monitor how long the medical personnel is within the FOV). The module 116 may monitor the objects within the medical environment through a variety of techniques, which are described in greater detail below.

The module 116 is configured to cause the processor 106 to determine a depth value associated with each pixel (e.g., each pixel has a corresponding value that represents the approximate depth from the camera 102 to the detected object). In an implementation, the module 116 is configured to cause the processor 106 to determine a center of mass of a detected object positioned above the bed model. For example, the module 116 may initially cause the processor 106 to determine a bed model 202 representing a bed within the FOV of the camera 102 (e.g., determine the depth of the bed with no objects on or over the bed). Thus, the pixels associated with the bed are identified (i.e., define a bed model) and an associated distance is determined for the identified bed.

In implementations, the module 116 can cause the processor 106 to implement one or more object location modules to identify a bed footprint, which can be used to determine a bed model. For example, the processor 106 can break the floor into a grid of squares. The processor 106 can then create a Boolean array, with one entry for each grid square. For example, the processor 106 can identify as true squares which are occupied (i.e., contain at least one point or pixel), and can identify as false squares which are unoccupied (i.e., contain no points or pixels). In implementations, the processor can also identify as false squares for which the column of space above the square is not visible. This removes points that are located outside the field of view of the camera and/or not visible (i.e., behind a wall) from consideration as part of the bed footprint. The processor 106 can then identify maximum rectangles that contain only true squares. Once the maximum rectangles are identified, the processor 106 can filter the maximum rectangles based on predetermined parameters to identify rectangles that are large enough to contain a bed. For example, the processor 106 can record whether or not the column above each square might have an occupied region of a specified thickness within a specified range of heights that correspond to a bed. In an example implementation, the processor 106 can identify squares in which the column above the square has an occupied region thickness of at least approximately 150 millimeters and a range of heights between approximately 100 millimeters and approximately 1800 millimeters. In some example embodiments, the processor 106 identifies squares with an occupied thickness of at least approximately 225 millimeters. Increasing occupied thickness threshold can increase the speed of the filtering process and can reduce the number of possible bed footprints. The processor 106 can also filter based on the continuity of the bed footprint by identifying only squares where the occupied section overlaps neighboring columns by at least approximately 225 millimeters. A stronger overlap requirement (e.g. about approximately 305 millimeters) can be utilized to further filter the maximum rectangles. Any of the filtered rectangles are possibly part of the bed footprint.

The processor 106 can utilize dynamic programming, automatic parallelization, and/or can implement one or more mathematical morphology (e.g., erosion, dilation, etc.) techniques to enhance the speed and/or accuracy of identifying maximal rectangles, and to reduce noise. For example, the array of maximal rectangles can be eroded by the minimum bed width/2 and then dilated by the maximum bed width/2. The dilated image is then intersected with the original array. Increasingly aggressive erode and dilate sequences can be performed in areas with points that are easily misclassified (e.g., points near the camera). In some implementations, the processor 106 can use a subsampled frame (e.g., 50% resolution image, 75% resolution image, etc.) to further reduce the number of points utilized in calculations.

The module 116 can cause the processor 106 to implement one or more object location modules to reduce the number of maximal rectangles. For example, a similarity metric (m) can be used to identify similar rectangles. In example implementations, the processor 106 can identify where a first rectangle (R1) is contained within a second rectangle (R2) by implementing the similarity metric m(R1, R2)=Area(R1 intersect R2)/min(Area(R1), Area(R2)). The processor 106 can build a reduced list of maximal rectangles by starting with R1 and comparing to R2. If the similarity metric (m) exceeds a preselected threshold, the processor 106 retains the larger of the two rectangles. The processor 106 repeats this process to compare all rectangles and identify the maximal rectangles most likely to represent the bed footprint. The processor 106 can employ one or more techniques (e.g., dynamic programming, automatic parallelization, etc.) to improve the speed and/or accuracy of the similarity computations.

In implementations, the Boolean array of the bed footprint can be adjusted to approximate different bed angles. For example, the processor 106 can determine axis parallel maximum rectangles for one orientation of the array. The array can then be rotated to test for preselected bed angles in a conservative way that does not lose possible pixels.

In some implementations, the processor 106 can incorporate user input into the one or more object location modules to more quickly and/or accurately identify the bed footprint. For example, a user can use the I/O devices 115 to identify points that are part of the bed and points that are not part of the bed. Points that are part of the bed are identified as true and points that are not part of the bed are identified as false. At each rotation step, the processor 106 can restrict the Boolean array to the union of the axis parallel rectangles of a size equal to the maximum dimensions containing the selected points. After identifying a maximal rectangle, the processor 106 confirms that all selected points are within it. In implementations, the user can also identify points that are above the bed surface. In some implementations, the user can reverse mistaken or contradictory point identifications. In other implementations, the processor 106 can be configured to correct mistaken or contradictory point identifications.

After a reduced set of maximum rectangles is identified by a module and/or user input, the processor 106 can implement one or more object location modules to identify which maximum rectangle represents the bed footprint. For example, the processor 106 can find the maximum number of identified pixels contained in a rectangle that could be the bed footprint. The processor 106 can iterate over reduced set of maximum rectangles to determine the maximum number of identified pixels (S) that are contained in a maximal rectangle that could represent the bed footprint. The processor 106 can then iterate over all identified maximal rectangles (R). The processor 106 then determines the minimal area rectangle parallel to and contained in R that contains S to locate potential bed footprints.

The module 116 can cause the processor 106 to model the bed from the identified potential bed footprints. The processor 106 can implement one or more object identification modules to model the bed from the potential bed footprints. For example, the processor 106 can employ one or more optimization modules such as gradient ascent, gradient descent, and so forth. The processor 106 can start from an identified potential bed footprint and employ a gradient ascent to scan locally along the length and height of the bed plane (bed plane Z and Y coordinates) to identify a footboard fitness. The footboard fitness is the sum of penalties for each point in the point cloud near the foot of the bed, where the penalty is proportional to distance to the potential bed footprint, the penalty is light for points above or in front of the bed footprint, and the penalty is heavy for points behind and below the bed footprint. The processor 106 can use gradient ascent to optimize fitness for a given Y value in the Z coordinate, and then iteratively optimize for all Y values. The processor 106 can repeat this process for all potential bed footprints to determine the best footboard model at each location. The number of potential bed footprints modeled is significant in relation to the speed and accuracy of the modeling process. For example, a number must be selected that is both reasonably fast and reasonably accurate. In an example embodiment, approximately 1000 to approximately 1200 potential bed footprint footboards can be modeled.

The module 116 can also cause the processor 106 to model the midsection of the bed. The processor 106 can also employ a gradient ascent based on one or more parameters (e.g., length of the portion of mattress below the bend point, bed angle, etc.) to scan locally along the midpoint of the bed. The gradient ascent bends the bed angle upwards to maximize fitness. Midpoint fitness is the sum of penalties for points near the midpoint, where the penalty is proportional to distance from the potential bed footprint, the penalty is light for points above the bed footprint, and the penalty is heavy for points behind the bed footprint. The processor 106 can then employ a gradient ascent to optimize mattress length and/or angle. In some implementations, the processor 106 can model the midsection of the bed at all potential bed footprint locations. In other implementations, the processor 106 can be configured to only model the midsection of potential bed footprints with a footboard fitness above a selected threshold. For example, the processor can model the midsection at the locations with footboard fitness in the 50$^{th}$ percentile. Modeling the midsection for only a portion of footboards can increase modeling speed.

The processor 106 can use the data from the gradient ascent modules to produce a model bed. In some implementations, the processor 106 can produce a model bed for all modeled midsections. In other implementations, the processor 106 can be configured to only produce a model bed where the midsection fitness is above a selected threshold. Fully modeling only a portion of midsections can increase modeling speed. The model bed can include a width, length, height of ground, mid-bed point, mid-bed angle, and/or mattress thickness. The processor 106 can repeat this process to determine the best bed model at each location. The module 116 can then cause the processor 106 to identify the model bed with the highest fitness. Once the optimal bed model is identified, the module 116 can cause the processor 106 to determine one or more variables about the bed model (e.g., footprint, axes, coordinates, bend points, bed planes, etc.).

The module 116 can cause the processor 106 to continually evaluate bed model fitness to reduce errors (e.g., obstructions, intervening objects, extreme camera angles, limited bed visibility, etc.). The processor 106 can employ one or more modules to evaluate bed model fitness. For example, the processor 106 can iterate a fitness function at preselected intervals, where the penalty is proportional to distance from the bed model, the penalty is light for points in front of the bed model, and the penalty is heavy for points behind the bed model. If the model fitness fails to meet an accuracy threshold for a specified period of time, the module 116 can cause the processor 106 to re-execute the bed-location modules. In some implementations, the processor 106 can perform a jiggle function to adjust the bed model horizontally and/or adjust the bed model angle. The processor 106 can implement the jiggle function when the fitness function determines that model fitness is poor. In some implementations, the module 116 can cause the processor 106 to stop the iteration of the fitness function and/or the jiggle function once a fixed location is identified. For example, the processor 106 can stop iterating the fitness function when the fitness difference between iterations is less than 1.

In one or more implementations, the system 100 may utilize suitable machine learning techniques to identify bed location. For example, the processor 106 can use bed finding data about the classification of pixels being in the bed or not to select the most likely potential bed footprints to model. The processor 106 can then utilize the fitness of the bed models to determine if additional locations need to be modeled. For example, if a model bed with high fitness is identified, the processor 106 does not model the remaining potential bed footprints. If a model bed with average fitness is identified, the processor can model a portion of the remaining potential bed footprints. The system 100 may also utilize bed finding data to sort maximal rectangles, cull potential bed locations, and so forth. For example, the processor 106 can use bed finding data to determine a regression line to streamline the identification of possible bed locations. The processor 106 can also utilize one or more morphology techniques (e.g., erosion, dilation, etc.) to alter the bed finding data. In some implementations, the system 100 may utilize bed location data to build potential bed footprints, rather than finding the potential bed footprint locations.

It is to be understood that the processor 106 can utilize one or more techniques to enhance the speed and/or accuracy of bed location and/or bed modeling. Such techniques can include, but are not limited to dynamic programming, automatic parallelization, morphology, data binning, and so forth.

When an object is positioned within in the bed, the module 116 is configured to cause the processor 106 to continually monitor the depth values associated with at least substantially all of the pixels within the defined bed model. Thus, the processor 106 is configured to process the depth image to determine one or more targets (e.g., users, patients, bed, etc.) are within the captured scene. For instance, the processor 106 may be instructed to group together the pixels of the depth image that share a similar distance.

It is understood that the system 100 may utilize the techniques disclosed within to monitor a patient in or proximal to a variety of seating platforms including, but not necessarily limited to a wheelchair, a toilet, a bench, and so forth. For example, the module 116 can be configured to determine whether the patient is still in a wheelchair and the approximate orientation (e.g., positioning) of the patient within the wheelchair. The module 116 may initially cause the processor 106 to determine a wheelchair plane representing a wheelchair within the FOV of the camera 102 (e.g. determine the depth of the wheelchair with no objects on or over the wheelchair). Thus, the pixels associated with the wheelchair are identified (i.e., define a wheelchair plane) and an associated distance is determined for the identified wheelchair. When an object (e.g., patient) is positioned within in the wheelchair, the module 116 is configured to cause the processor 106 to continually monitor the depth values associated with at least substantially all of the pixels within the defined wheelchair plane. Thus, the processor 106 is configured to process the depth image to determine one or more targets (e.g., users, patients, wheelchair, etc.) are within the captured scene. For instance, the processor 106 may be instructed to group together the pixels of the depth image that share a similar distance. The system 100 may be utilized to monitor a patient within a medical care environment, such as a hospital environment, a home environment, or the like. The module 116 may monitor the objects within the medical environment through a variety of techniques, which are described in greater detail below.

Figure 2A:
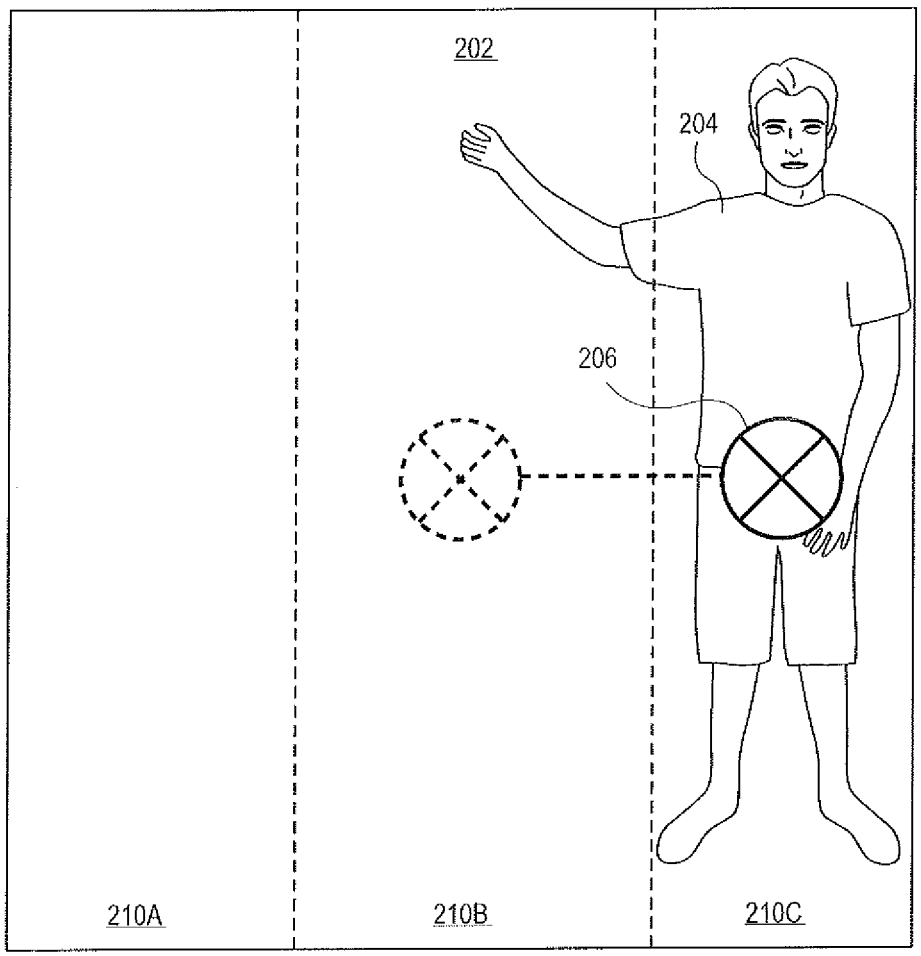
FIGS. 2A through 2Z are diagrammatic illustrations depicting various techniques for monitoring an object within a physical environment according to the image capture system shown in FIGS. 1A and 1B.

As shown in FIG. 2A, at least a portion of the pixels proximal to the bed may represent an object 204 (e.g., a patient) within the bed, and the module 116 causes the processor 106 to monitor the depth values of the pixels representing the object 204 as these pixels have a depth value that is less than the depth value of the pixels defining the top plane 202 of the bed model (e.g., the object is nearer to the camera 102 as compared to the top plane 202 of the bed, the object is above the bed model). The module 116 causes the processor 106 to identify a group of pixels having depth values (e.g., z-values) indicating a closer distance to the camera 102 as compared to the pixels defining the top plane 202. For example, the processor 106 may incorporate a shortest-distance technique for identifying these pixels. The module 116 causes the processor 106 to determine a center of mass 206 based upon the identified pixels (pixels having z-value closer to the camera 102 as compared to the pixels representing the bed model). The module 116 is configured to instruct the processor 106 to divide the top plane 202 into discrete portions. For example, the module 116 may be configured to divide the top plane 202 into three (3) discrete portions 210A, 210B, 210C (i.e., 2 side portions and 1 middle portion). The module 116 then instructs the processor 106 to determine which portion more than half of the mass (approximated), or center of mass 206, of the object 204 is located within. If at least approximately half of the mass is determined to be within a side portion of the top plane 202, the processor 106 determines that the patient is positioned at an edge of the bed. Based upon this determination, the module 116 causes the issuance of an alert (e.g., electronic communication such as a SMS message, an e-mail message, or the like) to detect, or to indicate, that the patient's position within the bed.

Figure 2B:
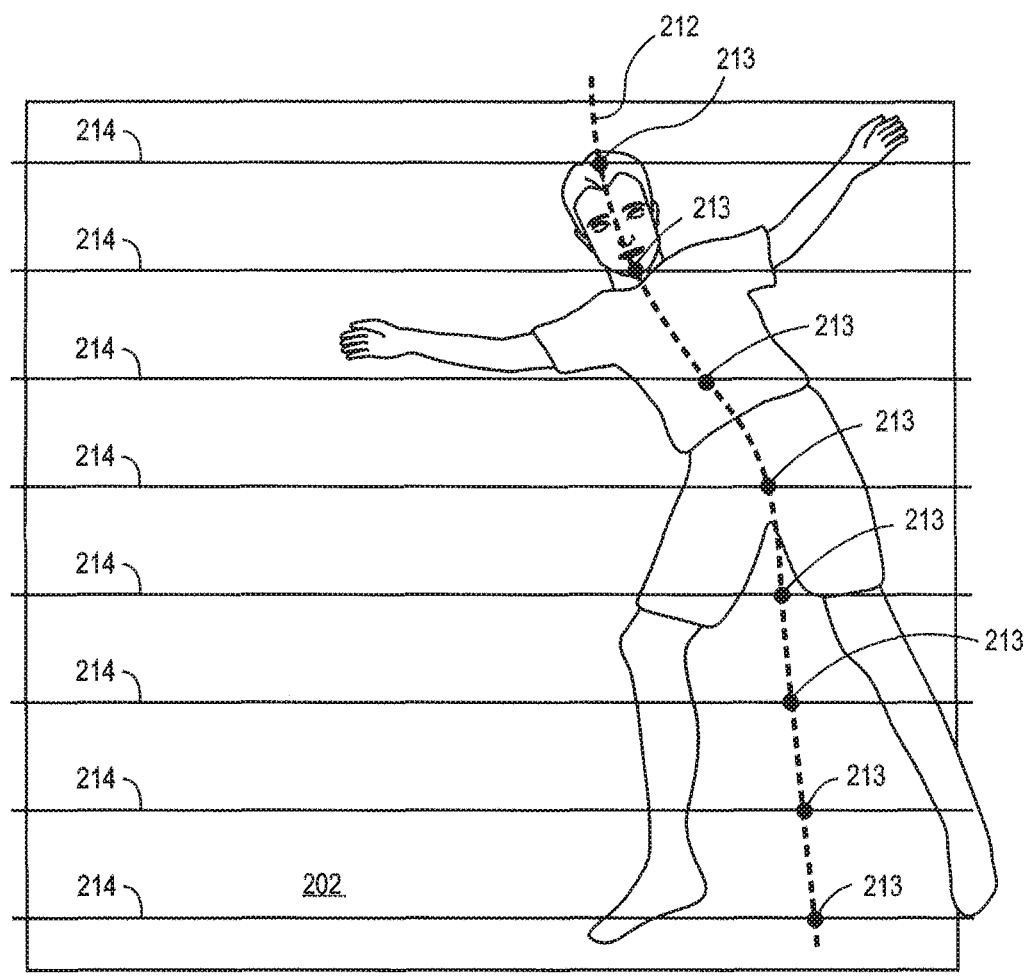

In another implementation, the module 116 may utilize center of mass scan-line techniques, or other suitable techniques, to determine how the patient is positioned within the bed (see FIG. 2B). In an implementation, the module 116 is configured to generate a curve 212 representing an orientation of the object 204 (e.g., patient's body) within the bed. If the bottom portion of the curve 212 moves to the right with respect to a defined center line and then moves back to the center line, the module 116 determines that the patient is positioned on the patient's left side with his or her knees tucked. The module 116 may cause the processor 106 to identify a plurality (e.g., a set) of points having a depth characteristic above the top plane 202 of the bed model. In this implementation, the processor 106 identifies a plurality of points from a first side (e.g., the "top" side or the side of the bed that the patient's head is proximally located) to a second side (e.g., the "bottom" side of the bed or the side of the bed that the patient's feet (or foot, legs, etc.) are proximally located. For example, the module 116 may cause the processor 106 to compute by way of a suitable scan line technique of one or more of the identified points (e.g., body points) representing the patient. For instance, the processor 106 may utilize mean shifted processes or center of mass processes to identify a plurality of points (pixels) representing a portion of the object 204 (e.g., patient). Thus, the processor 106 can utilize a subset of the points 213 to generate one or more lines 214 (or "trace" a line from the first side of the bed to the second side of the bed) utilizing one or more statistically noise-resistance techniques to determine a general orientation of the patient's body within the bed. The points utilized when generating the lines 214 may be weighted by various criteria so as to provide greater importance to a first pixel as compared to a second pixel. For example, pixels that are determined to be higher above the top plane 202 as compared to pixels that represent portions of the space that are lower than the bed may be given a greater weight. Thus, the module 116 is configured to cause the lines 214 to represent (move towards or gravitate towards) the segmented points that are higher than the bed.

Figure 2C:
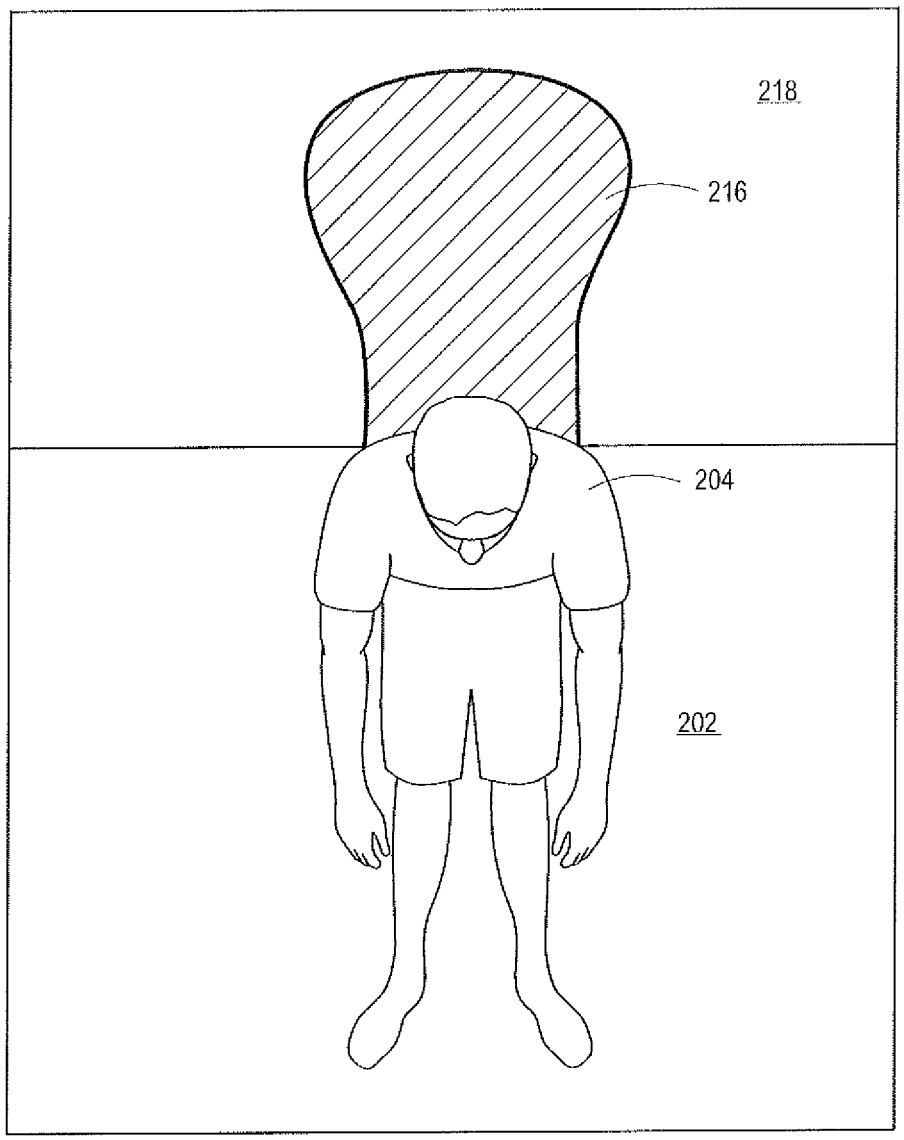

As shown in FIG. 2C, the module 116 may cause the processor 106 to identify whether an object 204 is sitting in the bed. For example, when an object 204, such as a patient, is sitting up in bed, the processor 106 may identify one or more regions 216 identified as having zero pixels within a region 218 of the top plane 202 (e.g., processor 106 determines there is no depth data associated with the region 218). The processor 106 may also determine that the object 204 is sitting in bed based upon the processor 106 determining that pixels having a depth value classified as representing the body (e.g., pixels having a certain height above the bed) are not identified within the region 218 (e.g., top of the bed). The processor 106 may also determine that the object 204 is sitting based upon an determination that a threshold of pixels classified as representing the body are proximate (e.g., adjacent) to the region 216.

Figure 2D:
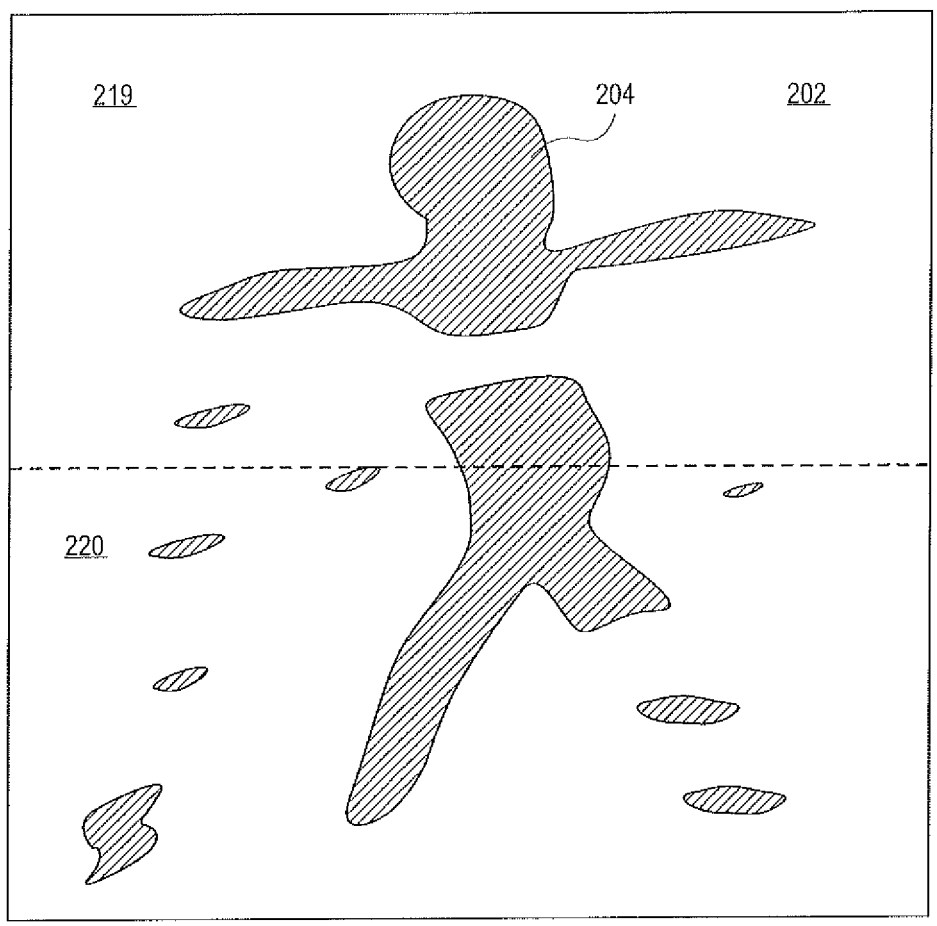
Figure 2E:
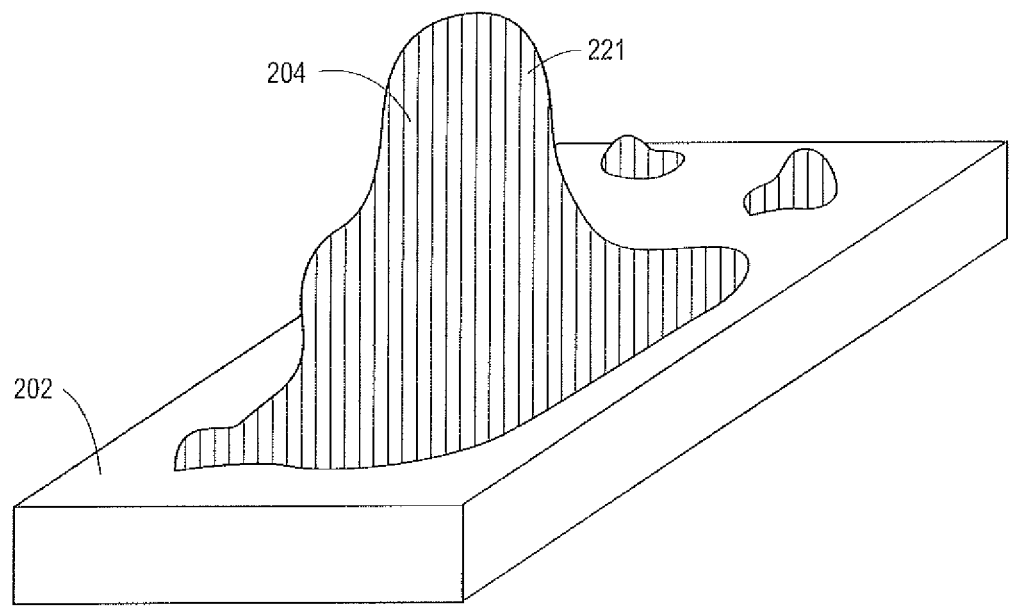

In another implementation, the module 116 may cause the identification, or positioning, of the object 204 through a determination of a relatively uniform distribution of body pixels from the first region 219 of the top plane 202 to the second region 220 of the top plane 202 (see FIG. 2D). In another implementation, as shown in FIG. 2E, the processor 106 may identify a mass (e.g., subset) 221 of pixels having depth values above the bed model 226 (e.g., proximal to the camera 102 as compared to the pixels representing the top plane 202). In an implementation, the subset of pixels may represent a volume or mass above the top plane 202 that is indicative of the object 204 sitting up. Based upon the subset 221 of the identified pixels, the processor 106 can be instructed by the module 116 to integrate over the subset of pixels to determine an approximate volume between the pixels identified as above the bed and the bed itself. Additionally, one or more clustering techniques may be utilized such that the system 100 is tolerant of other objects located within the bed (e.g., pixels representing other objects having depth values above the top plane). Thus, a center of mass technique may be utilized to determine whether a center of mass (e.g., pixels) is a certain height above the bed, which is indicative of the patient sitting up.

Figure 2F:
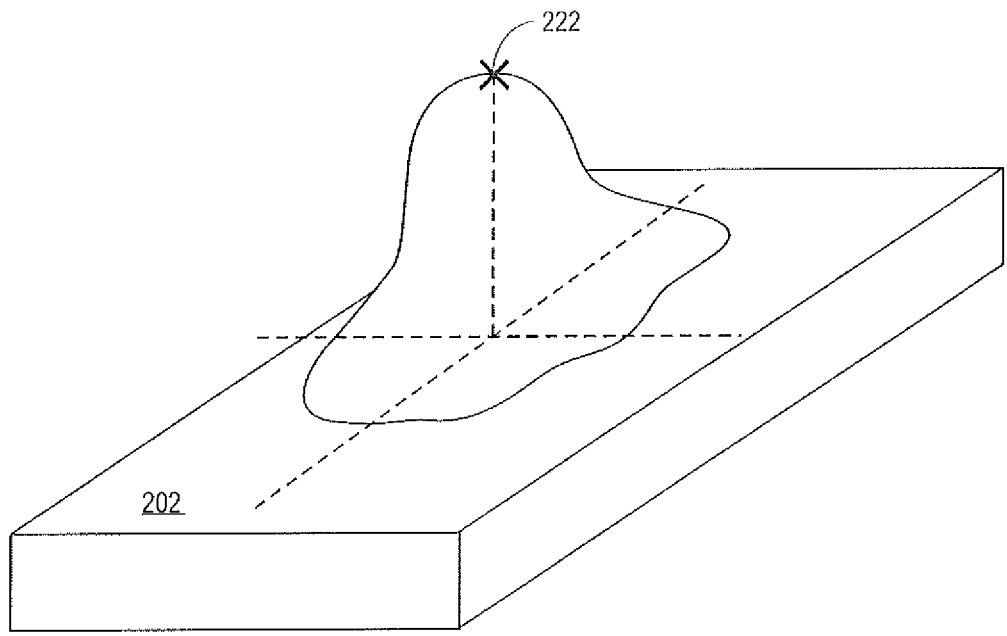

In yet another implementation, the module 116 may cause the processor 106 to analyze and determine which pixel represents the point 222 most distant from the bed model 226 (e.g., x, y, and z coordinates that, when converted into a distance from pixels representing the top plane 202, yield a value that is greater than the value calculated for the other pixels identified as representing a discrete object over the bed with respect to pixels representing the top plane). In this implementation, the most distant pixel may indicate a height (maximum height) of the object above the bed, which may be indicative that the object 204 is sitting up in bed (see FIG. 2F).

Figure 2G:
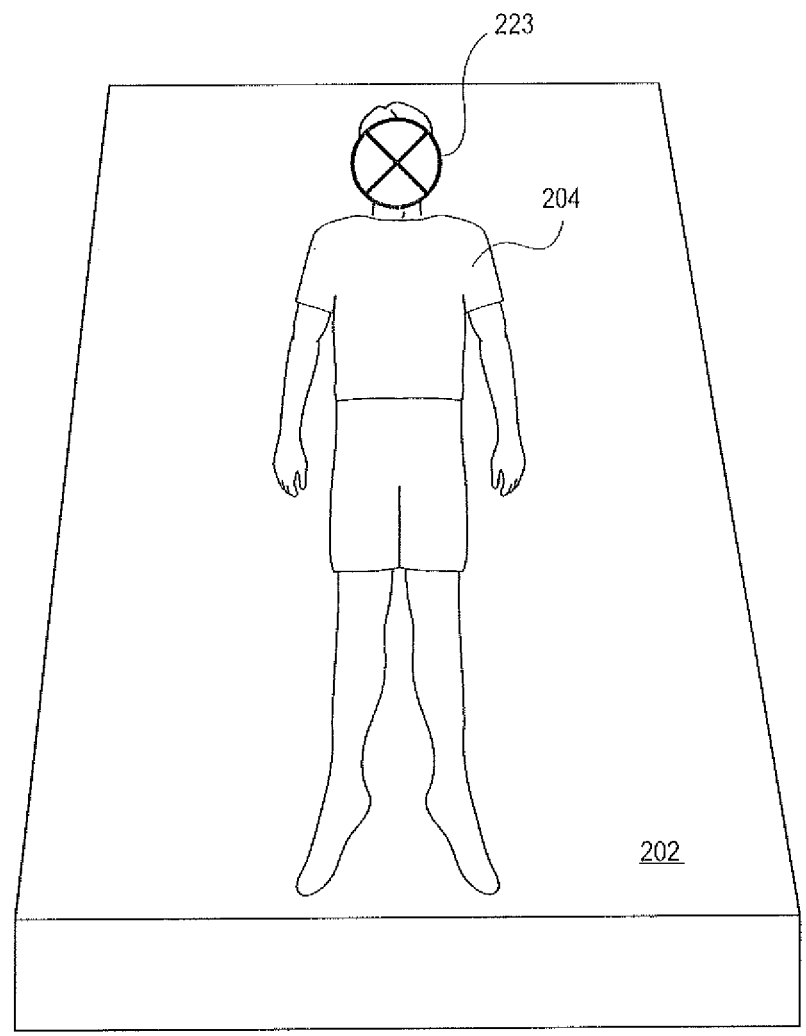

In yet another implementation, as shown in FIG. 2G, the system 100 may incorporate facial detection techniques to determine a body orientation of the patient. In one or more implementations, the system 100, such as the module 116 and the processor 106, may incorporate suitable machine-learning techniques to assist in the detection of pixels 223 representing the face of the patient. Thus, the processor 106, in conjunction with the module 116, can increasingly (e.g., higher accuracy or confidence intervals) determine the body orientation through the classification of individual body parts based upon the facial recognition (e.g., determine pixels representing individual body parts based upon the pixels identified as representing the face). It is contemplated that the system 100 may also utilize the orientation of the bed to indicate, or aid, in determining the body orientation and the body position of the object 204.

Figure 2H:
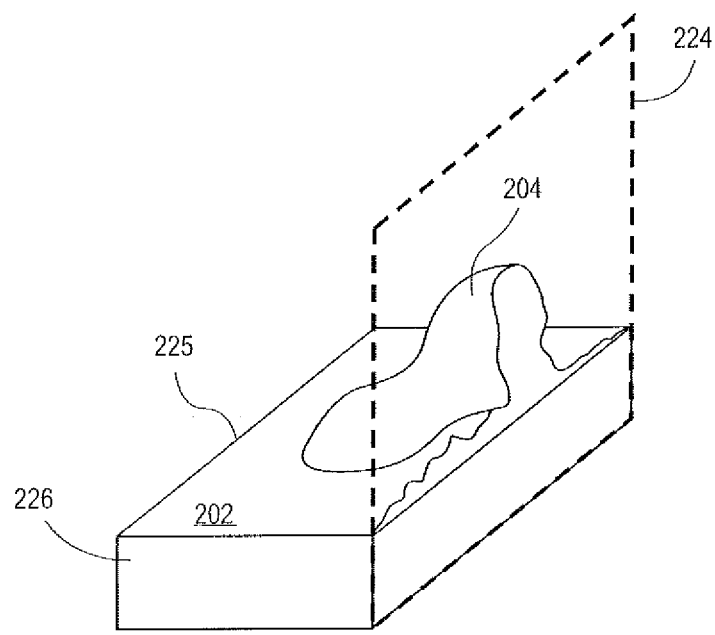

In yet another implementation, the system 100 may identify patients getting out of or getting into the bed. For example, as shown in FIG. 2H, the module 116 causes the processor 106 to define a plane 224 at an edge 225 of the bed model 226 such that the processor 106 can identify an object 204 (e.g., a grouping of pixels) that is within the FOV of the camera 102 and are over the bed model 226. More specifically, the processor 106 can identify subsets of pixels (a subset of pixels having a predefined number of pixels within the subset) that change (e.g., pixel transitions to representing another object, such as a wall, the bed model 226, etc.) within a predefined number of frames (as well as pixels that are connected to the bed [e.g., grouping of pixels having a subset of pixels adjacent to the pixels representing the bed]) to indicate whether the object 204 has transitioned out of or transitioned into the bed model 226. By identifying subsets of pixels proximate to the bed model 226, the processor 106 can remove people that are reaching over the bed model 226 or objects 204 that are within the bed model 226 or positioned within the bed model 226. For example, the module 116 is configured to cause the processor 106 to determine that the patient is putting an extremity outside of the bed model 226 by approximating, utilizing a noise tolerant method, the surface area of objects not above the top plane 202 of the bed model 226. In another example, the module 116 causes the processor 106 to detect an arm reaching out of the bed model 226 based upon an identification of a subset of pixels representing the arm that are above the top plane 202. If the module 116 detects pixels above a predetermined threshold, the module 116 determines that the patient is moving a body part outside of the bed.

Figure 2I:
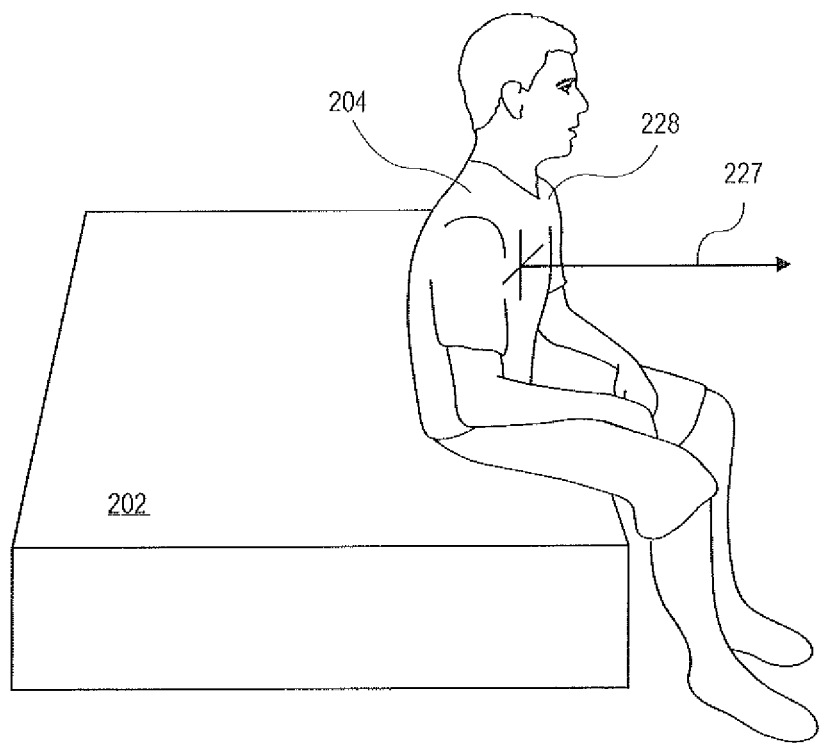

In yet another implementation, the system 100 is configured to analyze one or more component vectors (shown as vector 227) belonging to a subset 228 (e.g., mass) of pixels representing the object 204 to at least partially assist in determining the orientation of the subset of pixels (see FIG. 2I). For example, the module 116 is configured to determine one or more component vectors associated to (e.g., belonging to) a portion the subset 228 of pixels. Based upon the determined component vectors, the module 116 is configured to cause the processor 106 to determine an orientation of the object 204 represented by the subset 228 of pixels. In each of the implementations described above, the module 116 may cause the issuance (e.g., generate and transmit) of an electronic communication indicating the presence of an object (patient) within the bed, the object's position within the bed, or whether the object was not determined to be within the bed. In some implementations, the system 100 is configured to interface with third party systems that may issue alerts to medical personnel based upon the electronic communication.

In another implementation of the present disclosure, the patient monitoring module 116 includes a fusion engine 118 for determining a state (e.g., position of the human relative to the bed model 226, the side on which the patient is lying, etc.) associated with the human. The fusion engine 118 may implement one or more modules corresponding to sensor fusion techniques that map one or more input signals representing a possible state of the patient to a probability distribution (e.g., a set of weighted parameters) associated with possible output states (e.g., determinations of the state of the patient). In a specific implementation of the present disclosure, the fusion engine 118 may implement a Hidden Markov model for assigning weighted parameters to signals associated with the captured environment (e.g., data signals indicating whether there is motion within the captured environment, signals representing a body part, data signals extracted from the captured image data, etc.). More specifically, the fusion engine 118 is configured to determine and to apply weighted parameters to techniques for capturing data associated with one or more pixels. For example, the fusion engine 118 applies a first weighted parameter to data corresponding to a first technique (e.g., a first signal) and applies a second weighted parameter to data corresponding to a second technique. In this example, the first and the second weighted parameters may be the same or may be different. For instance, the weighted parameter may be applied based upon the body portion, the orientation of the body part, the technique utilized, or the like. Based upon the weighted parameters, the module 116 causes the processor 106 to determine a state of the patient (e.g., the side on which the patient is positioned, patient is positioned on the floor, patient is sitting in bed, etc.).

One or more characteristics 120 associated with the patient may be furnished to the system 100 by a user, such as a caregiver (e.g., medical personnel). The characteristics 120 may include, but are not limited to: age, gender, weight, body type/dimensions, diagnoses, time of day, able-bodied, gait characteristics, mental status, physical restrictions (e.g., missing limbs), facial deformalities, sleeping abnormalities, angle of bed, dimensions of bed, additional equipment in room (e.g., standing IV), fall risk score (e.g., fall risk as determined by the Morse Fall Scale, STRATIFY Scale, Johns Hopkins Scale, Hendrich II Fall Risk Model, etc.), patient schedule, call light signal, bed alarm signal, alarm history, fall risk score, medication records, caregiver has moved the patient, patient ethnicity and/or skin tone, bed characteristics (e.g., pillow/sheet colors/patterns), patient repositioning protocol, and/or patient history of side lying activity. In one or more implementations, the system 100 may utilize suitable machine learning techniques to identify (e.g., "learn") one or more characteristics 120 of the patient. For example, the system 100 may identify one or more characteristics 120 of the patient while monitoring the patient over a time period (e.g., determine which side the patient is positioned, determine a tendency of the patient at discrete time periods, determine recent activity level, etc.).

In some implementations, one or more caregiver characteristics 122 may be furnished to the system 100 by the user, such as a caregiver (e.g., medical personnel). The caregiver characteristics 122 may include, but are not limited to: caregiver schedules (e.g., hourly rounding schedules, number of caregivers on staff, shift time changes, etc.), average response time (e.g., average time it takes for a caregiver to see and respond to an electronic communication issued by the system 100, etc.), patient medication schedule (e.g., medication names or types and historical and future administration schedules), minimum patient repositioning requirements (e.g., every two hours for bed-bound patients and every 15 minutes for chair-bound patients), and caregiver location. In one or more implementations, the system 100 may utilize suitable machine learning techniques to identify (e.g., "learn") one or more of the caregiver characteristics 122. For example, the system 100 may identify the one or more caregiver characteristics 122 by monitoring the caregiver over a period of time (e.g., determine average call light response time, determine how frequently the nurse enters the patient's room, etc.).

In one or more implementations, the one or more characteristics 120 and/or the one or more caregiver characteristics 122 may be furnished to the system 100 by an external system (e.g., nurse call system, electron health record system, electronic medical record system, Admission-Discharge-Transfer system, nurse scheduling system, etc.).

In one or more implementations, the system 100 may use the one or more characteristics 120 and/or the one or more caregiver characteristics 122 to adjust sensitivity and behavior of the system 100, as described herein.

Figure 2J:
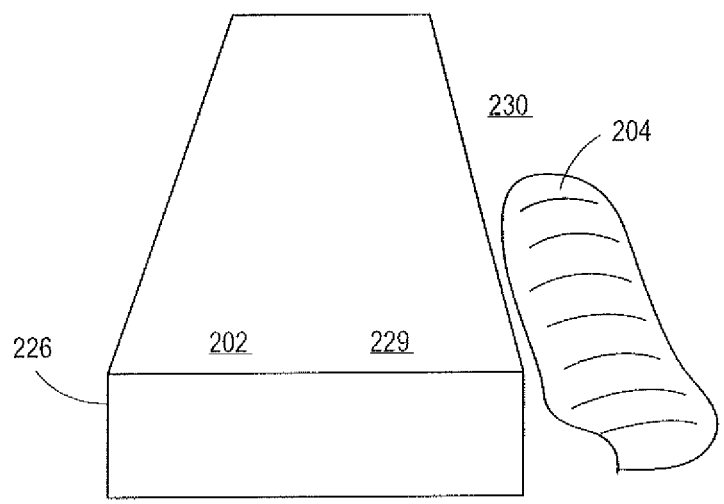

As described in greater detail below and with respect to FIGS. 2J to 2Z, the system 100 is configured to utilize various processing techniques to identify zero or more pixels (or subsets of pixels) representing a body part of an object 204 or pixels associated with a body part (e.g., blanket covering the body, etc.). Each of the processing techniques described below represent a distinct processing technique for identifying a state of the patient (e.g., orientation of the patient within the bed) and may be utilized simultaneously to determine a state of the object 204 (e.g., described hereinafter as patient 204). For example, a first technique (e.g., a first signal) may be utilized to identify one or more pixels representing a body part, and a second technique may be utilized to identify one or more pixels representing another (or the same) body part. The processor 106 utilizes the fusion engine 118 to apply a weighted parameter to each data set associated with each "signal" (e.g., the data associated with the pixels identified through the specified technique). As described above, the fusion engine 118 may utilize a suitable model, such as a Hidden Markov model, to apply the weighted parameters. However, it is understood other suitable models may be utilized. Based upon the weight parameters associated with each data set, the processor 106 determines a state of the patient. In the techniques described above, multiple cameras 102 may be utilized through the environment to provide additional views, or angles, of the environment. In some implementations, the system 100 may apply skeletonization techniques to identified masses to identify movement of the mass within the environment. In some of the implementations described herein, RANSAC techniques, or other geometric shape matching and modeling, may be utilized to identify pixels representing the bed, floor, or other objects within the scene (e.g., for point subtraction). For example, these techniques may be utilized to identify pixels representing rails associated with the bed for template matching, which is described herein.

In yet another implementation, the system 100 is configured to determine whether an object 204 is positioned on the floor (i.e., the patient fell from his or her bed). The module 116 is configured to utilize background subtraction methods to locate objects 204 that are outside of the bed model 226. Background subtraction techniques include keeping track of a maximum depth of at least substantially every pixel location (see FIG. 2J). Based upon the maximum depth value, a pixel having a depth value closer than the maximum depth value represents a foreground (represented as region 229, and pixels having a depth value at or below the maximum depth value represents background (represented as region 230). For example, the processor 106 is configured to determine pixels that represent the bed model 226 with respect to other objects within the field of view of the camera 102. The surface area of the objects identified as outside of the bed model 226 are estimated. The processor 106 determines the object 204 to be a human when the estimation is greater than a defined threshold of pixels (e.g., a subset of pixels is greater than a defined threshold of pixels). The module 116 is configured to instruct the processor 106 to differentiate between a standing person and a person lying down based upon the percentage of pixels representing the object 204 (based upon the surface area) classified as above the bed model 226 as compared to the percentage of pixels of the object 204 classified as below the bed model 226. For example, if the percentage of the pixels representing object 204 detected below the bed model 226 is above a defined threshold (e.g., greater than forty percent, greater than fifty percent, etc.), the module 116 instructs the processor 106 to determine that the person is lying down within the FOV of the camera 102. Thus, the processor 106 is configured to identify a subset of pixels representing a mass proximal to the subset of pixels representing the floor that were not proximal to the floor pixels in previous frames. In this implementation, the module 116 determines that the patient is on the floor when the subset of pixels representing the mass is proximal to the subset of pixels representing the floor that were not proximal to the floor pixels in previous frames.

Figure 2K:
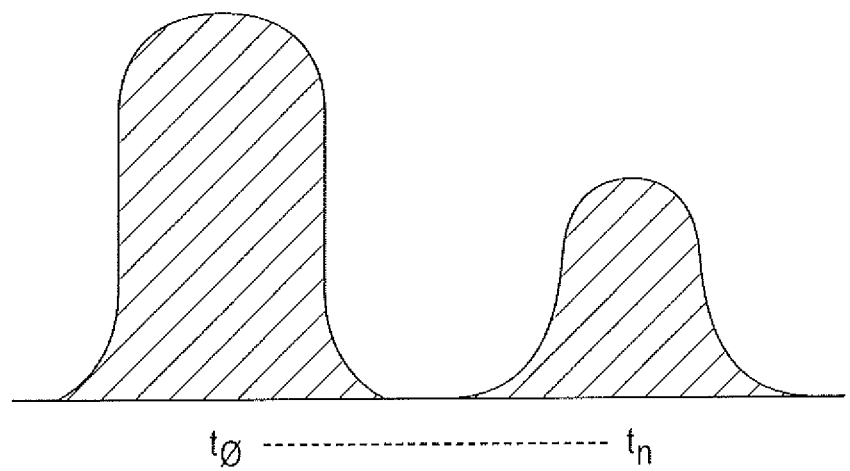

In another example, as shown in FIG. 2K, the module 116 is configured to determine a movement of the object 204 within the bed model 226 to determine if the object 204 has changed positions. For example, the module 116 is configured to cause the processor 106 to approximate a total change in volume of the detected pixels representing the object 204 (e.g., patient) in the bed within one image frame to the next image frame (e.g., the change in volume of pixels from $t_0$ to TN). In some implementations, the processor 106 can approximate the total change in volume of detected pixels between the bed portions. If the total change in volume of the patient within a defined period of time (e.g., a predetermined number of image frames) is below a defined threshold, the processor 106 can determine that the patient has not been repositioned. The module 116 is then configured to cause the processor to issue an alert indicating that the patient requires repositioning. If the total change in volume of the object is above a defined threshold, the module 116 is configured to cause the processor 106 to issue an alert indicating that the patient has been repositioned.

In another implement implementation, a machine-learned head tracking process is used to monitor the center position of the patient's head over a sequence of image frames. If the tracked position of the head fails to move over a predetermined amount of time by a predetermined distance (based on a coordinate whose origin is based upon the bed) then the probability that the patient may need to be turned increases. Thus, the module 116 is configured to cause the processor 106 to identify a center position of a head and monitor the center position of the head (e.g., pixels representing the center position of the head) through a plurality of image frames. If the processor 106 determines that the center position of the head has not transitioned over a predetermined distance within a predetermined amount of time, the processor 106 indicates that the patient should be turned.

In another implementation a machine-learned process (e.g., a trained decision tree) identifies a probability that a patient is lying on their side and on which side they may be laying. The machine learned process identifies and tracks key body parts such as shoulders and legs/arms (e.g., pixels that represent the key body parts). By monitoring the output of this sensor over a period of time, the processor 106 can determine whether a patient has changed sides at all, and if not, heighten the probability the patient may need to be turned. In another implementation, the process identifies one of several general shapes of the patient lying in bed (e.g., legs spread apart, legs together, arms raised above head, arms folded on chest) and if this sensor does not change after a period of time, heighten the probability the patient may need to be turned.

Figure 2L:
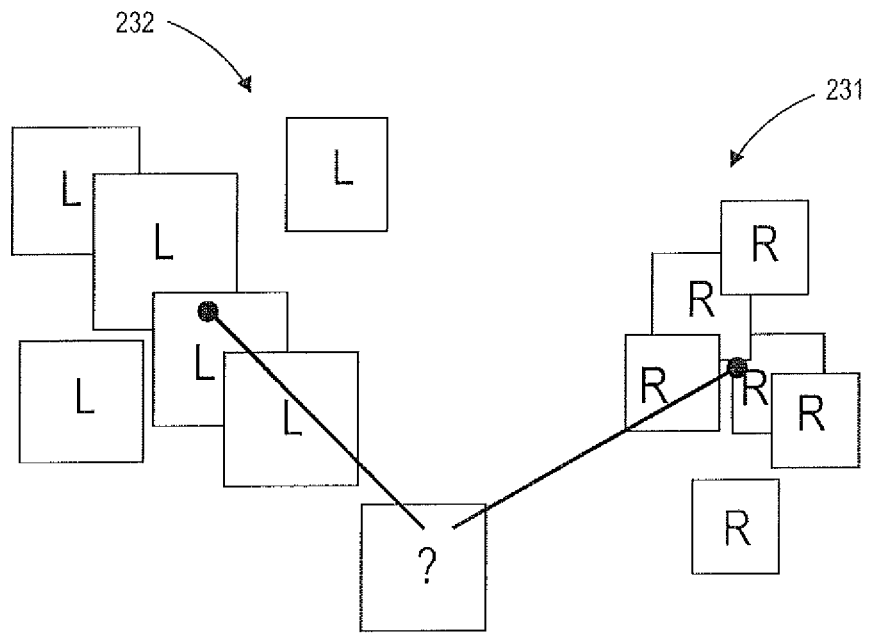
Figure 2M:
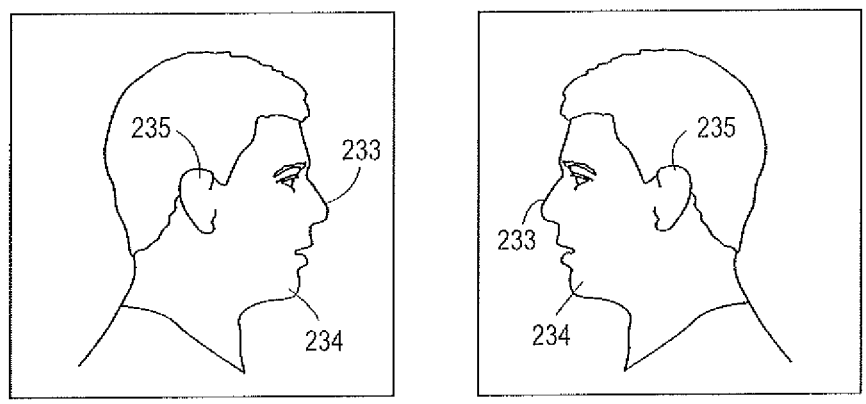

In another implementation, as shown in FIGS. 2L and 2M, the system 100 may receive one or more right-facing images 231 and left-facing images 232 of a patient 204. The system 100 utilizes machine-learning techniques that may include, but are not limited to: cascading Haar classifiers, decision tree algorithms, neural network algorithms, support vector machines, clustering, histogram of gradient techniques, and/or Bayesian network algorithms to generate a parameter utilized for computing a similarity metric between the images (e.g., a distance parameter, locations of specific identified features, and/or measure of confidence that a given subset of pixels represents a specific feature). The module 116 causes the processor 106 to process one or more depth frame images and apply the distance parameter (e.g., similarity metric) to pixels identified as representing one or more facial characteristics. Based upon the application of the parameter and/or the metric, the processor 106 generates a signal representing a possible orientation of the patient (e.g., the side on which the patient is lying).

The module 116 may utilize machine learning techniques (e.g., utilizes a machine learning classifier) to cause the processor 106 to determine a subset of pixels that the processor 106 determines most likely to represent the body, a body part, and/or the face of the patient. The processor 106 is also configured to output a confidence parameter (e.g., a value ranging between 0 and 1) representing the confidence that the subset of pixels identified is the body, the body part, and/or the face. In some implementations, the module 116 is configured to cause reporting of an orientation of the body, a body part, and/or face (for example, via a degree of rotation, where −90 degrees represents the patient facing left, 0 degrees represents the patient facing up, 90 degrees means facing right, etc.) and a confidence parameter associated with that orientation. The confidence parameter is based on how similar the current situation is to situations that the machine learned classifier has encountered before, as measured by a similarity metric. In another implementation, the processor 106 can build a decision tree and/or a decision forest from a repository of pre-classified data to determine a subset of pixels that the processor 106 determines most likely to represent the body, body part, and/or the face of the patient. For example, the processor 106 can be configured to read from a repository of pre-tagged frames and train itself to classify pixels in the same manner as the pre-tagged frames. The processor 106 can generate a learned output of a subset of pixels most likely to represent the body, the body part, and/or the face of the patient. The module 116 can cause the processor 106 to compare new frames to the learned output and classify the pixels accordingly. New frames can also be tagged and added to the repository for further machine learning.

In some implementations, the system 100 can use cluster-based learning techniques to implement one or more of the machine learning techniques described herein. For example, multiple computing devices 104 can be configured to work in parallel as cluster nodes 104a-c to build one or more decision trees. In some embodiments, each cluster node 104a-c can build one or more decision trees in a decision forest. For example, the module 116 can cause the processor 106 of each cluster node 104a-c to train on a specified set of pixels and/or frame images containing those pixels from the repository of pre-tagged framed images. In implementations, each frame image can be duplicated and flipped to allow the processor 106 to train on both left- and right-facing images. The processor 106 can generate a learned output of a subset of pixels most likely to represent the body, the body part, and/or the face of the patient. The processor 106 can use the learned output to generate one or more decision trees that are storable in memory 108 and/or cluster memory 126. The cluster nodes 104a-c can communicate via the communication network 110 to compile the individual decision trees into a decision forest that is storable in memory 108 and/or cluster memory 126. The module 116 can cause the processor 106 to run new frames through the decision forest and identify those pixels which represent the body, the body part, and/or the face of a patient. For example, a pixel can be identified as belonging to a given class if a specified percentage of decision trees in the decision forest identify the pixel as belonging to said class.

Machine learning parameters can be altered by a user to increase or decrease positive predictive value (PPV), sensitivity, and/or speed of the system 100. Machine learning parameters can include, but are not necessarily limited to: level of segmentation of input data (i.e., number of buckets of data fed to each cluster node 104a-c); number of points sampled from the X, Y, and/or Z spaces, pixel distance thresholds, subsampling length, and percentage of pixels selected from each frame to learn against, number of decision trees to train, and so forth.

It is to be understood that the use of specific machine learning techniques (i.e., decision tree learning) is offered by way of example only and is not meant to be restrictive of the present disclosure. In other implementations, one or more alternative machine learning techniques can also be used. Machine learning techniques can include, but are not necessarily limited to: convolutional neural networks, inductive logic programming, association rule learning, inductive logic programming, representation learning, and so forth, and any combination thereof.

Figure 2N:
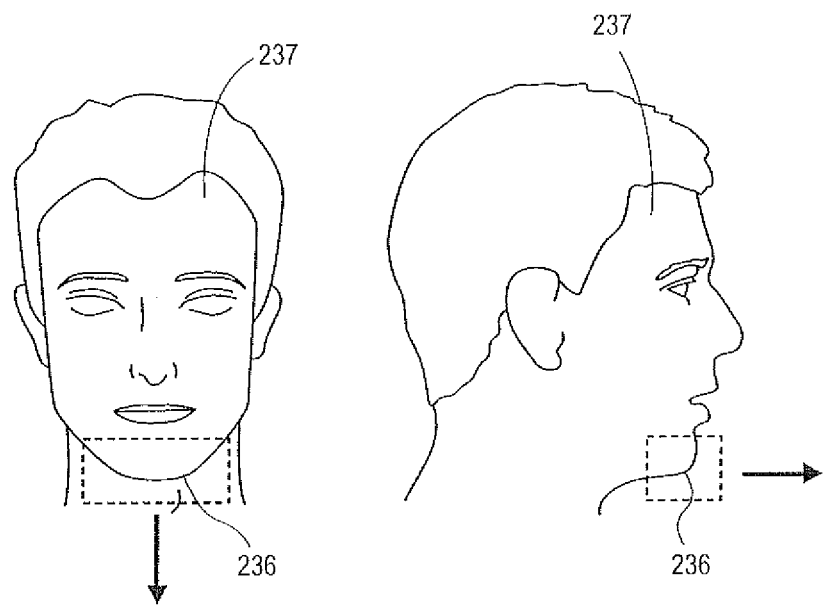

As shown in FIG. 2M, the module 116 is configured to cause the processor 106 to identify a subset 233 of pixels as representing one or more facial characteristics of the patient. For example, the processor 106 is configured to determine whether the face is right-facing or left-facing with respect to the camera 102 based upon the orientation of the pixels representing the one or more facial characteristics. The module 116 may cause the processor 106 to identify one or more pixels representing facial characteristics (e.g., direction of the pixels representing the nose 233, direction of the pixels representing the chin 234, characteristics of the pixels representing the ears 235, etc.) utilizing a feature recognition technique, such as a Haar recognition technique. Based upon the orientation of the identified pixels of the facial characteristics, the processor 106 is configured to determine a state of the patient. For instance, the state of the patient may be positioned on the patient's right side with respect to the camera 102, positioned on the patient's left side with respect to the camera 102, or positioned on the patient's back. In some implementations, the processor 106 is configured to cross-reference the characteristics 120 with the identified pixels of the facial characteristics to determine an orientation of the facial characteristics with respect to the camera 102. For example, the fusion engine 118 may utilize one or more of the characteristics 120 to assist the processor 106 in determining the orientation of the facial characteristics with respect to the camera 102. In a specific implementation, as shown in FIG. 2N, the system 100 is configured to identify one or more pixels as representing a chin 236 of the patient. For example, the module 116 causes the processor 106 to identify pixels as representing a chin of the patient. Based upon the orientation/direction of the chin, the processor 106 generates a signal representing a possible directionality (e.g., orientation) of the head 237, which is utilized to determine a state of the patient (e.g., the side on which the patient is lying).

Figure 2O:
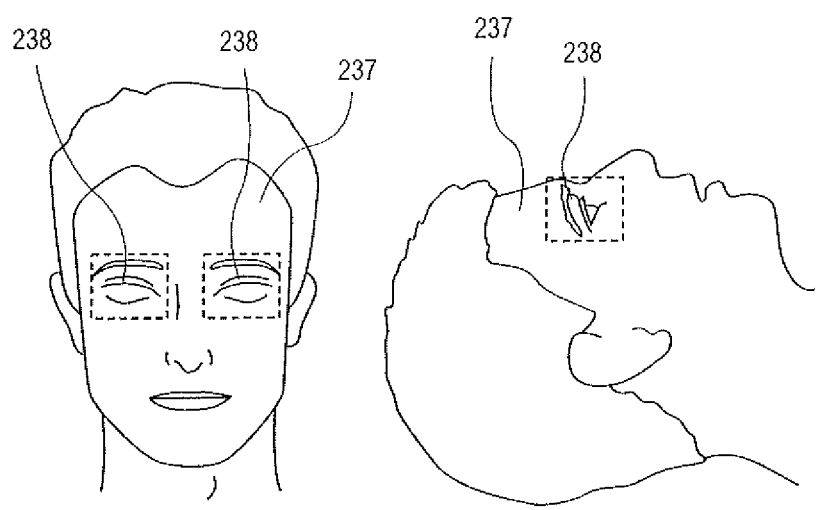

As shown in FIG. 2O, the system 100 is configured to identify pixels representing an eye socket 238 (or eye sockets) of the patient. In an implementation, the module 116 is configured to cause the processor 106 to identify the eye socket(s) based upon RGB values (e.g., signals such as hue, shading, color, etc.) of the pixels representing the eye sockets as compared to the depth values of the pixels representing the surround regions of the face of the patient. Based upon the identified pixels, the processor 106 is configured to determine the orientation (direction) of the head 237 of the patient. Thus, this orientation comprises one of the signals (e.g., signal represents the determined orientation) that is used, in conjunction with other signals, to determine a probability distribution of the possible states of the patient.

Figure 2P:
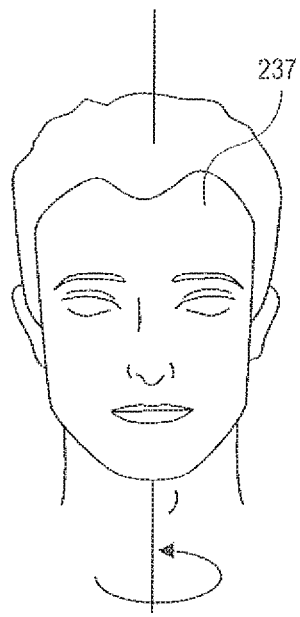

As shown in FIG. 2P, the system 100 is configured to generate a distance metric for various orientations of the patient's head 237. For example, over a time interval, the system 100 monitors a patient. The processor 106 is configured to measure between at least two pixels representing distinct regions of the patient's head (e.g., pixels representing ear and pixels representing chin, pixels representing eye, pixels representing mouth, pixels representing nose and pixels representing mouth, pixels representing nose and pixels representing chin, pixels representing ear and pixels representing mouth, etc.) and generate at least one distance metric relating to the distinct regions. In some examples, patient photos may be utilized by the system 100 as "seed" data (e.g., initial data provided to the system 100 utilized as a template). The processor 106 is configured to utilize this distance metric as training data to generate a virtual rotation of possible orientations of the head. Thus, the processor 106 generates a set of distance metrics corresponding to one or more potential orientations of the patient's head (e.g., generate a distance metric for each orientation of the patient's head). Based upon the depth frame images, the processor 106 processes the depth frame images to identify pixels representing one or more facial characteristics. The processor 106 applies the distance metric to the identified pixels to generate a signal representing a possible orientation of the patient's head.

Figure 2Q:
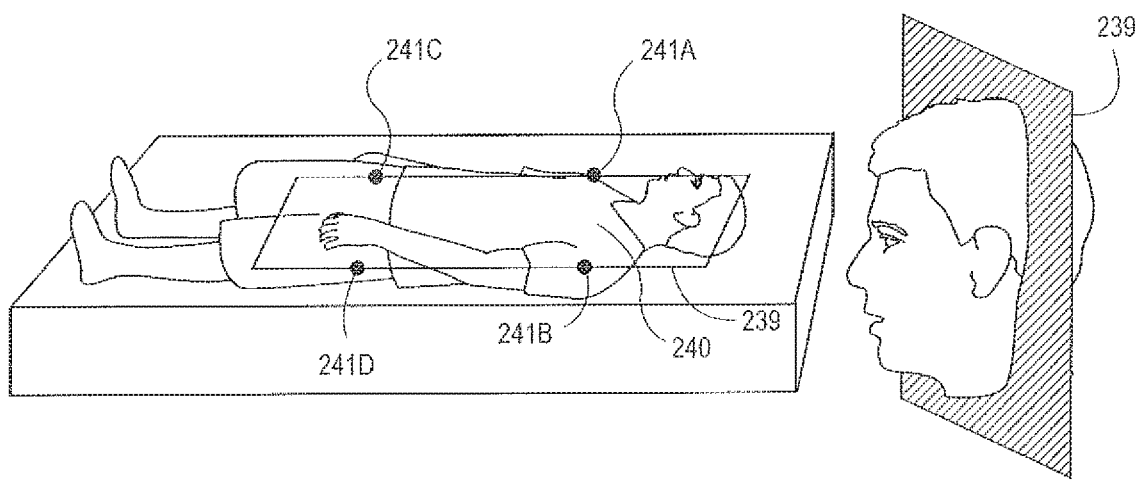

As shown in FIG. 2Q, the processor 106 is configured to apply a plane 239 (e.g., identifying a geometric equation for a plane where depth values that satisfy the equation approximately match depth values of pixels within) to the upper torso region 240 of the patient's body approximating the coronal plane (e.g., shoulder and hip points 241A through 241D) utilizing a color or a depth frame image. For example, the processor 106 identifies pixels from a depth frame image corresponding to two or more regions (e.g., shoulders and hips, etc.) of the patient's torso. The processor 106 is configured to identify pixels corresponding to facial characteristics situated to one side of the coronal plane or the other. If the processor 106 determines that a first threshold of the pixels representing the head's mass (e.g., nose, chin, ears) are on a given side of the plane 239, the processor 106 determines that the side on which the patient is lying is the patient's left side or right side as appropriate. Thus, based upon the number of pixels representing the head identified and their position relative to the plane, the processor 106 is configured to generate a signal representing a possible state of the patient.

Figure 2R:
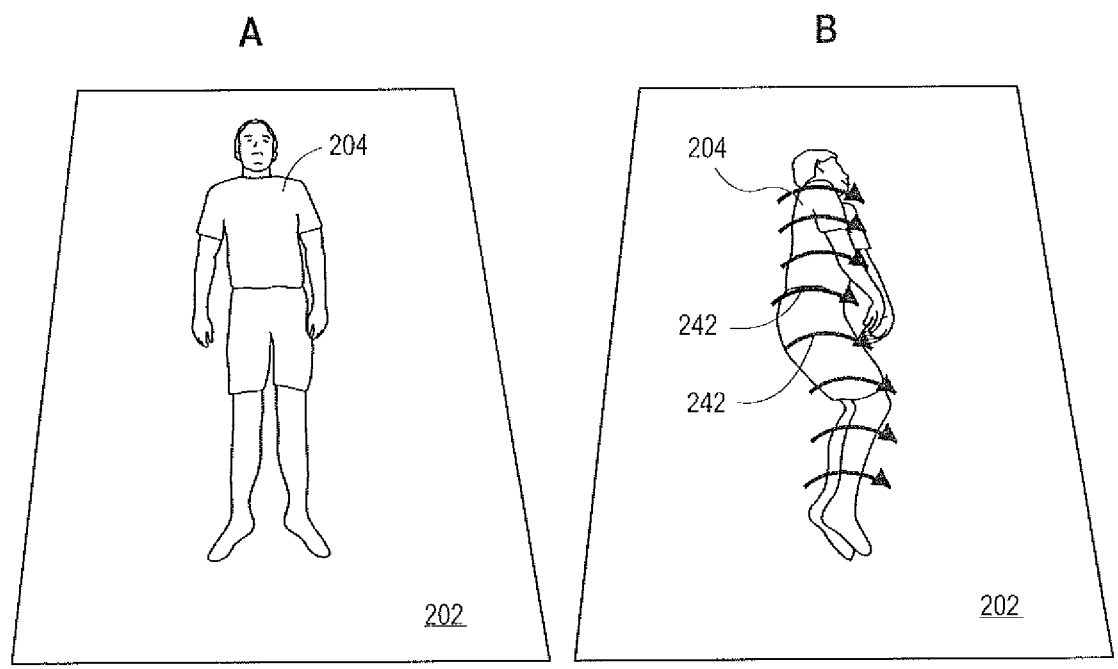

The module 116 is configured to cause the processor 106 to track a direction of rotation of the patient's body. For example, as shown in FIG. 2R, the processor 106 may identify one or more pixels representing the patient 204 to track (see FIG. 2R "A"). Thus, the processor 106 is configured to track a point (e.g., a pixel) through successive depth frame images, which would represent a direction vector 242 or direction vectors 242 over a set amount of time (e.g., processor 106 generates one or more direction vectors 242 based upon the tracked points). The processor 106 can identify an average direction of the motion based upon the tracked point through successive depth frame images aggregating information from each pixel to generate a signal representing a possible side on which the patient is lying (see FIG. 2R "B"). The processor 106 can then use this information to determine if the patient is changing between states (e.g. the patient is turning from their left side to facing forward, or from their right side to lying on their stomach, or from lying down to sitting up). If no such rotation motion has been identified over a period of time, the processor 106 determines that a patient's need to be turned may be increased (e.g., increase the probability that the patient should be turned).

Figure 2S:
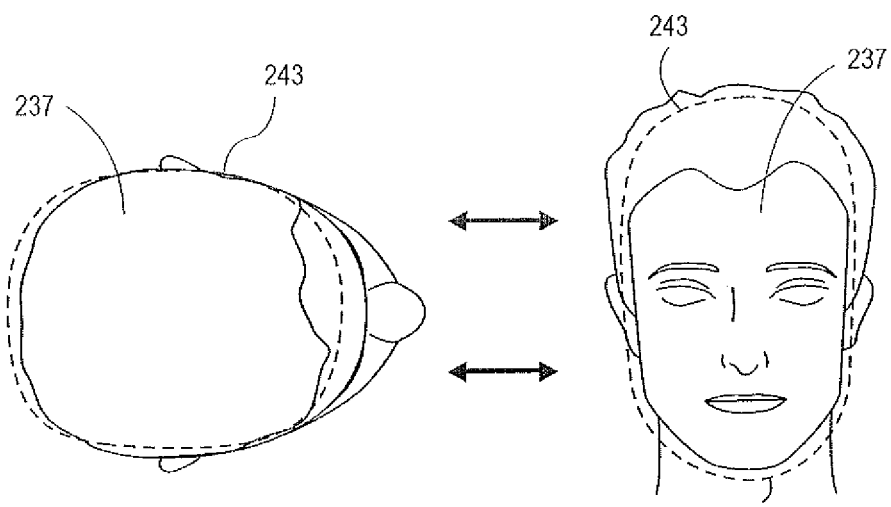

In an implementation, the module 116 causes the processor 106 to track pixels representing the head 237 of the patient (see FIG. 2S). In a specific implementation, the module 116 causes the processor 106 to identify pixels approximately matching a geometric template 243 (e.g., an ellipsoid). For instance, the geometric template 243 may be preprogrammed within the system 100 to provide the system 100 a baseline for identifying pixels representing a body part of the patient. In other words, the geometric template may be a characteristic 120. Thus, the system 100 may include one or more geometric templates 243 corresponding to one or more body parts. In some implementations, the processor 106 identifies a subset of pixels (e.g., a window of pixels) and determines whether a number of pixels within the subset of pixels approximately match the geometric template 243. In order to identify the pixels representing the body part, the module 116 may cause to the processor 106 to utilize a suitable matching module that translates (e.g., rotates) the geometric template 243 to approximately match the template to the pixels representing the body part. This could for example be used to determine orientation of the body part. Based upon a matching geometric template, the processor 106 is configured to generate a signal representing a possible state of the patient.

Figure 2T:
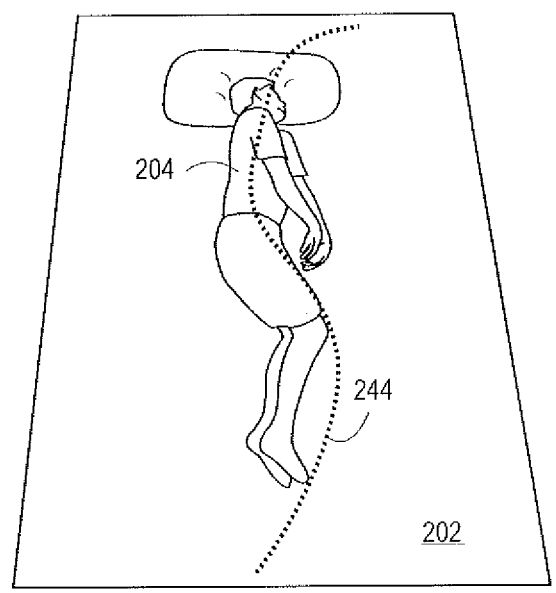

In another implementation of the present disclosure, the module 116 causes the processor 106 to identify a cluster of pixels (e.g., a clustering of pixels) above the top plane 202 to determine a body position within the bed. For example, the module 116 may utilize one or more sampling techniques that are tolerant to a certain amount of noise (e.g., wrinkles in the bed sheet, etc.). For example, the processor 106 is configured to construct a model utilizing data representing the bed based upon one or more depth/color frame images. The processor 106 then removes (e.g., subtracts) the data representing the bed such that the remaining data represents the body (or is associated with the body). In another example, suitable geometric analysis or machine learned feature extractions may be utilized. Thus, the processor 106 identifies a number of pixels having a depth value above the bed to determine a state (e.g., orientation, body shape, etc.) of the patient within the bed. For example, if the processor 106 identifies a number of pixels forming a characteristic "S" shape 244 (see FIG. 2T), the processor 106 determines that the patient is on his or her side (since patient probably could not form an "S" shape while on the patient's back). Additionally, the shape may be utilized to determine the side on which the patient is lying. For example, the processor 106 may cross-reference the identified shape with characteristics 120 to generate a signal representing a possible state of the patient. In some implementations, processor 106 is configured to implement one or more modules to identify when the patient is facing the edge of the bed. For example, the processor 106 can determine the sum of the squares of the depths of pixels classified as belonging to the torso of the patient. If the sum exceeds a specified threshold, the processor 106 determines that the patient is facing the edge of the bed. If the processor 106 determines that such a shape has not disappeared or changed from right side to left side over a period of time (e.g., a predetermined period of time), the processor 106 increases the probability that the patient needs to be moved to reduce the risk of a pressure ulcer (e.g., determines that the probability that a patient needs to be moved to reduce risk of a pressure ulcer is to be increased).

Figure 2U:
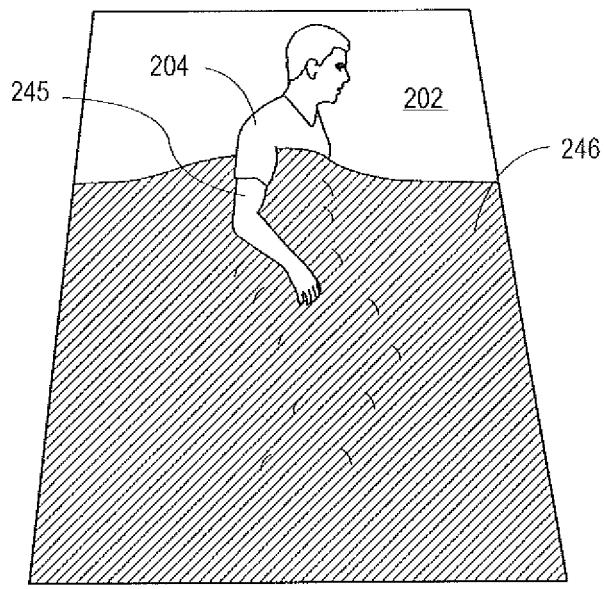

As shown in FIG. 2U, the module 116 is configured to cause the processor 106 to identify pixels representing an arm 245 of the patient 204. The processor 106 may identify pixels representing the arms 245 (e.g., having a depth value proximal to camera 102 as compared to the depth value of the pixels representing the top plane 202 and/or blankets 246 and/or having a color value distinct from the color value of the blankets). In an implementation, the processor 106 determines the state of the patient based upon the orientation of the pixels representing the arms 245 (e.g., an arm is jointed and can only be angled in certain directions). Thus, the processor 106 is configured to cross-reference the pixels representing the arms 245 (e.g., orientation of the arm) to generate a signal representing a possible state of the patient (e.g., the side on which the patient is lying).

Figure 2V:
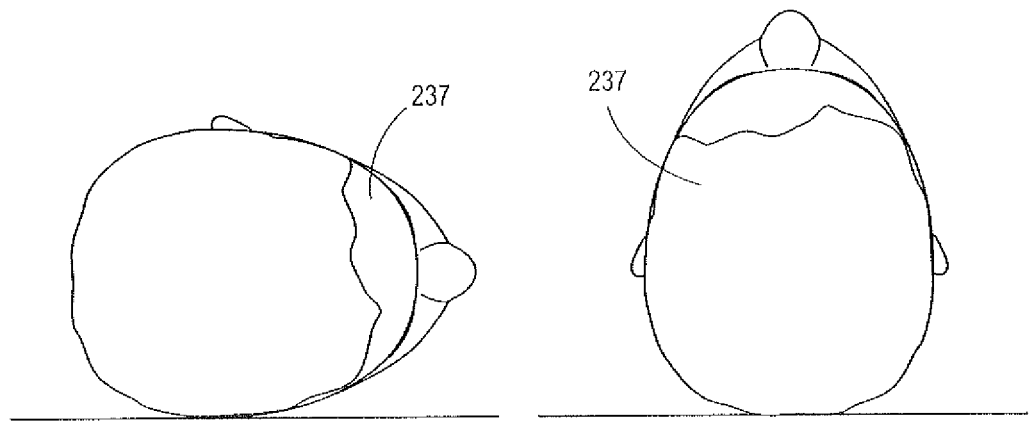

As described above, the processor 106 is configured to identify one or more pixels representing the patient's head 237 (see FIGS. 2N, 2O, and 2V). Upon identifying the pixels representing the patient's head 237, the module 116 causes the processor 106 to generate a signal representing a possible state (e.g., orientation of the head) based upon the contour of the pixels. For example, the processor 106 may identify the contour of the head based upon the pixels representing one or more facial features of the patient (e.g., pixels representing the chin, pixels representing the eye sockets, pixels representing the nose, etc.).

Figure 2W:
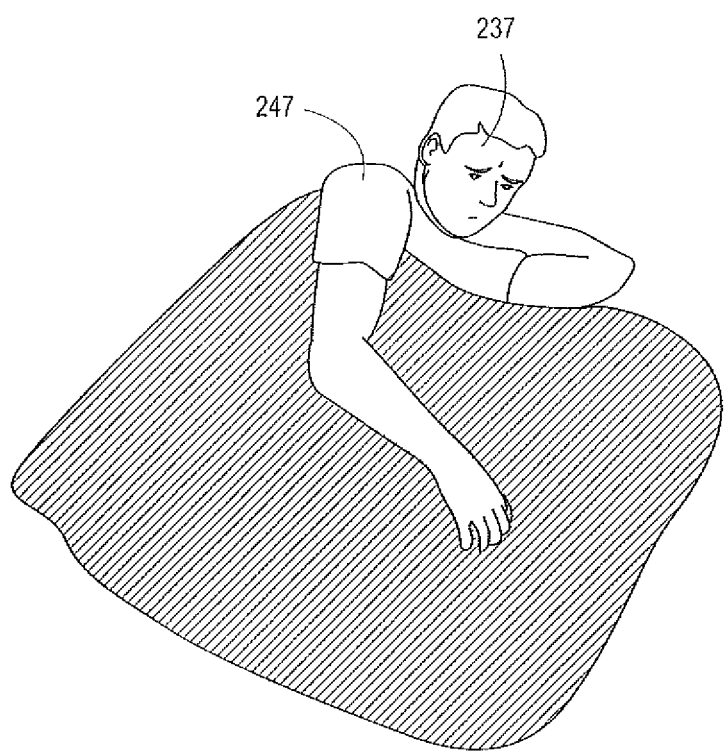

In an implementation, as shown in FIG. 2W, the processor 106 is configured to determine a state of the patient 204 (e.g., the side on which the patient is lying) based upon the depth values of the pixels of the shoulders 247 as compared to the depth values of the pixels of the head 237. For example, if the patient is positioned on the patient's back, the processor 106 may compare the depth values of the pixels representing the head 237 and the pixels representing the shoulders 247. If the depth values of the pixels representing the shoulder 247 are at or below the depth values of the pixels representing the head 237 (with respect to the pixels representing the top plane 202), the processor 106 determines the patient is positioned on his or her back. If the depth values of the pixels representing the shoulder 247 are above the depth values of the pixels representing the head 237, the processor 106 generates a signal representing a possible state of the patient (e.g., the side on which the patient is lying).

Figure 2X:
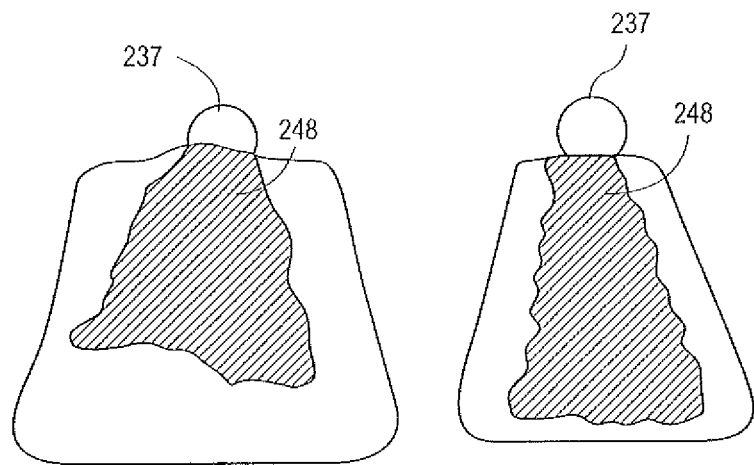

In another implementation, as shown in FIG. 2X, the module 116 is configured to cause the processor 106 to identify and to monitor a length of a number (e.g., a subset 248 of pixels) of pixels having a depth value "above" the bed (e.g., a subset 248 of pixels closer to the camera 102 as compared to the pixels representing the top plane 202). In one or more implementations, the characteristics 120 may include a length parameter indicating a length of the person and/or sheets when the person is in an extended position (e.g., positioned on the patient's back). When the patient is positioned on his or her side, the patient's feet may be closer to the patient's head to represent a non-extended position. The processor 106 is configured to compare the length of the subset 248 of pixels with the length parameter to generate a signal representing a possible state of the patient (e.g., whether the patient is in the extended position (e.g., supine or prone position) or the patient is positioned in a non-extended position (positioned on the patient's side).

Figure 2Y:
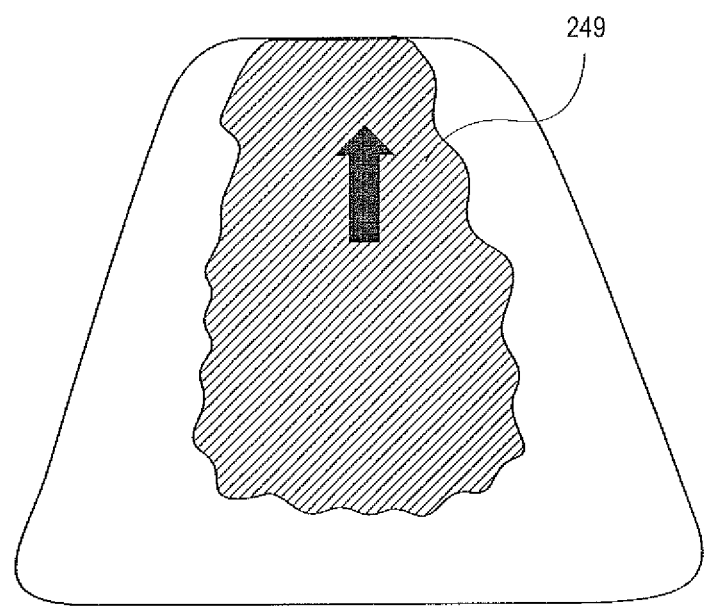

In some implementations, as shown in FIG. 2Y, the module 116 causes the processor 106 to monitor the pixels over a time period to identify moving pixels (e.g., moving points). In one or more implementations, the system 100 monitors the physical environment over an extended period of time to compensate for camera noise and/or other disturbances within the FOV of the camera 102. Thus, the processor 106 may be configured to identify a subset 249 of moving pixels (e.g., pixels having varying depth values from one or more depth frame images) that represent breathing (e.g., arrow represents the subset 249 of moving pixels). Based upon the monitored moving pixel characteristics, the processor 106 is configured to generate a signal representing a possible state of the patient (e.g., that the patient is on the patient's back).

In one or more implementations, the patient monitoring module 116 can cause the processor 106 to issue an electronic communication based upon one or more states described above. For example, the patient monitoring module 116 may represent functionality to cause the processor 106 to track movement of the patient within the bed over a defined period of time. Based on the monitoring techniques described above, the processor 106 can determine whether the patient has changed position (e.g., patient moved from one side to the other, patient moved from a side to the patient's back, moved from lying to sitting, etc.). For instance, the processor 106 can track the patient's movement from one image frame to the next for a defined period of time (e.g., a defined number of image frames). The processor 106 can then determine if the patient has changed positions within the defined period of time. For example, the processor 106 can monitor changes in the depth values of the patient's body parts to determine if the patient has changed positions. If the processor 106 determines that the patient has not changed positions, the processor 106 issues (e.g., generates and causes transmission) an electronic communication alert. The electronic communication alert may be transmitted to medical personnel to indicate that the patient has not changed positions and needs to be repositioned. If the processor 106 determines that the patient has changed positions, the processor 106 can issue an electronic communication alert indicating that the patient does not require repositioning.

In some implementations, the system 100 can utilize one or more sensors 124 (e.g., pressure sensors or motion sensors placed under or proximate to a patient bed) in addition to tracking the pixels to determine whether the patient has changed positions. For example, if an existing pressure sensor placed under the patient in the bed. The pressure sensor is configured to report approximate pressures or weight resting on the bed in a number of zones, and the system 100 is configured to receive the signal from the sensor 124. When the pressure sensor signals that pressures or weights resting on the bed have changed, the signal received from the sensor 124 causes the processor 106 to analyze the pixels above the bed and determine if a turn has occurred and to what degree. In another configuration, the signal of weights resting on the bed includes the specific geometries of the bed (e.g., zone 1 is 12" square on the front-left corner of the bed and is detecting 2 psi, Zone 2 is 12" square and horizontally adjacent to Zone 1 and is detecting 1 psi) and the processor 124 is configured to fuse this data with the current reading of depth values in relation to the computed bed plane to better determine the position of a patient in the bed. As an example in this configuration, a zone with low volume in 3D space according to the depth signal and high pressure according to the pressure sensor signal indicates an area of very high pressure or density. In this configuration, this measure of density may be monitored over time to ensure that it is reduced over time, potentially reducing the risk of developing pressure ulcers in that area.

In an implementation, the patient monitoring module 116 can cause the processor 106 to issue an electronic communication based upon an identification of an action (e.g., gesture) performed by the object 204. For example, the patient monitoring module 116 may represent functionality to cause the processor 106 to identify a gesture performed by the patient. For instance, based upon one or more monitoring techniques described above, the module 116 causes the processor 106 to determine a gesture has been performed based upon an identification of pixels representing a specific body part (e.g., an arm) and to detect movement of the pixels representing the specific body part. The system 100 is configured to track the movement of the identified pixels to determine if the identified pixels correspond to a predetermined movement (e.g., predefined pattern). If the movement matches (e.g., approximately matches) a predetermined movement, the module 116 causes the processor 106 to determine a gesture has been performed (e.g., waving of an arm, movement of a leg, etc.). For example, the processor 106 compares the detected movement to preprogrammed parameters to determine whether the movement is a gesture. Based upon a gesture, the processor 106 issues (e.g., generates and causes transmission) an electronic communication. The electronic communication may be transmitted to medical personnel to indicate that the patient is requesting medical personnel.

The system 100 may also be configured to cause issuance of an electronic communication based upon relative activity of a specific patient. In an implementation, the characteristics 120 may further include data and/or parameters (e.g., activity thresholds) relating to a specific patient's activity (e.g., activity baselines) during specific time periods (e.g., day time, night time). As described above, the module 116 includes functionality to identify pixels representing an object 204 and/or specific body parts associated with the object 204. The module 116 also includes functionality to track activity levels during time periods and compare the tracked activity levels with the characteristics 120. For example, based upon one or more of identified subsets of pixels associated with the object (e.g., head, torso, legs, blanket, arms, etc.), the module 116 causes the processor 106 to track the identified subset of pixels over a discrete time period. As described above, the processor 106 can also track movement (or non-movement) of the object 204. The processor 106 compares data representing the tracked movement (or non-movement) to the characteristics 120, the processor 106 determines a movement parameter during the discrete time period. If the movement parameter is outside the movement threshold, the processor 106 is configured to issue an electronic communication to medical personnel regarding the movement of the object 204. For example, if the movement of the object 204 is outside of the movement threshold, the processor can determine that a repositioning event has occurred (e.g., the patient has repositioned himself, the patient has been repositioned by a caregiver etc.). The module 116 can then cause the processor 106 to issue an electronic communication alert indicating that the object does not require repositioning. In other embodiments, the processor 106 is configured to issue an electronic communication alert based on non-movement of the object. For example, if the movement of the object is within the movement threshold, or no movement is detected, the processor 106 can issue an electronic communication alert indicating that the patient requires repositioning.

Figure 2Z:
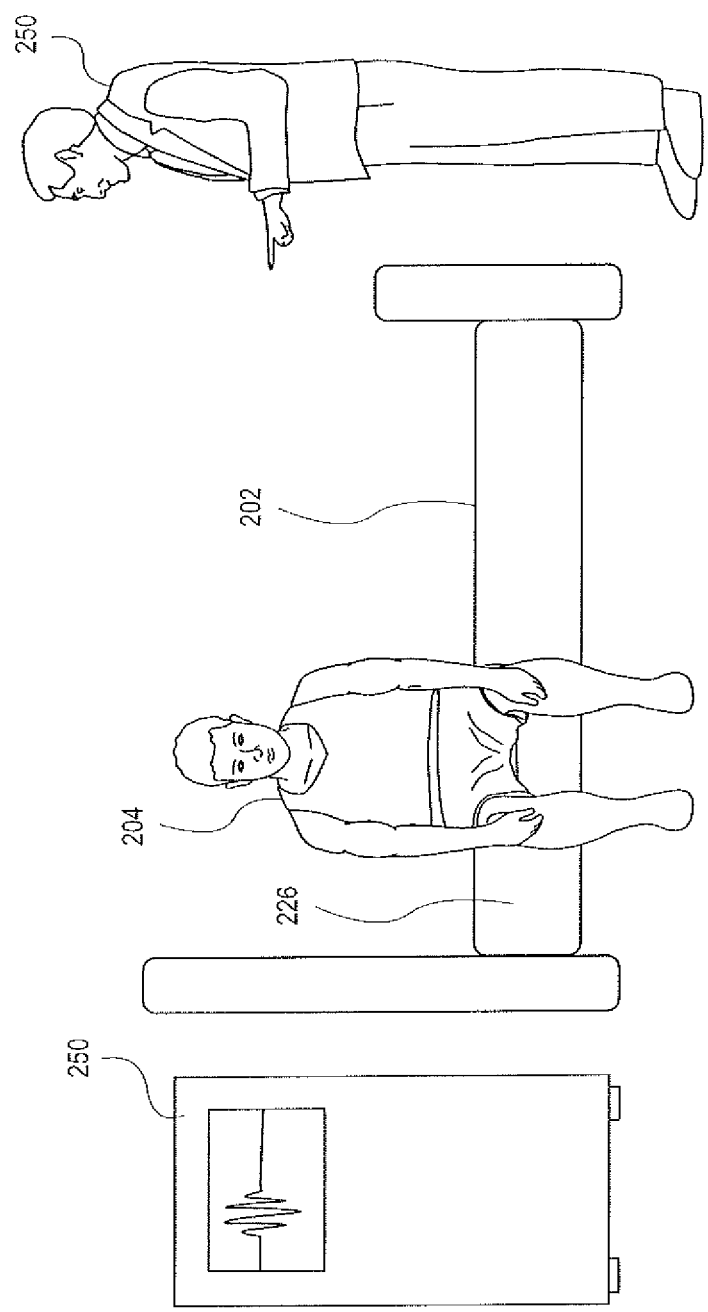

In some implementations, as shown in FIG. 2Z, the system 100 is configured to track other objects 250 within the FOV of the camera 102. For example, the objects 250 may be medical personnel or the objects 250 may be equipment (e.g., medical equipment such as tray tables, respiratory ventilators, medical furniture, intravenous (IV) equipment, and the like) within the patient's room. For example, the module 116 may cause the processor 106 to identify another subset of pixels as representing an object 250 according to one or more of the techniques described above. The module 116 can cause the processor 106 to implement one or more modules to identify an object 250. For example, the processor 106 can use known dimensions of objects 250 to model the objects 250. The processor 106 can iterate the model over each pixel of a specified height range in the frame image and rotate the model. The processor 106 can implement a fitness module by comparing pixels that lie outside of the model and pixels that lie within the model to determine whether the object 205 is present in the frame image.

In one or more implementations, the processor 106 can build a decision tree and/or a decision forest from a repository of pre-classified data to determine a subset of pixels that the processor 106 determines most likely to represent an object 250. For example, the processor 106 can be configured to read from a repository of pre-tagged frames and train itself to classify pixels in the same manner as the pre-tagged frames. In some implementations, a user can tag points representing the perimeter of an object 250 (e.g., corners of a tray table). The processor 106 can generate a learned output of a subset of pixels most likely to represent an object 250. The module 116 can cause the processor 106 to compare new frames to the learned output and classify the pixels accordingly. New frames can also be tagged and added to the repository for further machine learning.

In some instances, the processor 106 identifies a subset of pixels representing medical personnel (e.g., a nurse, a doctor, etc.) and determines a time parameter based upon how long the medical personnel were in the FOV of the camera 102 and when the medical personnel entered (and exited) the FOV. The time parameter may indicate whether the medical personnel interacted with the patient or whether the medical personnel simply observed the patient. In some implementations, the system 100 may furnish the time parameters to properly credentialed personnel. These personnel may utilize the time parameters to ensure that the medical personnel monitored the patient during one or more time periods.

In another implementation, people tracking processes monitor (e.g., through the processor 106) for an object 250 in the patient room that is a person leaning over the bed and assisting the patient. This monitoring is done by tracking the center of the tracked person and the head of the tracked person by way of averaging the tracked pixels of the person to find an object center or using a machine learned process for head tracking. When the person is assisting or caring for the patient, these keys points move over the edge of the bed 202 and are tracked as such. When the person ends their care or assistance of the patient, these key points transition away from the bed (e.g., the pixels are transitioning a position distal from the bed). These changes in the resulting depth pixels above the bed are then analyzed by the processor 106 to determine if a turn has occurred and to what degree.

The module 116 may include functionality to utilize time parameters to modify alert thresholds associated with the patient. For example, as described above, one or more electronic communications may be issued based upon a state of the patient. These electronic communications may also be based upon an alert threshold. For example, the module 116 may cause issuance of an electronic communication when it has been determined that the patient has remained in the same position for a defined period of time. In some instances, the alert threshold may be increased or decreased based on the presence of a caregiver (e.g., medical personnel) and/or caregiver characteristics. Thus, in an implementation, an alert threshold may be increased after medical personnel have exited the FOV without repositioning the patient. In another implementation, the alert threshold may be decreased before a scheduled visit of the medical personnel.

The module 116 may also have functionality to determine whether medical equipment in the patient's room is in the proper location (e.g., position). In some implementations, as described above, the objects 250 may represent medical equipment or other objects within the patient's room. For example, the objects may comprise tray tables, respiratory ventilators, medical furniture, intravenous (IV) equipment, and the like. The module 116 may include functionality to ensure proper location of the objects 250 within the FOV of the camera 102. For example, the module 116 may cause the processor 106 to identify pixels representing one or more objects 250 and determine a position of the objects 250 within the FOV of the camera 102. The processor 106 cross-references the determined position of the object 250 with an object 250 position parameter that indicates where the object 250 should be positioned. If the object 250 is not positioned correctly, the processor 106 issues an electronic communication indicating that the object 250 is not positioned correctly. In some implementations, the objects 250 may comprise bed rails, and the system 100 is configured to determine whether the bed rails are in an upward position or a downward position. The system 100 may compare the values of the pixels representing the bed rails between frames over a discrete time period to determine whether the bed rails have transitioned positions. The system 100 may also compare the values of the pixels representing the bed rails to the values of the pixels representing another object or subject between frames over a discrete time period to determine a configuration of the bed rails.

The module 116 may also include functionality to ensure medical equipment is properly functioning. As disclosed above, the module 116 includes functionality to identify pixels representing a patient's extremities and to determine whether the extremities are moving. The module 116 may also cause the processor 106 to determine whether equipment attached to the patient is functioning properly. For example, the patient may be utilizing a continuous passive motion (CPM) device for knee joint recovery. Based upon the detected motion of the patient's leg, the processor 106 may be configured to determine whether the CPM device is properly flexing and/or extending the patient's knee.

The module 116 also includes functionality to determine whether the patient is not properly positioned. For example, the module 116 is configured to cause the processor 106 to determine whether the patient is entangled within the bed (e.g., leg stuck in rail) or in an orientation that is deemed unsafe. In an implementation, the processor 106 is configured to compare (e.g., cross-reference) pixels representing one or more portions (e.g., extremities) of the patient with pixels representing one or more objects (e.g., bed rails, edge of the bed, etc.). Based upon the cross-reference, the processor 106 may determine the patient is in an unsafe orientation based upon the positioning of the pixels representing the patient's extremities with respect to the pixels representing the one or more objects (e.g., bed rails, edge of bed, etc.). When a determination is made that the patient is in an unsafe orientation, the module 116 causes the processor 106 to issue an electronic communication to alert medical personnel.

In one or more implementations, the system 100 is configured to determine whether the patient is attempting to leave the bed by way of the head of the bed or the foot of the bed. For instance, the module 116 causes the processor 106 to identify pixels representing a head of the bed and/or a foot of the bed. This identification may be accomplished through one or more of the techniques described above. The module 116 also causes the processor 106 to monitor pixels representing the patient (or a portion of the patient) over a time period. If the pixels representing the patient interface with the pixels representing the head of the bed or the foot of the bed (e.g., pixels representing the patient have approximately the same depth value as pixels representing head/foot of the bed), the processor 106 determines the patient is attempting to transition from the bed via the head/foot of the bed. In one or more implementations, the module 116 causes the processor 106 to issue an electronic communication to alert medical personnel in response to this determination.

In one or more implementations, the system 100 can receive feedback from the caregiver(s) in response to the electronic communication alerts. For instance, the module 116 can cause processor 106 to issue an electronic communication alert that can be accepted or dismissed by the caregiver. For example, if the alert is not valid (e.g., the alert is not relevant to medical personnel, the patient is not actually performing the alerted movement, the patient has repositioned himself, the patient has already been repositioned, etc.), the caregiver can dismiss the alert. The module 116 can then cause the processor 106 to determine whether or not to issue future alerts based on the feedback received. For example, if the caregiver accepts the alert, the processor can issue future alerts when the state, motion, and/or gesture associated with the subject and/or object is determined. The system 100 can issue increasingly accurate and relevant electronic communication alerts for a patient by incorporating electronic communication alert responses over a time period.

In some implementations, the system 100 is configured to issue an electronic communication alert to medical personnel in response to a combination of a determination of patient movement and/or a patient state, as described above, and predetermined risk parameters. For instance, the module 116 causes the processor 106 to calculate a base risk score for the patient using a sensitivity module based on one or more of the characteristics 120 (e.g., age, gender, weight, body type/dimensions, diagnoses, time of day, able-bodied, gait characteristics, patient repositioning protocol, history of pressure ulcers, mental status, physical restrictions, facial deformalities, sleeping abnormalities, angle of bed, dimensions of bed, additional equipment in room, fall risk score, patient schedule, call light signal, bed alarm signal, alarm history, fall risk score, medication records, caregiver has moved the patient, patient ethnicity and/or skin tone, bed characteristics, patient history of side lying activity, etc.). The module may also include one or more caregiver characteristics 122 (e.g., caregiver schedules, average response time, patient medication, caregiver location, minimum repositioning protocol, etc.). The one or more characteristics 120 and/or the one or more caregiver characteristics 122 may be furnished to the system 100 by the user, such as a caregiver, observed and learned by the system 100 utilizing suitable machine learning techniques as described above, and/or integrated from other systems. In some implementations, the module can further include a manual sensitivity adjustment (e.g., the caregiver can manually increase the sensitivity of the alert system for high risk patients, etc.). The module 116 can cause the processor 106 to determine an alert sensitivity level for the patient corresponding to base risk score (e.g., the system 100 can be more sensitive to the movements and/or patient states of patients with high base risk scores, etc.).

Once the processor 106 has determined an alert sensitivity level for the patient, the module 116 can cause the processor 106 to determine if the determined patient movement or patient state creates a risk to the patient. For example, if the patient's base risk score and corresponding alert sensitivity level are high, the module 116 can cause the processor 106 to determine that small patient movements or small changes in a patient state cause a risk to the patient. When a determination is made that the determined patient movement or patient state is causing a risk to the patient, the module 116 causes the processor 106 to issue an electronic communication to alert medical personnel.

In an implementation, the system 100 can generate the alert sensitivity level from a base risk score determined from an module comprising at least one of the Morse Falls Risk Scale reading for the patient, the average alert response time by a caregiver as observed by the system, the medication record as provided in the EMR, and a risk score generated by the system for the patient's recent movements. The module 116 can cause the processor to assign a numerical value for each input using comparisons of the current patient's activities with the activities of all previous patients observed by the system, as graded on a normal distribution scale. The processor 106 can combine these numerical values together, with each input carrying an independent weight. The processor 106 then determines the numerical base risk score for the patient, which determines the sensitivity of the system for that patient. In some implementations, caregivers can further increase or decrease that risk score, thereby further adjusting the sensitivity of the system.

In some implementations, the base risk score can comprise a base pressure ulcer risk score. For example, the module 116 causes the processor 106 to calculate a base pressure ulcer risk score for the patient using a sensitivity module based on one or more of the characteristics 120 (e.g., age, gender, weight, body type/dimensions, diagnoses, time of day, able-bodied, gait characteristics, patient repositioning protocol, history of pressure ulcers, mental status, physical restrictions, facial deformalities, sleeping abnormalities, angle of bed, dimensions of bed, additional equipment in room, fall risk score, patient schedule, call light signal, bed alarm signal, alarm history, fall risk score, medication records, caregiver has moved the patient, patient ethnicity and/or skin tone, bed characteristics, patient history of side lying activity, etc.). The module may also include one or more caregiver characteristics 122 (e.g., caregiver schedules, average response time, patient medication, caregiver location, minimum repositioning protocol, etc.). The one or more characteristics 120 and/or the one or more caregiver characteristics 122 may be furnished to the system 100 by the user, such as a caregiver, observed and learned by the system 100 utilizing suitable machine learning techniques as described above, and/or integrated from other systems. In some implementations, the module can further include a manual sensitivity adjustment (e.g., the caregiver can manually increase the sensitivity of the alert system for high risk patients, etc.). The module 116 can cause the processor 106 to determine an alert sensitivity level for the patient corresponding to base repositioning score (e.g., the system 100 can be more sensitive to the movements, positioning, and/or patient states of patients with high base positioning scores, etc.). Once the processor 106 has determined an alert sensitivity level for the patient, the module 116 can cause the processor 106 to determine if the determined patient position or patient state creates a risk to the patient. For example, if the patient's base pressure ulcer risk score and corresponding alert sensitivity level are high, the module 116 can cause the processor 106 to determine that lack of movement and/or changes in position over a defined period of time causes a risk to the patient. When a determination is made that the determined patient position or patient state is causing a risk to the patient, the module 116 causes the processor 106 to issue an electronic communication to alert medical personnel the has remained in the same position for a defined period of time and/or that patient requires repositioning.

In one or more implementations, the system 100 may utilize suitable machine learning techniques to adjust the sensitivity level in response to changes in the characteristics 120 and/or the caregiver characteristics 122. For example, the system 100 may receive call light information from the nurse call system and the processor 106 can increase the sensitivity (e.g., alarm earlier) to patient movement, patient state, and/or patient position during the period of time when the call light is active. In another example, the processor 106 may increase sensitivity (e.g., alarm earlier) during times when a nurse location system indicates there are no nurses within a certain distance from the room. In another example, the system 100 may receive medication schedules and history from the electronic medical record system and the processor 106 can increase sensitivity (e.g., alarm earlier) during the time period following the administration of certain medications.

In one or more implementations, the system 100 may utilize suitable machine learning techniques to adjust the sensitivity level of the electronic communication alerts in response to caregiver feedback. For instance, the module 116 can cause processor 106 to issue an electronic communication alert that can be accepted or dismissed by the caregiver. For example, if the alert is not valid (e.g., the patient is not actually at risk, the patient has repositioned himself, the patient has been repositioned, etc.), the caregiver can dismiss the alert. The module 116 can then cause the processor 106 to incorporate the accepting or dismissal into the module to adjust the base risk score and corresponding alert sensitivity level (e.g., increase or decrease sensitivity) accordingly. The system 100 can identify an increasingly accurate risk score and corresponding alert sensitivity level for a patient by incorporating electronic communication alert responses over a time period.

In an implementation, the system 100 can adjust the sensitivity level of the electronic communication alerts based on a machine-learned decision tree built from observed patient behaviors. The module 116 can cause processor 106 to issue an electronic communication alert that can be accepted or dismissed by the caregiver. For example, if the alert is not valid (e.g., the patient is not actually at risk, the patient has been repositioned, etc.), the caregiver can dismiss the alert. The module 116 can then cause the processor 106 to incorporate the accepting or dismissal into the machine-learned decision tree to adjust the base risk score and corresponding alert sensitivity level (e.g., increase or decrease sensitivity) accordingly. In this implementation, if a future behavior reaches this same alerting node in the decision tree, the system 100 can ignore or intensify its alerting based on this previous feedback.

In one or more implementations, the system 100 can adjust the sensitivity level of the electronic communication alerts in response to a recorded history of patient behaviors that led to an alert. For example, the module 116 can further cause the processor 106 to record the history of patient behaviors (e.g., patient is transitioning from the bed, patient turning within the bed, patient transitioning from a lying position to a sitting position, etc.) that resulted in a specific alarm. If these patient behaviors recur in the future, the system the system 100 can ignore or intensify its alerting based on this previous feedback. For instance, the module 116 can cause the processor 106 to incorporate this feedback into the module and/or the decision tree.

In one or more implementations, the system 100 can adjust the sensitivity level of the electronic communication alerts by retaining a plurality of depth pixels from the time of the alert or the time leading up to the alert. For example, the module 116 can further cause the processor 106 to record the plurality of depth pixels that occurred during or leading to a specific alarm. If this plurality of pixels recurs in the future, the system the system 100 can ignore or intensify its alerting based on this previous feedback. For instance, the module 116 can cause the processor 106 to incorporate this feedback into the module and/or the decision tree.

In some implementations, the system 100 can issue an alert to notify the caregiver of activities that typically constitute a higher risk score. For example, if a patient that is assigned a low risk score is frequently showing patient movement associated with high risk patients, the processor 106 can issue an electronic communication alert to inform the caregiver of this behavior and the recommendation to increase fall risk and/or the alert sensitivity level for that patient.

In some implementations, the system 100 can issue an alert to notify the caregiver of activities during certain periods of the day that typically constitute a higher risk score. For example, if a patient movement is frequently detected during a certain period of the day (e.g., 12 pm to 2 am) that typically constitutes a higher risk score, the processor 106 can issue an electronic communication alert to inform the caregiver to implement a custom sensitivity level for that period of the day.

In one or more implementations, the system 100 can suspend and/or suppress alerting to minimize false alarms, increasing the accuracy of the system 100. For example, the module 116 can cause the processor 106 to suppress alerting when the presence of a second person (e.g., caregiver, medical personnel, etc.) is detected in the room. In some implementations, the module 116 can cause the processor to detect a caregiver within the FOV of the camera 102 utilizing one or more of the techniques described above (e.g., identify a subset of pixels representing medical personnel). In other embodiments, the system 100 can be configured to interface with third party systems that can detect the presence or absence of the caregiver. For example, the module 116 can be configured to detect the presence of a sensor (e.g., sonic sensor, RFID sensor, etc.) located on the caregiver.

In some implementations, the module 116 can be configured to suspend and/or suppress alerting when the caregiver places the patient in a selected position. For example, if the caregiver sets the patient up on the edge of the bed and leaves the room, the module 116 can cause the processor 106 to suppress alerting. The module 116 can cause the processor 106 to detect movement of the patient from the position and issue an alert if the caregiver is not in the room. For example, if the patient attempts to stand after the caregiver has left the room, the module 116 can cause the processor 106 to issue an alert.

The module 116 can be further configured to suspend and/or suppress alerting when the patient is engaged in certain activities (e.g., eating, exercising, undergoing medical testing, etc.). The system 100 is configured to track other objects 250 (e.g., tray table, medical equipment, exercise equipment, etc.) within the FOV of the camera 102 utilizing one or more of the techniques described above, and can suspend and/or suppress alerting when one or more of the objects 250 is detected. For example, the module 116 may cause the processor 106 to identify subset of pixels as representing a tray table in front of the patient. The module 116 can cause the processor 106 to suspend alerting when the patient is utilizing the tray table.

In some implementations, the system 100 can be configured to resume alerting after a designated period of time has passed. The module 116 can cause the processor 106 to resume alerting if the patient has remained alone in a selected position for an extended period of time. For example, if the caregiver places the patient on the patient's side within the bed, and is then absent from the room for an designated period of time, the module 116 can cause the processor 106 to issue an electronic communication alert reminding the caregiver that the patient is in the position. In some implementations, the module 116 can utilize one of the modules described above (e.g., alert sensitivity level, base risk score, base pressure ulcer risk score, etc.) to determine an appropriate time period for the patient (e.g., shorter time period for a high risk patient, longer time period for a low risk patient, etc.). For example, if a high pressure ulcer risk (e.g., high base pressure ulcer risk score) patient remains lying on the same side without repositioning for more than two hours, the module 116 can cause the processor 106 to issue an electronic communication alert reminding the caregiver that the patient is in the position. In other implementations, the designated time period can be manually selected (e.g., by the caregiver).

In some implementations, the system 100 can increase alerting based on the presence and/or absence of the caregiver. For example, the module 116 can cause the processor 106 to issue an alert when the presence of a second person (e.g., caregiver, medical personnel, etc.) is detected in the room, and the second person exits the room without changing the state of the patient (e.g., without repositioning the patient). In some implementations, the module 116 can cause the processor to detect a caregiver within the FOV of the camera 102 utilizing one or more of the techniques described above (e.g., identify a subset of pixels representing medical personnel). In other embodiments, the system 100 can be configured to interface with third party systems that can detect the presence or absence of the caregiver. For example, the module 116 can be configured to detect the presence of a sensor (e.g., sonic sensor, RFID sensor, etc.) located on the caregiver.

In one or more implementations, the system 100 is further configured to filter noise from the depth images. For instance, one or more modules can cause the processor 106 to create a pixel-by-pixel estimation of the mean and variance of the depth values of a nonmoving incoming plurality of pixels. The processor 106 can use the pixel-by-pixel depth value estimations to form a bin of estimates for each plurality of pixels that is storable in the memory 108. The processor 106 then compares the incoming plurality of pixels to the predetermined bin of estimates to determine conformity. If actual means and/or variances fall within the bin of estimates, the depth value of the estimates can be reported rather than the actual depth value of the incoming plurality of pixels. If there are slight differences between the actual means and/or variances, the processor 106 can update the bin of estimates accordingly. If the actual means and/or variances differ significantly from the bin of estimates, a new bin of estimates can be created. Both the original bin of estimates and the new bin of estimates can be retained in the memory 108 as a background bin and a foreground bin, respectively. The background and foreground bins can be used to create a background depth mask and a foreground depth mask, respectively. In this way, noise can be filtered from the depth channel, the depth value of each pixel can be determined with increased precision, and a more accurate depth mask of the environment can be generated.

Movement within the environment can be determined by identifying nonconforming pixels. For instance, the processor 106 can identify pixels that do not conform to their respective bins. The actual depth values of nonconforming pixels are reported. The processor 106 can be configured to determine that the nonconforming pixels are in motion using the techniques described herein (e.g., tracking pixels over a period of time, identifying pixels having varying depth values from one or more depth frame images, etc.).

In one or more implementations, an infrared light source may be utilized to further illuminate the environment to allow the camera 102 to operate within a darkened environment such that the processor 106 can generate one or more signals as described above in the various implementations described above.

Example Pressure Ulcer Prevention Processes

Figure 3A:
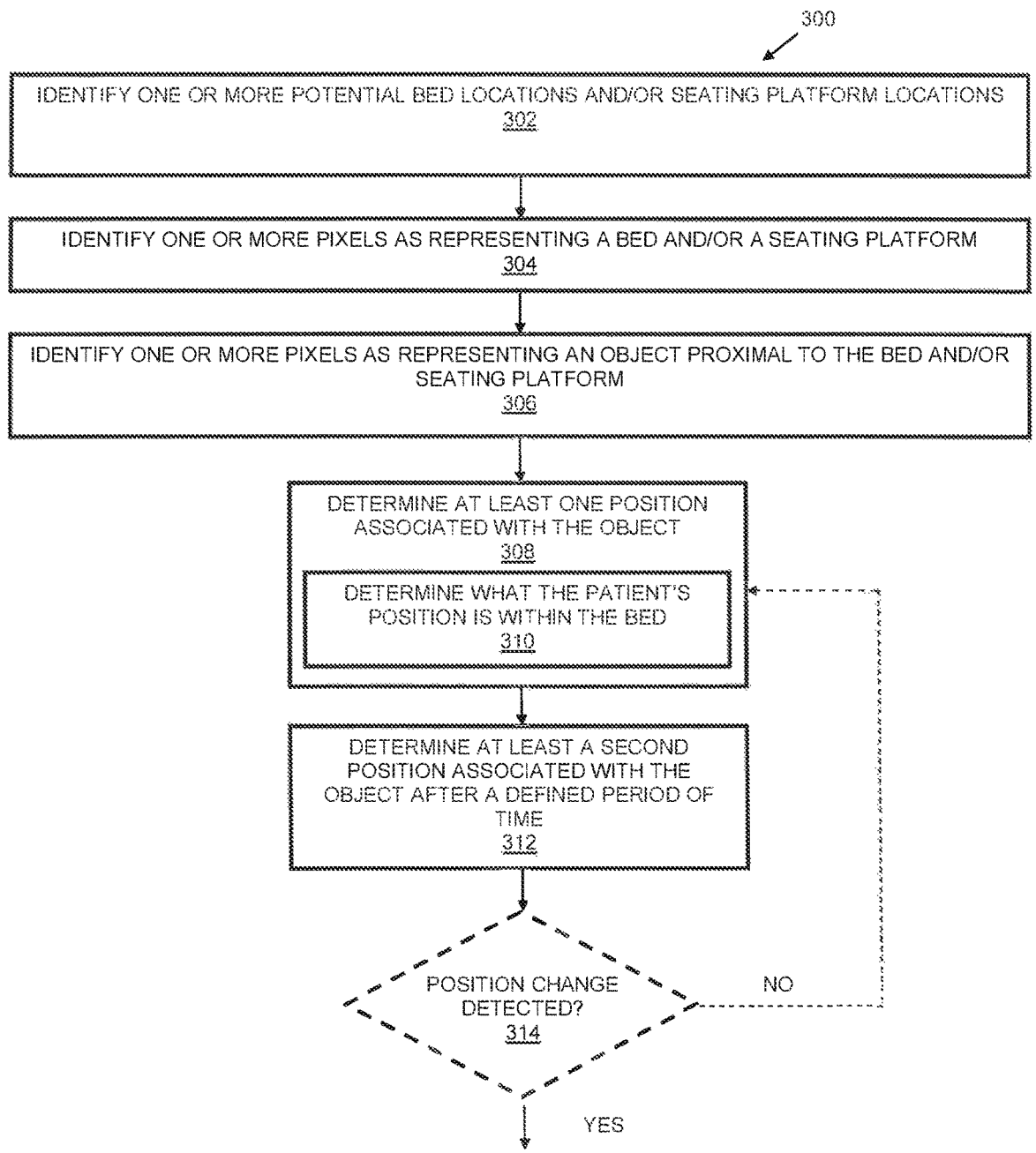
FIGS. 3A and 3B are flow diagrams illustrating an example method for detecting and preventing pressure ulcers in a medical environment in accordance with the present disclosure.
Figure 3B:
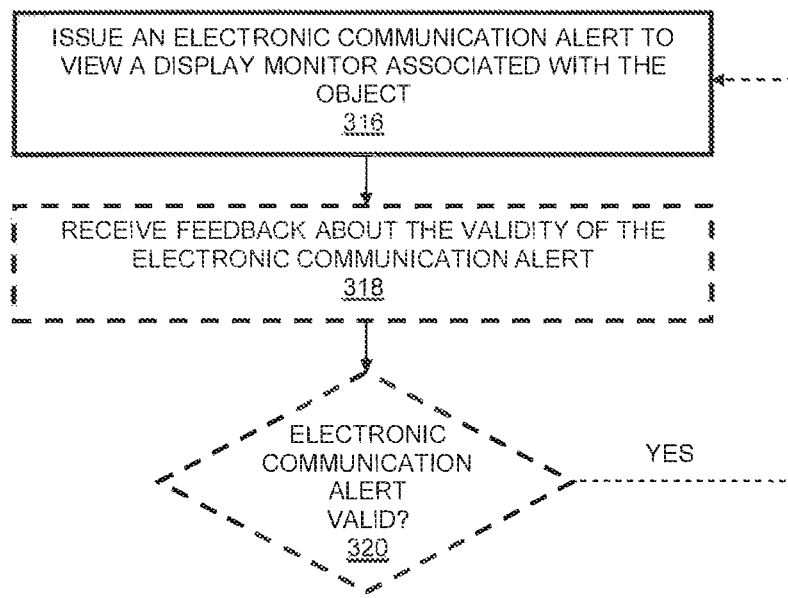

FIGS. 3A and 3B illustrate an example process 300 for preventing pressure ulcers utilizing an image capture system, such as the image capture system 100 described above. As shown in FIG. 3A, a plurality of potential bed locations and/or seating platform locations are identified (Block 302). As described above, the cameras 102 are configured to capture image data representing one or more frames within a FOV of the cameras 102 (e.g., data representing one or more color frame images, data representing one or more depth frame images). Once captured, the data is furnished to the computing device 104 to allow the module 116 to cause the classification of whether the pixels represent a portion of a bed. The module 116 can cause the processor 106 to execute one or more object location modules to identify potential bed and/or seating platform locations, as described above. For example, the module 116 can cause the processor 106 to create a Boolean array from the depth frames and estimate maximal rectangles representing potential bed and/or seating platform locations. This may be accomplished over one or more frames. In one or more implementations, the system 100 can filter noise from the depth frame images, as described above. For instance, the processor 106 can estimate the depth value of a nonmoving plurality of pixels and then comparing the actual depth value of the incoming plurality of pixels to the estimate. Variances from depth value estimates can be used to update the estimates, and/or generate foreground depth masks and background depth masks, as described above. This allows for more accurate depth values of pixels to be determined.

Once a plurality of potential bed and/or seating platform locations are identified, one or more pixels are identified as representing a bed and/or a seating platform based on the potential bed and/or seating platform locations (Block 304). The module 116 can cause the processor 106 to execute one or more object identification modules to reduce the potential bed and/or seating platform locations, to the one or more pixels most likely to represent a bed and/or a seating platform, as described above. For example, the processor 106 can execute one or more gradient ascent modules to identify one or more pixels with the highest fitness as representing the bed and/or the seating platform.

Once pixels representing the bed and/or seating platform are identified, one or more pixels representing an object (i.e., a human, such as the patient) proximal to the bed and/or seating platform are identified (Block 306). For example, based upon the depth data associated with each pixel, a grouping of pixels can be identified as representing an object within the bed. For instance, the module 116 may cause the processor 106 to identify one or more pixels as representing an object within the bed based upon the depth data (comparing a pixel's depth value to another pixel's depth value that represents the bed). In some implementations, the module 116 may utilize machine learning (e.g., utilizes a machine learning classifier) to cause the processor 106 to determine a subset of pixels that the processor 106 determines most likely to represent the body, a body part, and/or the face of the patient, using the techniques described above. For example, the processor 106 can implement one or more confidence parameters, decision trees, and so forth to the body, body part, and/or face of the patient. In some implementations, the system 100 can use cluster-based learning techniques to implement one or more of the machine learning techniques described herein. For example, multiple computing devices 104 can be configured to work in parallel as cluster nodes 104a-c to build one or more decision trees.

As shown in FIG. 3A, at least one position with the object is determined (Block 308). The position may be defined as whether the patient is still within the bed, whether the patient is positioned to one side of the bed, what the patient's position is within the bed (e.g., what side the patient is lying on) whether the patient is positioned on the floor (i.e., the patient is not in bed), whether the patient appears to be getting out of bed, and so forth. For example, a determination is made as to what side the patient is lying on (Block 310). In an implementation, an orientation, such as a positional orientation, of the object (e.g., the patient) within the bed can be determined utilizing the identified object pixels. This may allow for the system 100 to furnish proactive alerts to medical personnel that the patient is taking actions that are not desired (e.g., sitting up, getting up, moving to the edge of the bed, etc.). The system 100 can also furnish proactive alerts to medical personnel that the patient is taking actions that are desired (e.g., patient has repositioned himself, etc.).

At least a second position associated with the object is determined after a defined period of time (Block 312). The patient monitoring module 116 may represent functionality to cause the processor 106 to track movement of the patient within the bed over a period of time. Based on the monitoring techniques described above, the processor 106 can determine whether the patient has changed position (e.g., patient moved from one side to the other, patient moved from a side to the patient's back, moved from laying to sitting, etc.). For instance, the processor 106 can track the patient's movement from one image frame to the next for a defined period of time (e.g., a defined number of image frames).

A determination is made about whether the patient's position has changed (Decision Block 314). For example, the processor 106 can monitor changes in the depth values of the patient's body parts to determine if the patient has changed positions. If the processor 106 determines that the patient has not changed positions (NO to Decision Block 314), the processor 106 issues (e.g., generates and causes transmission) an electronic communication alert (e.g., e-mail, SMS text, MMS text, proprietary messaging services [e.g., HL7 messaging], etc.) is issued (e.g., generate and/or transmit) by the processor 106 and/or the communication module 112 to an electronic device (e.g., smart phone, handset, wireless voice message system, call light system, etc.) associated with medical personnel (Block 316). In another example, the electronic communication may alert medical personnel that the system 100 has determined that the patient has been positioned on the patient's side for over a defined period of time and that the patient requires repositioning. If the processor 106 determines that the patient has changed positions, the processor 106 can resume monitoring the state of the patient. In some implementations, the processor 106 can also issue an electronic communication alert indicating that the patient does not require repositioning.

In some implementations, the system 100 receives feedback from the caregiver(s) about the validity of the electronic communication alert (Block 318). As described above, the module 116 can cause processor 106 to issue an electronic communication alert that can be accepted or dismissed by the caregiver. For example, if the alert is not valid (e.g., the alerted patient position is not relevant to medical personnel, patient has already been repositioned, etc.), the caregiver can dismiss the alert. The processor 106 determines whether or not to issue future alerts based on the feedback received (Block 320). For example, if the caregiver accepts the alert, the processor can issue future alerts when the state associated with the object or subject is determined.

In one or more implementations, the system 100 can further enhance alerting accuracy by suspending and/or suppressing alerting to minimize false alarms. For example, the module 116 can cause the processor 106 to suppress alerting when the presence of a second person (e.g., caregiver, medical personnel, etc.) is detected in the room and/or when the patient is engaged in certain activities (e.g., eating, exercising, undergoing medical testing, etc.). In some implementations, the system 100 can increase alerting based on the presence and/or absence of the caregiver. For example, the module 116 can cause the processor 106 to issue an alert when the presence of a second person (e.g., caregiver, medical personnel, etc.) is detected in the room, and the second person exits the room without changing the state of the patient (e.g., without repositioning the patient).

Figure 4:
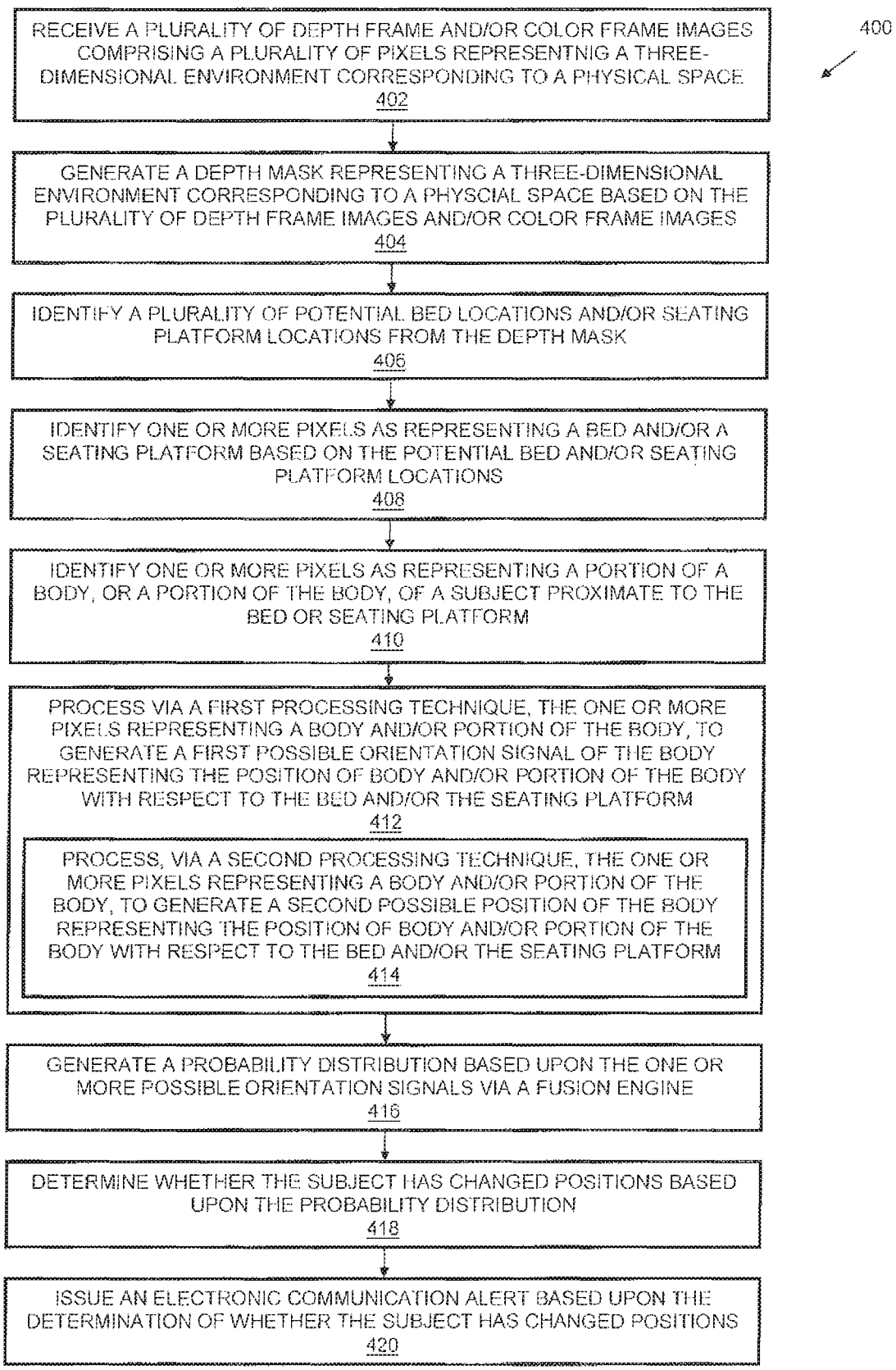
FIG. 4 is a flow diagram illustrating another example method for detecting and preventing pressure ulcers in a medical environment in accordance with the present disclosure.

FIG. 4 illustrates another example process 400 for preventing pressure ulcers by determining whether a patient's position proximate to a bed has changed utilizing an image capture system, such as the image capture system 100 described above. As shown in FIG. 4, data representing a plurality of depth frame images or a color frame images comprising a plurality of pixels representing a three-dimensional environment corresponding to a physical space is received (Block 402). In an implementation, data representing depth frame images and/or color frame images are furnished by an imaging device 102 (e.g., the camera 102) having an image plane.

A depth mask representing a three-dimensional environment corresponding to a physical space is generated based on the plurality of depth frame images and/or color frame images (Block 404). One or more modules are configured to cause the processor 106 to generate a depth mask from the frame images. For example, the module 116 is configured to cause the processor 106 to continually monitor for a predetermined amount of time (e.g., a plurality of frames) the depth value of at least substantially all of the pixels that represent the captured environment and stores the greatest (deepest) depth value associated with each pixel The processor 106 generates a depth mask comprising an accumulation of depth values and each value represents the deepest depth value of a pixel measured over the time interval. The processor 106 can then be instructed to generate a point cloud based upon the depth mask that includes a set of point values that represent the captured environment.

A plurality of potential bed locations and/or seating platform locations is identified from the depth mask (Block 406). The module 116 can cause the processor 106 to execute one or more object location modules to identify potential bed and/or seating platform locations, as described above. For example, the module 116 can cause the processor 106 to create a Boolean array from the depth frames and estimate maximal rectangles representing potential bed and/or seating platform locations.

Once a plurality of potential bed and/or seating platform locations are identified, one or more pixels are identified as representing a bed and/or a seating platform based on the potential bed and/or seating platform locations (Block 408). The module 116 can cause the processor 106 to execute one or more object identification modules to reduce the potential bed and/or seating platform locations, to the one or more pixels most likely to represent a bed and/or a seating platform, as described above. For example, the processor 106 can execute one or more gradient ascent modules to identify one or more pixels with the highest fitness as representing the bed and/or the seating platform.

Once a bed and/or a seating platform is identified, one or more pixels are identified as representing a body and/or a portion of a body of a subject proximate to the bed or seating platform (Block 410). For example, based upon the depth data associated with each pixel, a grouping of pixels can be identified as representing an object within the bed. For instance, the module 116 may cause the processor 106 to identify one or more pixels as representing an object within the bed based upon the depth data (comparing a pixel's depth value to another pixel's depth value that represents the bed). In some implementations, the module 116 may utilize machine learning (e.g., utilizes a machine learning classifier) to cause the processor 106 to determine a subset of pixels that the processor 106 determines most likely to represent the body, a body part, and/or the face of the patient, using the techniques described above. For example, the processor 106 can implement one or more confidence parameters, decision trees, and so forth to the body, body part, and/or face of the patient. In some implementations, the system 100 can use cluster-based learning techniques to implement one or more of the machine learning techniques described herein. For example, multiple computing devices 104 can be configured to work in parallel as cluster nodes 104*a-c* to build one or more decision trees.

As shown, the processor processes, via a first processing technique, the one or more pixels representing the body and/or portion of the body to generate a first possible orientation signal of the body and/or body part with respect to the image plane (Block 412). In an implementation, the processor 106 is configured to process the depth frame image or the color frame image utilizing a first processing technique (e.g., a first processing technique as described above with respect to FIGS. 2J to 2Z) to generate a first possible orientation signal of the body and/or body part representing the position of the body and/or portion of the body with respect to the bed and/or seating platform. In one or more implementations, the system 100 can filter noise from the depth frame images, as described above. For instance, the processor 106 can estimate the depth value of a nonmoving plurality of pixels and then comparing the actual depth value of the incoming plurality of pixels to the estimate. Variances from depth value estimates can be used to update the estimates, and/or generate foreground depth masks and background depth masks, as described above. This allows for more accurate depth values of pixels to be determined.

As shown in FIG. 4, the processor processes, via a second processing technique, the one or more pixels representing the body and/or a portion of the body to generate a second possible orientation signal of the body and/or body part with respect to the image plane (Block 414). In an implementation, the processor 106 is configured to process the depth frame image or the color frame image utilizing a second processing technique (e.g., a second processing technique as described above with respect to FIGS. 2J to 2Z) to generate a second possible orientation signal of the body and/or body part representing the position of the portion of the body and/or body part with respect to the bed and/or the seating platform. In some implementations, the processor 106 processes, via another processing technique (e.g., a third processing technique, a fourth processing technique, a fifth processing technique, etc.), one or more pixels representing the body and/or a portion of the body to generate another possible orientation signal of the body and/or body part with respect to the image plane. The processor 106 generates a probability distribution based upon the one or more possible orientation signals via a fusion engine (Block 416). As described above, the processor 106 is configured to generate a probability distribution via the fusion engine 118 based upon at least the first possible orientation signal, the second possible orientation signal, and/or the other possible orientation signals.

The processor determines whether the subject has changed positions based upon the probability distribution (Block 418). In an implementation, the processor 106 is configured to determine whether the subject has moved from the bed based upon the probability distribution. In another implementation, the processor 106 is configured to determine a change in orientation of the subject within the bed based upon the probability distribution (e.g., if the patient has changed sides, if the patient has moved from a side to the patient's back, etc.). In yet another implementation, the processor 106 is configured to determine that the subject is transitioning within the bed or transitioning from/to the bed.

As described above, an electronic communication alert (e.g., e-mail, SMS text, MMS text, HL7 messaging, etc.) is issued (e.g., generate and/or transmit) based upon the determination of whether the patient has changed positions (Block 420). For example, if the processor 106 determines that the patient has not changed positions, the processor 106 issues (e.g., generates and causes transmission) an electronic communication alert. The electronic communication alert may be transmitted to medical personnel to indicate that the patient has not changed positions and needs to be repositioned. If the processor 106 determines that the patient has changed positions, the processor 106 can issue an electronic communication alert indicating that the patient does not require repositioning. In some implementations, the system 100 receives feedback from the caregiver(s) about the validity of the electronic communication alert. As described above, the module 116 can cause processor 106 to issue an electronic communication alert that can be accepted or dismissed by the caregiver. For example, if the alert is not valid (e.g., the patient has repositioned himself, the patient has transitioned from lying to sitting, the patient has transitioned from the bed, etc.), the caregiver can dismiss the alert. In some implementations, the processor 106 determines whether or not to issue future alerts based on the feedback received. For example, if the caregiver accepts the alert, the processor 106 can issue future alerts when the state associated with the object or subject is determined.

In one or more implementations, the system 100 can further enhance alerting accuracy by suspending and/or suppressing alerting to minimize false alarms. For example, the module 116 can cause the processor 106 to suppress alerting when the presence of a second person (e.g., caregiver, medical personnel, etc.) is detected in the room and/or when the patient is engaged in certain activities (e.g., eating, exercising, undergoing medical testing, etc.). In some implementations, the system 100 can increase alerting based on the presence and/or absence of the caregiver. For example, the module 116 can cause the processor 106 to issue an alert when the presence of a second person (e.g., caregiver, medical personnel, etc.) is detected in the room, and the second person exits the room without changing the state of the patient (e.g., without repositioning the patient).

Figure 5:
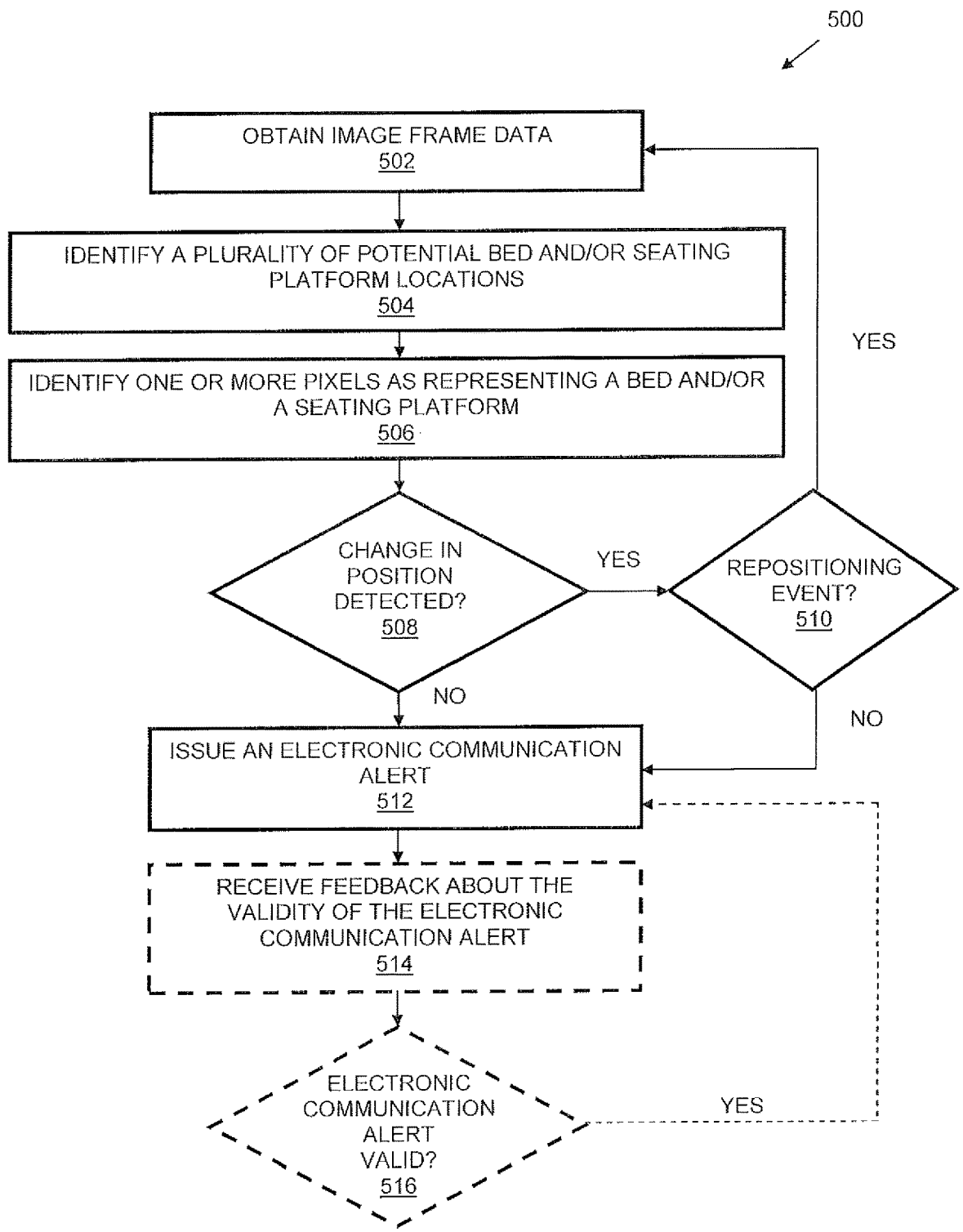
FIG. 5 is a flow diagram illustrating another example method for detecting and preventing pressure ulcers in a medical environment in accordance with the present disclosure.

FIG. 5 illustrates an example process 500 for identifying changes in position of an object, such as a patient. As shown, one or more frame images are obtained from an imaging device (Block 502). In one or more implementations, the system 100 can filter noise from the frame images, as described above. For instance, the processor 106 can estimate the depth value of a nonmoving plurality of pixels and then comparing the actual depth value of the incoming plurality of pixels to the estimate. Variances from depth value estimates can be used to update the estimates, and/or generate foreground depth masks and background depth masks, as described above. This allows for more accurate depth values of pixels to be determined.

A plurality of potential bed locations and/or seating platform locations is identified based on the image frame data (Block 504). The module 116 can cause the processor 106 to execute one or more object location modules to identify potential bed and/or seating platform locations, as described above. For example, the module 116 can cause the processor 106 to create a Boolean array from the depth frames and estimate maximal rectangles representing potential bed and/or seating platform locations. This may be accomplished over one or more frames.

Once a plurality of potential bed and/or seating platform locations are identified, one or more pixels are identified as representing a bed and/or a seating platform based on the potential bed and/or seating platform locations (Block 506). The module 116 can cause the processor 106 to execute one or more object identification modules to reduce the potential bed and/or seating platform locations, to the one or more pixels most likely to represent a bed and/or a seating platform, as described above. For example, the processor 106 can execute one or more gradient ascent modules to identify one or more pixels with the highest fitness as representing the bed and/or the seating platform.

A determination is made of whether motion was detected (Decision Block 508). The module 116 is configured to cause the processor 106 to determine whether a patient has changed positions based upon an identification of pixels representing the patient's body or a specific body part (e.g., an arm) and detecting movement of the pixels representing the body or the specific body part with respect to the bed and/or the seating platform. In implementations, the processor 106 can be configured to identify a body or a specific body part using the techniques described herein (e.g., comparing depth data, building decision trees, cluster-based learning, etc.). In implementations where filtering is utilized, movement within the environment can be determined by identifying pixels that do not conform to their depth value estimates, as described above. The processor 106 can be configured to determine that the nonconforming pixels are in motion using the techniques described herein (e.g., tracking pixels over a period of time, identifying pixels having varying depth values from one or more depth frame images, etc.).

If a change in position is detected (YES from Decision Block 508), the system 100 is configured to detect whether the change constitutes a repositioning event (Decision Block 510). For example, the module 116 can cause the processor 106 to determine if the detected movement constitutes an actual change in patient position (e.g., the patient has repositioned himself, the patient has transitioned from lying to sitting, the patient has transitioned from the bed, etc.). If the change in position is determined to be a repositioning event (YES from Decision Block 510), then the process 500 transitions back to Block 502. In some implementations, the processor 106 can issue an electronic communication alert indicating that the patient does not require repositioning.

If the change in position is not determined to be a repositioning event (NO from Decision Block 510), or no movement is detected (NO from Decision Block 508), an electronic communication alert is issued (Block 512). The electronic communication alert may be transmitted to medical personnel to indicate that the patient has remained in the same position for a determined period of time, and/or that the patient requires repositioning. In some implementations, the system 100 receives feedback from the caregiver(s) about the validity of the electronic communication alert (Block 514). As described above, the module 116 can cause processor 106 to issue an electronic communication alert that can be accepted or dismissed by the caregiver. For example, if the alert is not valid (e.g., the patient has repositioned himself, the patient has transitioned from lying to sitting, the patient has transitioned from the bed, etc.),), the caregiver can dismiss the alert. In some implementations, the processor 106 determines whether or not to issue future alerts based on the feedback received (Block 516). For example, if the caregiver accepts the alert, the processor can issue future alerts when the presence or absence of the gesture is detected.

In one or more implementations, the system 100 can further enhance alerting accuracy by suspending and/or suppressing alerting to minimize false alarms. For example, the module 116 can cause the processor 106 to suppress alerting when the presence of a second person (e.g., caregiver, medical personnel, etc.) is detected in the room and/or when the patient is engaged in certain activities (e.g., eating, exercising, undergoing medical testing, etc.). In some implementations, the system 100 can increase alerting based on the presence and/or absence of the caregiver. For example, the module 116 can cause the processor 106 to issue an alert when the presence of a second person (e.g., caregiver, medical personnel, etc.) is detected in the room, and the second person exits the room without changing the state of the patient (e.g., without repositioning the patient).

Figure 6:
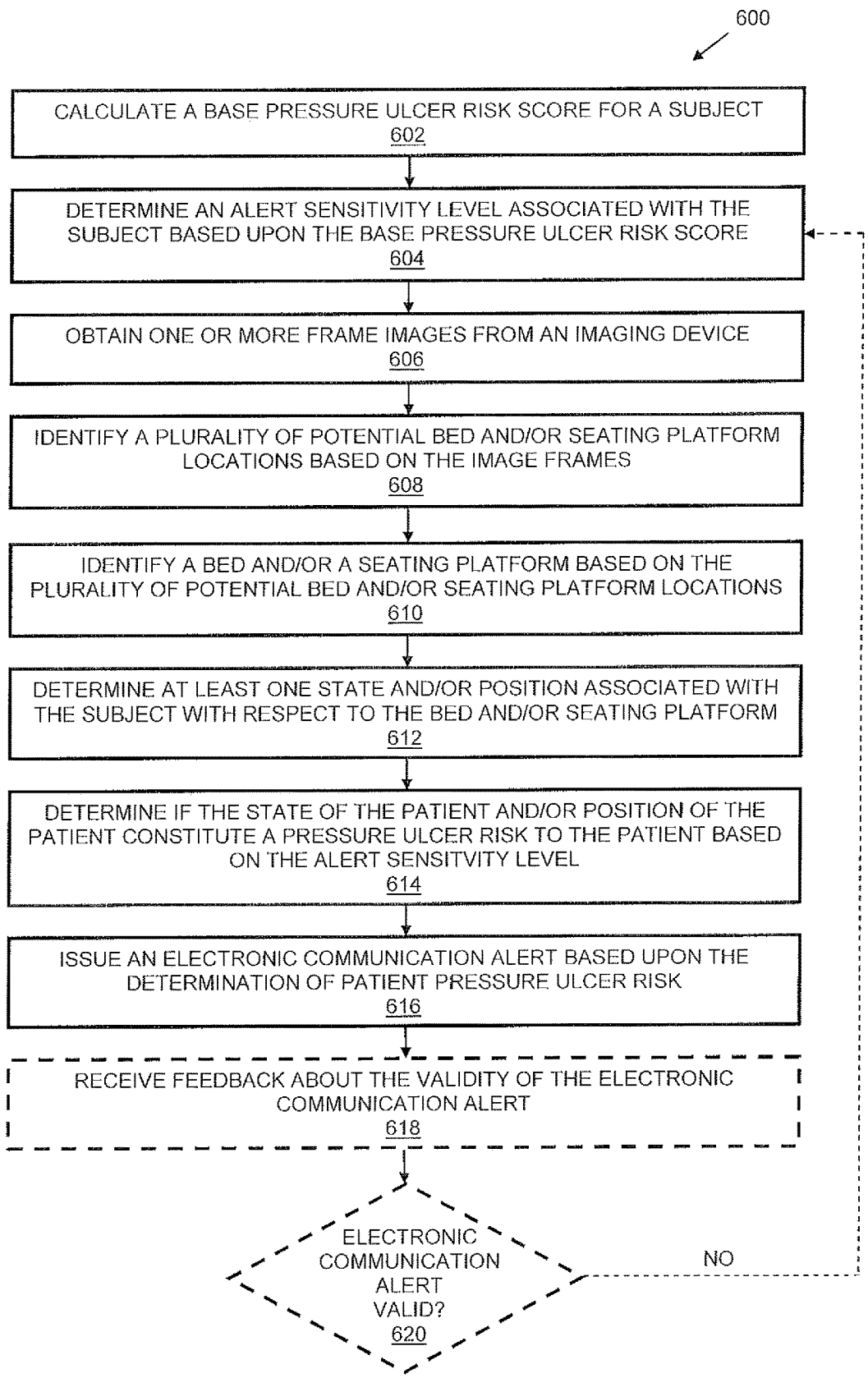
FIG. 6 is a flow diagram illustrating another example method for detecting and preventing pressure ulcers in a medical environment in accordance with the present disclosure.

FIG. 6 illustrates an example process for issuing an electronic communication alert to medical personnel based on a patent's position utilizing an image capture system, such as the image capture system 100 described above. The electronic communication alert can be issued based upon a combination a combination of a determination of patient motion and/or a patient state, and patient risk parameters. As shown in FIG. 6, a base pressure ulcer risk score is calculated for a subject (Block 602). As described above, the module 116 causes the processor 106 to calculate a base pressure ulcer risk score for the subject using a sensitivity module based on one or more of the characteristics 120. The module may also include one or more caregiver characteristics 122. The one or more characteristics 120 and/or the one or more caregiver characteristics 122 may be furnished to the system 100 by the user, such as a caregiver (e.g., medical personnel), observed and learned by the system 100 utilizing suitable machine learning techniques as described above, and/or integrated from other systems. In some implementations, the module can further include a manual sensitivity adjustment (e.g., the caregiver can manually increase the sensitivity of the alert system for high risk patients, etc.). An alert sensitivity level is determined for the subject based upon the base pressure ulcer risk score (Block 604). As described above, the module 116 can cause the processor 106 to determine an alert sensitivity level for the patient corresponding to base pressure ulcer risk score (e.g., the system 100 can be more sensitive to the movements, positioning, and/or patient states of patients with high base positioning scores, etc.).

In an implementation, the system 100 can generate the alert sensitivity level from a base risk score determined from an module comprising at least one of the patient repositioning protocol, the minimum repositioning protocol, the average alert response time by a caregiver as observed by the system, the medication record as provided in the EMR, and a risk score generated by the system for the patient's recent movements. The module 116 can cause the processor to assign a numerical value for each input using comparisons of the current patient's activities with the activities of all previous patients observed by the system, as graded on a normal distribution scale. The processor 106 can combine these numerical values together, with each input carrying an independent weight. The processor 106 then determines the numerical base risk score for the patient, which determines the sensitivity of the system for that patient. In some implementations, caregivers can further increase or decrease that risk score, thereby further adjusting the sensitivity of the system.

One or more frame images are obtained from an imaging device (Block 606). A plurality of potential bed locations and/or seating platform locations is identified based on the image frames (Block 608). The module 116 can cause the processor 106 to execute one or more object location modules to identify potential bed and/or seating platform locations, as described above. Once a plurality of potential bed and/or seating platform locations are identified, a bed and/or a seating platform is identified based on the potential bed and/or seating platform locations (Block 610). The module 116 can cause the processor 106 to execute one or more object identification modules to reduce the potential bed and/or seating platform locations, to the one or more pixels most likely to represent a bed and/or a seating platform, as described above.

The processor determines at least one state of the patient and/or position of the patient with respect to the bed and/or seating platform (Block 612). For instance, the processor 106 can use one or more of the processing techniques described above to determine at least one state and/or position of the patient (e.g., processes described in FIGS. 3A through 5). For example, the processer 106 can determine if the patient has been lying on the same side for a defined period of time without repositioning.

The processor then determines if the determined state of the patient and/or motion of the patient constitutes a pressure ulcer risk to the patient based on the determined alert sensitivity level (Block 614). As described above, if the patient's base pressure ulcer risk score and corresponding alert sensitivity level are high, the module 116 can cause the processor 106 to determine that lack of movement and/or changes in position over a defined period time causes a risk to the patient. In one or more implementations, the system 100 may utilize suitable machine learning techniques to adjust the sensitivity level in response to changes in the one or more characteristics 120, the one or more caregiver characteristics 122, and/or the at least one state and/or motion of the patient. For example, the processor 106 may increase sensitivity (e.g., alarm earlier) during times when a nurse location system indicates there are no nurses within a certain distance from the room.

An electronic communication alert is issued based on the determination of patient pressure ulcer risk (Block 616). As described above, when a determination is made that the determined patient position or patient state is causing a risk to the patient, the module 116 causes the processor 106 to issue an electronic communication to alert medical personnel. For example, the electronic communication alert can indicate that the patient has remained in the same position for a defined period of time, and/or that the patient requires repositioning.

In some implementations, the system 100 receives feedback from the caregiver(s) about the validity of the electronic communication alert (Block 618). As described above, the module 116 can cause processor 106 to issue an electronic communication alert that can be accepted or dismissed by the caregiver. For example, if the alert is not valid (e.g., the patient has repositioned himself, the patient has transitioned from lying to sitting, the patient has transitioned from the bed, etc.), the caregiver can dismiss the alert. In some implementations, the processor 106 adjusts the alert sensitivity level based on the caregiver feedback (Block 620). As described above, the system 100 may utilize suitable machine learning techniques to adjust the alert sensitivity level of the electronic communication alerts in response to caregiver feedback. For instance, The module 116 can then cause the processor 106 to incorporate the accepting or dismissal into the module to adjust the base risk score (e.g., increase or decrease sensitivity) accordingly. The system 100 can identify an increasingly accurate risk score and corresponding alert sensitivity level for a patient by incorporating electronic communication alert responses over a time period. In this way, the processor 106 determines whether or not to issue future alerts based on the adjusted sensitivity level.

In an implementation, the system 100 can adjust the sensitivity level of the electronic communication alerts based on a machine-learned decision tree built from observed patient behaviors. The module 116 can cause processor 106 to issue an electronic communication alert that can be accepted or dismissed by the caregiver. For example, if the alert is not valid (e.g., the patient is not actually at risk), the caregiver can dismiss the alert. The module 116 can then cause the processor 106 to incorporate the accepting or dismissal into the machine-learned decision tree to adjust the base risk score and corresponding alert sensitivity level (e.g., increase or decrease sensitivity) accordingly. In this implementation, if a future behavior reaches this same alerting node in the decision tree, the system 100 can ignore or intensify its alerting based on this previous feedback.

In one or more implementations, the system 100 can adjust the sensitivity level of the electronic communication alerts in response to a recorded history of patient behaviors that led to an alert. For example, the module 116 can further cause the processor 106 to record the history of patient behaviors (e.g., patient has not changed position in a defined period of time) that resulted in a specific alarm. If these patient behaviors recur in the future, the system the system 100 can ignore or intensify its alerting based on this previous feedback. For instance, the module 116 can cause the processor 106 to incorporate this feedback into the module and/or the decision tree.

In some implementations, the system 100 can adjust the sensitivity level of the electronic communication alerts by retaining a plurality of depth pixels from the time of the alert or the time leading up to the alert. For example, the module 116 can further cause the processor 106 to record the plurality of depth pixels that occurred during or leading to a specific alarm. If this plurality of pixels recurs in the future, the system the system 100 can ignore or intensify its alerting based on this previous feedback. For instance, the module 116 can cause the processor 106 to incorporate this feedback into the module and/or the decision tree.

In one or more implementations, the system 100 can further enhance alerting accuracy by suspending and/or suppressing alerting to minimize false alarms. For example, the module 116 can cause the processor 106 to suppress alerting when the presence of a second person (e.g., caregiver, medical personnel, etc.) is detected in the room and/or when the patient is engaged in certain activities (e.g., eating, exercising, undergoing medical testing, etc.). In some implementations, the system 100 can increase alerting based on the presence and/or absence of the caregiver. For example, the module 116 can cause the processor 106 to issue an alert when the presence of a second person (e.g., caregiver, medical personnel, etc.) is detected in the room, and the second person exits the room without changing the state of the patient (e.g., without repositioning the patient).

CONCLUSION

Generally, any of the functions described herein can be implemented using hardware (e.g., fixed logic circuitry such as integrated circuits), software, firmware, manual processing, or a combination of these implementations. Thus, the blocks discussed in the above disclosure generally represent hardware (e.g., fixed logic circuitry such as integrated circuits), software, firmware, or a combination thereof. In the instance of a hardware implementation, for instance, the various blocks discussed in the above disclosure may be implemented as integrated circuits along with other functionality. Such integrated circuits may include all of the functions of a given block, system or circuit, or a portion of the functions of the block, system or circuit. Further, elements of the blocks, systems or circuits may be implemented across multiple integrated circuits. Such integrated circuits may comprise various integrated circuits including, but not necessarily limited to: a monolithic integrated circuit, a flip chip integrated circuit, a multichip module integrated circuit, and/or a mixed signal integrated circuit. In the instance of a software implementation, for instance, the various blocks discussed in the above disclosure represent executable instructions (e.g., program code) that perform specified tasks when executed on a processor. These executable instructions can be stored in one or more tangible computer readable media. In some such instances, the entire system, block or circuit may be implemented using its software or firmware equivalent. In other instances, one part of a given system, block or circuit may be implemented in software or firmware, while other parts are implemented in hardware.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A system comprising:
a sensor disposed proximate to at least one of a bed or a seating platform and configured to detect a pressure;
an image capture device having an imaging plane, the image capture device configured to receive a plurality of depth frame images comprising a plurality of pixels, the plurality of depth frame images representing a three-dimensional environment corresponding to a physical space;
a computing device in communication with the image capture device and the sensor, the computing device including:
a memory configured to store a patient monitoring module;
a processor coupled to the memory, the processor configured by the patient monitoring module to cause the processor to:
in response to receiving a signal from the sensor indicative of a detected pressure associated with the at least one of the bed or the seating platform, identify a first set of pixels of the plurality of pixels as representing the at least one of the bed or the seating platform;
identify a second set of pixels of the plurality of pixels as representing a portion of the body proximate to the at least one of the bed or the seating platform;
process, via a first processing technique, the second set of pixels to determine a first possible orientation of the portion of the body with respect to the imaging plane, the first possible orientation representing a position of the portion of the body with respect to the at least one of the bed or the seating platform;
process, via a second processing technique, the second set of pixels to generate a second possible orientation of the portion of the body with respect to the imaging plane, the second possible orientation representing the position of the at least one of a body or a portion of the body with respect to the at least one of the bed or the seating platform;
determine whether a subject has changed positions based upon the first possible orientation and the second possible orientation;
transmit an electronic communication alert based upon whether the subject has changed positions; and
receive feedback from an electronic device indicative of a validity of the electronic communication alert;
adjust an electronic communication alert sensitivity level for the determined state of the subject based upon the feedback; and
determine, via one or more machine learning techniques, whether to generate future electronic communication alerts for the determined state of the subject based upon the electronic communication alert sensitivity level.

2. The system as recited in claim 1, wherein the processor is further configured to generate a depth mask representing the physical space based upon the plurality of depth frame images; and identify at least one of a plurality of potential bed locations or a plurality of potential seating platform locations based upon the depth mask.

3. The system as recited in claim 1, wherein the processor is further to determine a probability indicative of whether the subject has changed positions within a predetermined threshold.

4. The system as recited in claim 3, wherein the processor is further configured to determine the probability based upon the first possible orientation, the second possible orientation, and at least one characteristic corresponding to a pressure ulcer risk of the subject.

5. The system as recited in claim 1, wherein the processor is further configured to determine an electronic communication alert sensitivity level associated with the subject based upon at least one characteristic of the subject.

6. The system as recited in claim 1, wherein the processor is further configured to determine whether the subject is at risk for pressure ulcers based on the determination of whether the subject changed positions by comparing an activity of the subject with an activity baseline of the subject.

7. The system as recited in claim 1, wherein the at least one computing device comprises a computer cluster, the computer cluster comprising a plurality of cluster nodes configured to access a shared memory.

8. A method for preventing pressure ulcers for a subject within a medical care environment, the method comprising:
in response to receiving a signal from a sensor indicative of a detected pressure with at least one of a bed or a seating platform, generating, via a processor configured by a patient monitoring module, a depth mask representing a physical space based upon a plurality of depth frame images including a plurality of pixels and received from an image capture device having an imaging plane, the plurality of depth frame images representing a three-dimensional environment corresponding to a physical space;
identifying a first set of pixels of the plurality of pixels as representing the at least one of the bed or the seating platform;
identifying a second set of pixels of the plurality of pixels as representing a portion of a body proximate to the at least one of the bed or the seating platform;
processing, via a first processing technique, the second set of pixels to generate a first possible orientation of the portion of the body with respect to the imaging plane, the first possible orientation representing a position of the portion of the body with respect to the at least one of the bed or the seating platform;
processing, via a second processing technique, the second set of pixels to generate a second possible orientation of the portion of the body with respect to the imaging plane, the second possible orientation representing the position of the portion of the body with respect to the at least one of the bed or the seating platform;
determining whether the subject has changed positions based upon the first possible orientation and the second possible orientation;
transmitting an electronic communication alert based upon whether the subject has changed positions; and receiving feedback from an electronic device indicative of a validity of the electronic communication alert;

adjusting an electronic communication alert sensitivity level for the determined state of the subject based upon the feedback; and determining, via one or more machine learning techniques, whether to generate future electronic communication alerts for the determined state of the subject based upon the electronic communication alert sensitivity level.

9. The method as recited in claim 8, further comprising identifying at least one of a plurality of potential bed locations or a plurality of potential seating platform locations based upon the depth mask.

10. The method as recited in claim 8, wherein identifying one or more first pixels of the plurality of pixels as representing at least one of the bed or the seating platform.

11. The method as recited in claim 8, further comprising determining a probability indicative of whether the subject has changed positions within a predetermined threshold based upon the first possible orientation and the second possible orientation.

12. The method as recited in claim 8, further comprising determining an electronic communication alert sensitivity level associated with the subject based upon at least one characteristic of the subject.

13. A method for preventing pressure ulcers in a medical care environment, the method comprising:

in response to receiving a signal from a sensor indicative of a detected pressure with at least one of a bed or a seating platform, receiving, at a processor configured by a patient monitoring module, a plurality of depth frame images comprising a plurality of pixels the plurality of depth frame images captured by an image capture device having an image plane, the plurality of depth frame images representing a three-dimensional environment corresponding to a physical space;

identifying a first set of pixels of the plurality of pixels as representing the at least one of the bed or the seating platform;

identifying a second set of pixels of the plurality of pixels as representing a portion of a body proximate to the at least one of the bed or the seating platform;

processing, via a first processing technique, the second set of pixels to generate a first possible orientation of the portion of the body with respect to the image plane, the first possible orientation representing a position of the portion of the body with respect to the at least one of the bed or the seating platform;

processing, via a second processing technique, the second set of pixels to generate a second possible orientation of the portion of the body with respect to the image plane, the second possible orientation representing the position of the portion of the body with respect to the at least one of the bed or the seating platform;

determining whether a subject has changed positions based upon the first possible orientation and the second possible orientation;

transmitting an electronic communication alert based upon the determination of whether the subject has changed positions;

receiving feedback from an electronic device indicative of a validity of the electronic communication alert;

adjusting an electronic communication alert sensitivity level for the determined state of the subject based upon the feedback; and determining, via one or more machine learning techniques, whether to generate future electronic communication alerts for the determined state of the subject based upon the electronic communication alert sensitivity level.

14. The method as recited in claim 13, further comprising: generating a depth mask representing the physical space based upon a plurality of depth frame images received from an image capture device; and identifying at least one of a plurality of potential bed locations or a plurality of potential seating platform locations based upon the depth mask.

15. The method as recited in claim 13, further comprising determining a probability based upon the first possible orientation and the second possible orientation.

16. The method as recited in claim 15, further comprising:

processing, via a third processing technique, the second set of pixels to generate a third possible orientation of the portion of the body with respect to the image plane, the third possible orientation representing the position of the portion of the body with respect to the at least one of the bed or the seating platform;

processing, via a fourth processing technique, the second set of pixels to generate a fourth possible orientation of the portion of the body with respect to the image plane, the fourth possible orientation representing the position of the portion of the body with respect to the at least one of the bed or the seating platform; and determine the probability based upon the first possible orientation, the second possible orientation, the third possible orientation, and the fourth possible orientation.

17. The method as recited in claim 13, further comprising identifying a third set of pixels of the plurality of pixels as representing at least one of a second subject or an object relative to the subject.

* * * * *